US012234511B2

(12) United States Patent
Staker et al.

(10) Patent No.: US 12,234,511 B2
(45) Date of Patent: *Feb. 25, 2025

(54) METHODS OF ANALYTE DETECTION

(71) Applicant: Pacific Biosciences of California, Inc., Menlo Park, CA (US)

(72) Inventors: Bryan P. Staker, San Ramon, CA (US); Niandong Liu, San Ramon, CA (US); Michael David McLaughlin, San Jose, CA (US); Bart Lee Staker, Poulsbo, WA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/557,715

(22) Filed: Dec. 21, 2021

(65) Prior Publication Data

US 2024/0052413 A1 Feb. 15, 2024

Related U.S. Application Data

(63) Continuation of application No. 17/061,023, filed on Oct. 1, 2020, now Pat. No. 11,248,266, which is a
(Continued)

(51) Int. Cl.
*G16B 30/00* (2019.01)
*C12Q 1/6874* (2018.01)
(Continued)

(52) U.S. Cl.
CPC .............. *C12Q 1/6874* (2013.01); *G06T 7/73* (2017.01); *G06V 20/69* (2022.01); *G16B 25/30* (2019.02);
(Continued)

(58) Field of Classification Search
None
See application file for complete search history.

(56) References Cited

U.S. PATENT DOCUMENTS

| 4,987,065 A | 1/1991 | Stavrianopoulos et al. |
| 5,302,509 A | 4/1994 | Cheeseman |

(Continued)

FOREIGN PATENT DOCUMENTS

| BY | 4655 | 9/2002 |
| CN | 1584592 A | 2/2005 |

(Continued)

OTHER PUBLICATIONS

Office Action and Translation issued in Chinese Patent Application No. 2019800762595 on May 17, 2022.
(Continued)

*Primary Examiner* — Tahmina N Ansari
(74) *Attorney, Agent, or Firm* — WILSON SONSINI GOODRICH & ROSATI

(57) ABSTRACT

Disclosed herein are methods and systems for detection and discrimination of optical signals from a densely packed substrate. These have broad applications for biomolecule detection near or below the diffraction limit of optical systems, including in improving the efficiency and accuracy of polynucleotide sequencing applications.

20 Claims, 26 Drawing Sheets

Specification includes a Sequence Listing.

Related U.S. Application Data continuation of application No. 16/572,535, filed on Sep. 16, 2019, now Pat. No. 10,829,816, which is a continuation-in-part of application No. 16/458,977, filed on Jul. 1, 2019, now Pat. No. 11,060,140, which is a continuation of application No. 15/925,656, filed on Mar. 19, 2018, now Pat. No. 10,378,053, said application No. 16/572,535 is a continuation-in-part of application No. 14/443,655, filed as application No. PCT/US2013/070797 on Nov. 19, 2013, now abandoned.

(60) Provisional application No. 62/473,163, filed on Mar. 17, 2017, provisional application No. 61/869,020, filed on Aug. 22, 2013, provisional application No. 61/728,067, filed on Nov. 19, 2012.

(51) Int. Cl.
  *G06T 7/73* (2017.01)
  *G06V 20/69* (2022.01)
  *G16B 25/30* (2019.01)

(52) U.S. Cl.
  CPC .......... *G16B 30/00* (2019.02); *G06F 2218/18* (2023.01); *G06T 2207/20056* (2013.01); *G06T 2207/30072* (2013.01); *G06V 20/695* (2022.01)

(56) References Cited

U.S. PATENT DOCUMENTS

| | | | |
|---|---|---|---|
| 5,494,810 A | 2/1996 | Barany et al. | |
| 5,763,594 A | 6/1998 | Hiatt et al. | |
| 6,103,474 A | 8/2000 | Dellinger et al. | |
| 6,214,987 B1 | 4/2001 | Hiatt et al. | |
| 6,232,465 B1 | 5/2001 | Hiatt et al. | |
| 6,654,505 B2 | 11/2003 | Bridgham et al. | |
| 6,852,487 B1 | 2/2005 | Barany et al. | |
| 7,057,026 B2 | 6/2006 | Barnes et al. | |
| 7,122,319 B2 | 10/2006 | Liu et al. | |
| 7,769,548 B2 | 8/2010 | Garcia | |
| 7,838,302 B2 * | 11/2010 | Zhuang | C09K 11/06 436/171 |
| 7,948,015 B2 | 5/2011 | Rothberg et al. | |
| 7,960,104 B2 | 6/2011 | Drmanac et al. | |
| 8,149,418 B2 | 4/2012 | Tearney et al. | |
| 8,158,346 B2 | 4/2012 | Balasubramanian et al. | |
| 8,175,452 B1 | 5/2012 | Staker et al. | |
| 8,218,834 B2 * | 7/2012 | Homman | G01N 33/5076 382/128 |
| 8,222,047 B2 | 7/2012 | Duffy et al. | |
| 8,428,454 B2 | 4/2013 | Staker et al. | |
| 8,676,013 B2 | 3/2014 | Bouma et al. | |
| 9,193,998 B2 | 11/2015 | Khurana et al. | |
| 9,551,026 B2 | 1/2017 | Fernandez et al. | |
| 10,378,053 B2 * | 8/2019 | Staker | G16B 25/30 |
| 10,510,435 B2 | 12/2019 | Cai et al. | |
| 10,829,816 B2 | 11/2020 | Staker et al. | |
| 10,901,230 B2 | 1/2021 | Skinner et al. | |
| 11,047,005 B2 * | 6/2021 | Staker | G16B 30/00 |
| 11,060,140 B2 * | 7/2021 | Staker | G16B 30/10 |
| 11,248,266 B2 | 2/2022 | Staker et al. | |
| 11,293,052 B2 * | 4/2022 | Church | C12Q 1/6874 |
| 11,313,793 B2 * | 4/2022 | Bertacco | G01N 21/41 |
| 11,434,532 B2 | 9/2022 | Staker et al. | |
| 11,435,356 B2 | 9/2022 | Staker et al. | |
| 11,474,107 B2 | 10/2022 | Staker et al. | |
| 11,650,202 B2 | 5/2023 | Staker et al. | |
| 2002/0028519 A1 | 3/2002 | Yguerabide et al. | |
| 2002/0086322 A1 | 7/2002 | Yu et al. | |
| 2003/0118595 A1 | 6/2003 | Niemeyer et al. | |
| 2003/0207300 A1 | 11/2003 | Matray et al. | |
| 2003/0215862 A1 | 11/2003 | Parce et al. | |
| 2004/0191794 A1 | 9/2004 | Weindel et al. | |
| 2005/0049796 A1 | 3/2005 | Webb et al. | |
| 2005/0148100 A1 | 7/2005 | Su et al. | |
| 2005/0153320 A1 | 7/2005 | Herron et al. | |
| 2005/0250094 A1 | 11/2005 | Storhoff et al. | |
| 2006/0275782 A1 | 12/2006 | Gunderson et al. | |
| 2007/0072208 A1 * | 3/2007 | Drmanac | G01N 15/1404 435/5 |
| 2007/0087382 A1 | 4/2007 | Howorka et al. | |
| 2008/0018898 A1 | 1/2008 | Gunstream et al. | |
| 2008/0161194 A1 | 7/2008 | Turner et al. | |
| 2008/0317325 A1 | 12/2008 | Ortyn et al. | |
| 2009/0017271 A1 | 1/2009 | Meiring et al. | |
| 2009/0075314 A1 | 3/2009 | Barak et al. | |
| 2009/0081688 A1 | 3/2009 | Luo et al. | |
| 2009/0317810 A1 | 12/2009 | Lofton-Day et al. | |
| 2010/0075407 A1 | 3/2010 | Duffy et al. | |
| 2010/0075865 A1 | 3/2010 | Trau et al. | |
| 2010/0301398 A1 | 12/2010 | Rothberg et al. | |
| 2011/0009296 A1 | 1/2011 | Kain et al. | |
| 2011/0071048 A1 | 3/2011 | Oshima | |
| 2011/0165559 A1 | 7/2011 | Lane et al. | |
| 2012/0020537 A1 | 1/2012 | Garcia et al. | |
| 2012/0052490 A1 | 3/2012 | Eid et al. | |
| 2012/0226653 A1 | 9/2012 | McLaughlin et al. | |
| 2012/0307121 A1 | 12/2012 | Lu et al. | |
| 2012/0330567 A1 | 12/2012 | Bauer et al. | |
| 2013/0045872 A1 | 2/2013 | Zhou et al. | |
| 2013/0053256 A1 | 2/2013 | Hubbell | |
| 2013/0059740 A1 | 3/2013 | Drmanac et al. | |
| 2013/0124100 A1 | 5/2013 | Drmanac et al. | |
| 2013/0265459 A1 | 10/2013 | Duparre et al. | |
| 2014/0194311 A1 | 7/2014 | Gullberg et al. | |
| 2014/0226881 A1 | 8/2014 | Piestun et al. | |
| 2014/0287468 A1 | 9/2014 | Richard | |
| 2015/0008188 A1 | 1/2015 | Warner | |
| 2015/0152473 A1 | 6/2015 | Nadeau et al. | |
| 2015/0267251 A1 | 9/2015 | Cai et al. | |
| 2015/0330974 A1 | 11/2015 | Staker et al. | |
| 2016/0003809 A1 | 1/2016 | Dunaway | |
| 2016/0201119 A1 | 7/2016 | Staker et al. | |
| 2016/0223528 A1 | 8/2016 | Sahin et al. | |
| 2017/0152554 A1 * | 6/2017 | Drmanac | C12Q 1/6837 |
| 2017/0220733 A1 | 8/2017 | Zhuang et al. | |
| 2018/0023124 A1 * | 1/2018 | Collins | C12Q 1/6827 435/6.11 |
| 2018/0088112 A1 | 3/2018 | Fan et al. | |
| 2018/0252936 A1 | 9/2018 | Owens et al. | |
| 2018/0274028 A1 | 9/2018 | Staker et al. | |
| 2019/0276886 A1 | 9/2019 | Skinner et al. | |
| 2019/0284552 A1 | 9/2019 | Collins et al. | |
| 2019/0323080 A1 * | 10/2019 | Staker | G16B 30/10 |
| 2019/0353887 A1 | 11/2019 | Riza | |
| 2020/0063200 A1 | 2/2020 | Staker et al. | |
| 2020/0140933 A1 | 5/2020 | Staker et al. | |
| 2020/0217850 A1 * | 7/2020 | Liu | G01N 33/5008 |
| 2020/0393691 A1 | 12/2020 | Owens et al. | |
| 2021/0072233 A1 | 3/2021 | Staker et al. | |
| 2021/0277469 A1 * | 9/2021 | Staker | G16B 25/30 |
| 2021/0381036 A1 | 12/2021 | Furtado et al. | |
| 2023/0392202 A1 | 12/2023 | Staker et al. | |
| 2024/0005488 A1 | 1/2024 | Ballinger et al. | |
| 2024/0069012 A1 | 2/2024 | Staker et al. | |

FOREIGN PATENT DOCUMENTS

| | | |
|---|---|---|
| CN | 1653480 A | 8/2005 |
| CN | 101865843 A | 10/2010 |
| CN | 101865843 B | 5/2012 |
| CN | 107735497 A | 2/2018 |
| CN | 110031907 A | 7/2019 |
| EP | 1388587 A4 | 12/2006 |
| EP | 2251435 A1 | 11/2010 |
| EP | 2620510 A1 | 7/2013 |
| EP | 3595806 A1 | 1/2020 |
| JP | 2002524739 A | 8/2002 |
| JP | 2007536528 A | 12/2007 |
| JP | 2008249711 A | 10/2008 |
| JP | 2010500002 A | 1/2010 |
| JP | 2010500563 A | 1/2010 |

(56) References Cited

FOREIGN PATENT DOCUMENTS

| | | |
|---|---|---|
| JP | 2014164004 A | 9/2014 |
| JP | 2017504039 A | 2/2017 |
| KR | 20160048714 A | 5/2016 |
| WO | WO-9511461 A1 | 4/1995 |
| WO | WO-9967641 A2 | 12/1999 |
| WO | WO-9967641 A3 | 3/2000 |
| WO | WO-2005113817 A9 | 8/2006 |
| WO | WO-2007097754 A1 | 8/2007 |
| WO | WO-2007133831 A2 | 11/2007 |
| WO | WO-2008033167 A2 | 3/2008 |
| WO | WO-2008091296 A2 | 7/2008 |
| WO | WO-2009097626 A2 | 8/2009 |
| WO | WO-2011137183 A1 | 11/2011 |
| WO | WO-2012031011 A1 | 3/2012 |
| WO | WO-2014015269 A1 | 1/2014 |
| WO | WO-2014078855 A1 | 5/2014 |
| WO | WO-2014137474 A1 | 9/2014 |
| WO | WO-2015027112 A1 | 2/2015 |
| WO | WO-2015104245 A1 | 7/2015 |
| WO | WO-2016018986 A1 | 2/2016 |
| WO | WO-2016074338 A1 | 5/2016 |
| WO | WO-2016134191 A1 | 8/2016 |
| WO | WO-2016156845 A1 | 10/2016 |
| WO | WO-2017079573 A1 | 5/2017 |
| WO | WO-2017079593 A1 | 5/2017 |
| WO | WO-2017123770 A1 | 7/2017 |
| WO | WO-2017161251 A1 | 9/2017 |
| WO | WO-2017196527 A1 | 11/2017 |
| WO | WO-2017223041 A1 | 12/2017 |
| WO | WO-2018161013 A1 | 9/2018 |
| WO | WO-2018170518 A1 | 9/2018 |
| WO | WO-2018175402 A1 | 9/2018 |

OTHER PUBLICATIONS

U.S. Appl. No. 18/052,880 Notice of Allowance dated Feb. 14, 2024.
Babcock et al., A high-density 3D localization algorithm for stochastic optical reconstruction microscopy. Optical Nanoscopy vol. 1, Article No. 6 (2012).
Bentley et al. Accurate whole human genome sequencing using reversible terminator chemistry. Nature 456(7218):53-59 (2008).
Canadian Patent Application No. 2,891,939 Office Action dated Apr. 12, 2018.
Canadian Patent Application No. 2,891,939 Office Action dated Jul. 27, 2016.
Canadian Patent Application No. 2,891,939 Office Action dated May 31, 2017.
Canadian Patent Application No. 2,921,809 Office Action dated Jan. 19, 2017.
Canadian Patent Application No. 2,921,809 Office Action dated Nov. 14, 2017.
CAS Registry No. 361411-90-7 (entered into database 2001) (Year: 2001).
Chai J, et al. Single-molecule protein arrays enabled by scanning probe block copolymer lithography. Proc Natl Acad Sci U S A. Dec. 6, 2011;108(49):19521-5. Epub Nov. 21, 2011.
Chinese Patent Application No. 201380070866.3 Office Action date Apr. 6, 2017.
Chinese Patent Application No. 201380070866.3 Office Action dated Mar. 5, 2018.
Chinese Patent Application No. 201480056710.4 Office Action dated Jan. 3, 2017.
Chinese Patent Application No. 201480056710.4 Office Action dated Nov. 28, 2017.
Cho et al. Optimization of Aptamer Microarray Technology for Multiple Protein Targets. Analytica Chimica Acta 564(1):82-90 (2006).
Dai et al., Optical imaging of individual biomolecules in densely packed clusters. Nature Nanotechnology 11: 798-807 (2016).
Drmanac et al. Human Genome Sequencing Using Unchained Base Reads on Self-Assembling DNA nanoarrays. Science Reports, 327:78-81 (Jan. 1, 2010).
European Patent Application No. 18768551 Supplementary Search Report dated May 6, 2021.
European Patent Application No. 18772384 Search Report dated Nov. 19, 2020.
European Patent Application No. 13855452.2 Extended Search Report dated Aug. 2, 2016.
European Patent Application No. 14837796.3 Examination Report dated Apr. 26, 2018.
European Patent Application No. 14837796.3 Extended Search Report dated Mar. 22, 2017.
Extended European Search Report issued in European Patent Application No. 19861989.2 on May 19, 2022.
Gavrilovic et al. Quantification of Colocalization and Cross-Tk Based on Spectral Angles. J Microsc 324(3):311-324 (2009).
Gu et al.: Multiplex single-molecule interaction profiling of DNA-barcoded proteins. Nature 515:54-557 and Supplementary Information, entire document 2014.
Gunderson et al.: Decoding randomly ordered DNA arrays. Genome Research 14(5):870-877 (2004).
Guo et al. Four-color DNA sequencing with 3'-O-modified nucleotide reversible terminators and chemically cleavable fluorescent dideoxynucleotides. PNAS USA 105(27):9145-9150 (2008).
Guo et al. Supporting Information for Four-color DNA sequencing with 3'-O-modified nucleotide reversible terminators and chemically cleavable fluorescent dideoxynucleotides. PNAS USA PNAS USA 105(27):9145-9150 (2008).
Hager et al. Arrays of Individual DNA Molecules on Nanopatterned Substrates. Scientific Reports 7:42075 (2017).
Illumina Sequencing Technology, Technology Spotlight: Illumina® Sequencing, Illumina, Inc. (2010).
Japanese Patent Application No. 2015-543118 Office Action dated Sep. 25, 2017.
Japanese Patent Application No. 2016-536467 Office Action dated Aug. 9, 2018.
Ju et al.: Four-Color DNA Sequencing by Synthesis Using Cleavable Fluorescent Nucleotide Reversible Terminators. PNAS USA 103:19635-19640 (2006).
Kao et al. BayesCall: A Model-Based Base-Cling algorithm for High-Throughput Short-Read Sequencing. Genome Research 19:1884-1895 (2009).
Kozlov, et al. Efficient strategies for the conjugation of oligonucleotides to antibodies enabling highly sensitive protein detection. Biopolymers. Apr. 5, 2004;73(5):621-30.
Kumar et al. PEG-Labeled Nucleotides and Nanopore Detection for Single Molecule DNA Sequencing by Synthesis. Scientific Reports 2:1-8 (2012).
Lee et al., Ion-sensitive field-effect transistor for biological sensing. Sensors. 9(9):7111-7131 (2009).
Levene et al., Zero-mode waveguides for single-molecule analysis at high concentrations. Science. 299(5607)682-686 (2003).
Levy et al. Advancements in Next-Generation Sequencing. Annu Rev Genomics Hum Genet 17:95-115 (2016).
Liu et al. Comparison of Next-Generation Sequencing Systems. J Biomed Biotechnol 2012: 251364 (2012).
Moerner, et al., Methods of single-molecule fluorescence spectroscopy and microscopy. Review of Scientific Instruments. 74(8):3597-3619 (2003).
Mukamel et al., Statistical deconvolution for superresolution fluorescence microscopy. Biophys J 102(10):2391-2400 (2012).
Munck et al., Sub-diffraction imaging on standard microscopes through photobleaching microscopy with non-linear processing. J Cell Sci 125(Pt 9):2257-2266 (2012).
PCT/US2013/070797 International Preliminary Report on Patentability dated Jan. 16, 2015.
PCT/US2013/070797 International Search Report and Written Opinion dated Feb. 21, 2014.
PCT/US2014/052186 International Preliminary Report on Patentability dated Sep. 21, 2015.
PCT/US2014/052186 International Search Report and Written Opinion dated Dec. 17, 2014.

(56) References Cited

OTHER PUBLICATIONS

PCT/US2018/023187 International Preliminary Report on Patentability dated Sep. 26, 2019.
PCT/US2018/023187 International Search Report and Written Opinion dated May 31, 2018.
PCT/US2018/023310 International Preliminary Report on Patentability dated Sep. 24, 2019.
PCT/US2018/023310 International Search Report and Written Opinion dated Sep. 4, 2018.
PCT/US2018/051183 International Preliminary Report on Patentability dated Mar. 17, 2020.
PCT/US2018/051183 International Search Report and Written Opinion dated Jan. 18, 2019.
PCT/US2019/015243 International Search Report and Written Opinion dated Mar. 22, 2019.
PCT/US2019/051796 International Search Report and Written Opinion dated Jan. 3, 2020.
Ramanathan et al., An integrative approach for the optical sequencing of single DNA molecules. Analytical Biochemistry 330(2): 227-241 (2004).
Riley et al. Reed-Solomon Codes. https://www.cs.cmu.edu/-guyb/realworld/reedsolomon/reedsolomoncodes.html (1996).
Rotman, B., Measurement of activity of single molecules of beta-D-galactosidase. Proceedings of the National Academy of Sciences of the United States of America. 47:1981-1991 (1961).
Russian Patent Application No. 2015123570 Office Action dated May 22, 2017.
Russian Patent Application No. 2016106961 Office Action dated Aug. 7, 2017.
Small et al., Fluorophore localization algorithms for super-resolution microscopy. Nature Methods 11: 267-279 (2014).
Song et al., Aptamer-based biosensors, TrAC Trends in Analytical Chemistry, vol. 27, Issue 2, 2008,pp. 108-117, ISSN 0165-9936.
Song et al., Aptamer-based biosensors. Trends in Analytical Chemistry. 27(2)108-117 (2008).
Svobodova et al., Comparison of Different Methods for Generation of Single-Stranded DNA for SELEX Processes. Anal Bioanal Chem 404(3): 835-842 (2012).
Tuerk. Systematic evolution of ligands by exponential enrichment: RNA ligands to bacteriophage T4 DNA polymerase. Science 249:505-510 (1990).
U.S. Appl. No. 16/458,977 Non-Final Office Action dated Jan. 22, 2021.
U.S. Appl. No. 16/496,923 Non-Final Office Action dated Jul. 16, 2021.
U.S. Appl. No. 16/572,535 Non-Final Office Action dated Mar. 30, 2020.
U.S. Appl. No. 17/204,795 Non-Final Office Action dated Oct. 25, 2021.
U.S. Appl. No. 17/327,588 Non-Final Office Action dated Sep. 27, 2021.
U.S. Appl. No. 14/912,883 Final Office Action dated Jan. 3, 2020.
U.S. Appl. No. 17/084,017 Office Action dated Feb. 2, 2021.
U.S. Appl. No. 14/443,655 Office Action dated Jun. 12, 2018.
U.S. Appl. No. 14/443,655 Office Action dated Jun. 25, 2019.
U.S. Appl. No. 14/443,655 Office Action dated Mar. 9, 2017.
U.S. Appl. No. 14/443,655 Office Action dated Nov. 14, 2016.
U.S. Appl. No. 14/443,655 Office Action dated Oct. 18, 2017.
U.S. Appl. No. 14/912,883 Office Action dated Apr. 3, 2019.
U.S. Appl. No. 15/925,656 Office Action dated Sep. 27, 2018.
Wang et al., An adaptive decorrelation method removes Illumina DNA base-calling errors caused by crosstalk between adjacent clusters. Scientific Reports vol. 7, Article No. 41348 (2017).
Wang et al., Sub-diffraction limit localization of proteins in volumetric space using Bayesian restoration of fluorescence images from ultrathin specimens. PLoS Comput Biol 8(8):e1002671 (2012).
Benner, et al. Evolution, language and analogy in functional genomics. Trends in Genetics, 17:414-418 (2001).
Carey, Francis A., and Richard J. Sundberg. Advanced organic chemistry: part A: structure and mechanisms. Springer Science & Business Media. (1992).
Colowick, Sidney P et al. Methods of Enzymology. Academic Press, Inc : pp. 1-390 (1990).
Creighton. Proteins: Structures and Molecular Properties. W.H. Freeman pp. 79-86 (1983).
Lehninger, A. L. Biochemistry, Worth Publishers, Inc. Current Edition. (2021).
May et al. How Many Species are there on Earth? Science 241:1441-1449 (1988).
PCT/US2019/015243 International Preliminary Report on Patentability dated Jul. 28, 2020.
PCT/US2019/051796 International Preliminary Report on Patentability dated Mar. 23, 2021.
Remington's Pharmaceutical Sciences. 18th Edition, Mack Publishing Company (1990).
Sambrook, Joseph et al. Molecular Cloning: A Laboratory Manual, 2nd Edition. Cold Spring Harbor Laboratory Press (1989).
U.S. Appl. No. 17/955,426 Office Action dated Apr. 10, 2024.
U.S. Appl. No. 18/181,440 Notice of Allowance dated Mar. 27, 2024.
Wang, Xiaofang et al.: Characterization of denaturation and renaturation of DNA for DNA hybridization. Environmental Health and Toxicology 29:e2014007, 8 pages.

* cited by examiner

|     |     |     |     |
|-----|-----|-----|-----|
| P1  | P2  | P3  | P4  |
| P5  | P6  | P7  | P8  |
| P9  | P10 | P11 | P12 |
| P13 | P14 | P15 | P16 |

FIG. 10A

| | | | |
|---|---|---|---|
| RED | BLU | GRN | YLW |
| RED | BLU | GRN | YLW |
| RED | BLU | GRN | YLW |
| RED | BLU | GRN | YLW |

Cycle 1 Image: Probe Pool #1

FIG. 10B

| | | | |
|---|---|---|---|
| RED | RED | RED | RED |
| BLU | BLU | BLU | BLU |
| GRN | GRN | GRN | GRN |
| YLW | YLW | YLW | YLW |

Cycle 2 Image: Probe Pool #2

FIG. 10C

| Target | Color Sequence | Binary ID | Hex ID | Decimal ID |
|---|---|---|---|---|
| B1 | R-G-R-G-R-G | 101010 | 2A | 42 |
| B2 | R-R-G-G-G-R | 110001 | 31 | 49 |
| B3 | G-G-G-R-R-R | 000111 | 07 | 7 |

Slide #177

| Field # | # Targets | All | P53 | BRAF | EGFR | KRAS |
|---|---|---|---|---|---|---|
| 1 | 833 | 72 | 35 | 5 | 11 | 21 |
| 2 | 928 | 92 | 52 | 6 | 12 | 22 |
| 3 | 949 | 121 | 58 | 12 | 9 | 42 |
| 4 | 1284 | 237 | 67 | 23 | 27 | 120 |
| 5 | 885 | 132 | 61 | 12 | 13 | 46 |
| 6 | 1022 | 178 | 80 | 13 | 15 | 70 |
| 7 | 925 | 122 | 53 | 11 | 9 | 49 |
| 8 | 1106 | 200 | 80 | 16 | 25 | 79 |
| 9 | 692 | 59 | 19 | 15 | 1 | 24 |
| 10 | 938 | 110 | 45 | 7 | 11 | 47 |
| 11 | 940 | 109 | 55 | 6 | 15 | 33 |
| 12 | 1179 | 166 | 75 | 12 | 13 | 65 |
| Total | 11681 | 1598 | 681 | 138 | 161 | 618 |

| Total | All | P53 | BRAF | EGFR | KRAS |
|---|---|---|---|---|---|
| # Targets | 13.7% | 5.8% | 1.2% | 1.4% | 5.3% |
| All | 100.0% | 42.6% | 8.6% | 10.1% | 38.7% |

Slide #179

| Field # | # Targets | All | P53 | BRAF | EGFR | KRAS |
|---|---|---|---|---|---|---|
| 1 | 1161 | 154 | 79 | 21 | 9 | 45 |
| 2 | 2536 | 402 | 200 | 36 | 56 | 110 |
| 3 | 1579 | 191 | 101 | 4 | 27 | 59 |
| 4 | 1197 | 146 | 81 | 8 | 22 | 35 |
| 5 | 1293 | 169 | 90 | 8 | 23 | 48 |
| 6 | 1063 | 116 | 62 | 11 | 11 | 32 |
| 7 | 1130 | 120 | 49 | 14 | 10 | 47 |
| 8 | 1012 | 84 | 30 | 11 | 10 | 33 |
| 9 | 1516 | 175 | 82 | 19 | 17 | 57 |
| 10 | 1527 | 182 | 107 | 8 | 10 | 57 |
| 11 | 1129 | 95 | 34 | 24 | 10 | 27 |
| 12 | 1219 | 150 | 84 | 8 | 20 | 38 |
| Total | 16362 | 1984 | 999 | 172 | 225 | 588 |

| Total | All | P53 | BRAF | EGFR | KRAS |
|---|---|---|---|---|---|
| # Targets | 12.1% | 6.1% | 1.1% | 1.4% | 3.6% |
| All | 100.0% | 50.4% | 8.7% | 11.3% | 29.6% |

FIG. 16A

| Target | Color Sequence | Binary ID | Hex ID | Decimal ID |
|---|---|---|---|---|
| P53 | R-G-R-G-R-G-R-G-R-G | 1010101010 | 2AA | 682 |
| BRAF | G-R-G-R-G-R-G-R-G-R | 0101010101 | 155 | 341 |
| EGFR | R-G-G-R-R-G-G-R-R-G | 1001100110 | 266 | 614 |
| KRAS | G-R-R-G-G-R-R-G-G-R | 0110011001 | 199 | 409 |

FIG. 16B

| Label | Parameter | Low | Med | High | Unit |
|---|---|---|---|---|---|
| dTP | target protein density | 1.51 | 1.51 | 1.51 | 1/um^2 |
| rHT | # high abundance proteins per # of target proteins | 25,000 | 250 | 1 | NA |
| rHP | # of high abundance proteins per pixel | 1,000 | 10 | 0.04 | NA |
| rXT | # of pixels per target protein | 25 | 25 | 25 | NA |
| nF | # of fields | 2,500 | 250 | 250 | NA |
| nP | total # proteins in plasma proteome | 9,719 | 9,719 | 9,719 | NA |
| iLP | min protein index (sorted least conc to greatest) | 0 | 4,025 | 9,436 | NA |
| iHP | max protein index (sorted least conc to greatest) | 9,574 | 9,864 | 9,719 | NA |
| pP | percent of proteome identified | 98.5% | 58.0% | 2.9% | % |
| dX | pixel size | 162.5 | 162.5 | 162.5 | nm |
| nX | # pixels per field | 4,000,000 | 4,000,000 | 4,000,000 | NA |
| aA | chip area | 264.1 | 26.4 | 26.4 | mm^2 |
| dLC | Measured concentration, low-end | 30 | $8.2 \times 10^4$ | $2.0 \times 10^7$ | fg/mL |
| dUC | Measured concentration, upper-end | $3.1 \times 10^8$ | $8.5 \times 10^{10}$ | $1.0 \times 10^{14}$ | fg/mL |

FIG. 22

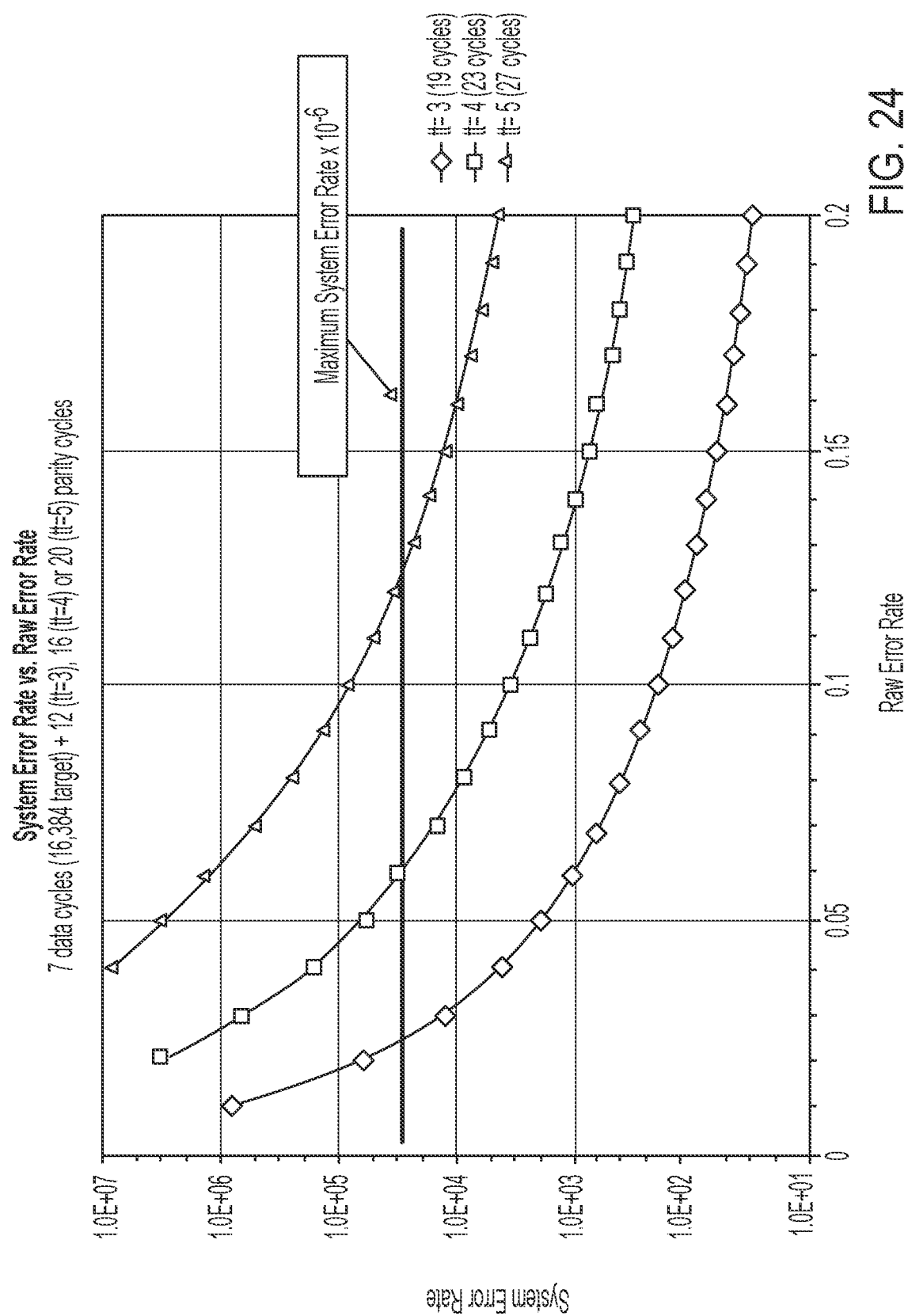

METHODS OF ANALYTE DETECTION

CROSS-REFERENCE TO RELATED APPLICATIONS

This application is a Continuation of U.S. patent application Ser. No. 17/061,023, filed on Oct. 1, 2020, which is a Continuation of U.S. patent application Ser. No. 16/572,535, filed on Sep. 16, 2019, now U.S. Pat. No. 10,829,816, which is a Continuation in Part of U.S. patent application Ser. No. 16/458,977, filed on Jul. 1, 2019, now U.S. Pat. No. 11,060,140, which is a Continuation of U.S. patent application Ser. No. 15/925,656, filed on Mar. 19, 2018, now U.S. Pat. No. 10,378,053, which claims the benefit of priority from U.S. Provisional Application No. 62/473,163, filed Mar. 17, 2017. U.S. patent application Ser. No. 16/572,535, filed on Sep. 16, 2019, now U.S. Pat. No. 10,829,816, is also a Continuation in Part of U.S. patent application Ser. No. 14/443,655, filed on May 18, 2015, which is a National Stage Entry of International Patent Application No. PCT/US2013/070797, filed on Nov. 19, 2013, which claims the benefit of priority from U.S. Provisional Application No. 61/869,020, filed on Aug. 22, 2013, and from U.S. Provisional Application No. 61/728,067, filed on Nov. 19, 2012, the entire disclosures of which are hereby incorporated by reference in their entirety for all purposes.

The instant application contains a Sequence Listing which has been submitted in ASCII format via EFS-Web and hereby incorporated by reference in its entirety. Said ASCII copy, created on Oct. 22, 2019, is named 55495-804-306 SL.txt and is 5,586 bytes in size.

BACKGROUND

1. Technical Field

This disclosure relates to the fields of diagnostics and communications theory, and specifically relates to methods for digital analysis of molecular analytes.

2. Description of the Related Art

Multiple molecular and biochemical approaches are available for molecular analyte identification and quantification. Examples include commonly used nucleic acid based assays, such as qPCR (quantitative polymerase chain reaction) and DNA microarray, and protein based approaches, such as immunoassay and mass spectrometry. However, various limitations exist in current analyte analysis technologies. For example, current methods have limitations of sensitivity, especially where analytes are present in biological samples at low copy numbers or in low concentrations. Most of the nucleic acid quantification technologies involve sample amplification for higher sensitivity. However, amplification techniques introduce biases and inaccuracies into the quantification. Moreover, amplification is not possible for protein and peptides. Due to lack of sensitivity, approaches for detection and quantification often require relatively large sample volumes. Current methods are also limited in their capacity for identification and quantification of a large number of analytes. Quantification of all of mRNA and proteins in a sample requires high multiplexity and large dynamic range. In addition, current technologies lack the capability to detect and quantify nucleic acids and proteins simultaneously.

Current methods often generate errors during analyte detection and quantification due to conditions such as weak signal detection, false positives, and other mistakes. These errors may result in the misidentification and inaccurate quantification of analytes.

Therefore, methods and systems are needed for analyte analysis that allows for high sensitivity with small sample volume, high multiplexity, large dynamic range and the ability to detect protein and nucleic acid molecules in a single assay. More importantly, methods of error correction to correct for analyte detection errors are needed. The present invention addresses these and other limitations of the prior art by introducing sensitive single molecule identification and quantification of biological analytes with a digital readout.

SUMMARY OF THE INVENTION

In some embodiments, provided herein is a method for sequencing a plurality of polynucleotides immobilized at high density on a surface of a substrate at a single molecule resolution, comprising: providing a substrate comprising a surface, wherein the surface comprises a plurality of polynucleotides immobilized on the surface at discrete locations, and wherein said surface comprises reagents for sequencing by synthesis; performing a plurality of cycles of single molecule sequencing by synthesis comprising, each cycle comprising: contacting said polynucleotides with a set of reversible terminator nucleotides comprising a detectable label; imaging a field of said surface with an optical system to detect an optical signal from each nucleotide incorporated into said polynucleotides, thereby detecting a plurality of optical signals in said field for said cycle; determining a peak location from each of said plurality of optical signals from images of said field from at least two of said plurality of cycles; overlaying said peak locations for each optical signal and applying an optical distribution model at each cluster of optical signals to determine a relative position of each detected analyte on said surface with improved accuracy; deconvolving said optical signals in each field image from each cycle using said determined relative position and a deconvolution function; identifying said detectable labels incorporated into said polynucleotide for each field and each cycle from said deconvolved optical signals; and sequencing said plurality of polynucleotides immobilized on the surface of the substrate from said identified detectable labels across said plurality of cycles at each polynucleotide position.

In some embodiments, the polynucleotides are DNA concatemers. In some embodiments, the set of reversible terminator nucleotides comprise at least four distinct nucleotides each with a distinct detectable label. In some embodiments, the deconvolution comp¬rises removing interfering optical signals from neighboring polynucleotides using a center-to-center distance between said neighboring polynucleotides from said determined rela¬tive positions. In some embodiments, the deconvolution function comprises nearest neighbor variable regression.

Polynucleotides

In some embodiments, the polynucleotides are densely packed on said substrate such that there is overlap between optical signals emitted by said detectable labels from probes bound to adjacent polynucleotides comprising distinct polynucleotide sequences to be sequenced. In some embodiments, the polynucleotides are immobilized on said surface at an average density of more than 4 molecules per square micron. In some embodiments, the imaging of said surface is performed at a resolution of one pixel per 300 nm or higher along an axis of the image field. In some embodiments, the sequencing method further comprises generating an oversampled image with a higher pixel density from each of said field images from each cycle. In some embodiments, overlaying said peak locations comprises aligning positions of said optical signal peaks detected in each field for a plurality of said cycles to generate a cluster of optical peak positions for each polynucleotide from said plurality of cycles. In some embodiments, the optical distribution model is a point spread function. In some embodiments, the relative position is determined for a plurality of said polynucleotides in said field. In some embodiments, the relative position is determined with an accuracy of within 10 nm RMS.

According to some embodiments, also provided herein is a method for accurately determining a relative position of analytes immobilized on the surface of a densely packed substrate, comprising: providing a substrate comprising a surface, wherein the surface comprises a plurality of analytes immobilized on the surface at discrete locations; performing a plurality of cycles of probe binding and signal detection on said surface, (each cycle comprising: contacting said analytes with a plurality of probes from a probe set, wherein said probes comprise a detectable label, wherein each of said probes binds specifically to a target analyte; and imaging a field of said surface with an optical system to detect a plurality of optical signals from individual probes bound to said analytes at discrete locations on said surface); determining a peak location from each of said plurality of optical signals from images of said field from at least two of said plurality of cycles; and overlaying said peak locations for each optical signal and applying an optical distribution model at each cluster of optical signals to determine a relative position of each detected analyte on said surface with improved accuracy.

In some embodiments, the method further comprises: deconvolving said optical signals in each field image from each cycle using said determined relative position and a deconvolution function; and identifying said detectable labels bound to said immobilized analytes for each field and each cycle from said deconvolved optical signals. In some embodiments, the method further comprises using said detectable label identity for each analyte detected at each cycle to identify a plurality of said analytes on said substrate.

In some embodiments, the deconvolution comprises removing interfering optical signals from neighboring analytes using a center-to-center distance between said neighboring analytes from said determined relative positions of said neighboring analytes. In some embodiments, the deconvolution function comprises nearest neighbor variable regression. In some embodiments, the single molecules are single biomolecules.

In some embodiments, the analytes immobilized on said surface are spaced apart on average less than the diffraction limit of the light emitted by the detectable labels and imaged by the optical system. In some embodiments, the immobilized analytes comprises a minimum center-to-center distance between adjacent analytes of less than 500 nm. In some embodiments, overlaying said peak locations comprises aligning positions of said optical signal peaks detected in each field for a plurality of said cycles to generate a cluster of optical peak positions for each analyte from said plurality of cycles. In some embodiments, the relative position is determined with an accuracy of within 10 nm RMS. In some embodiments, the method is capable of resolving optical signals from a surface at a density of ~4-25 per square micron.

Also provided herein, according to some embodiments, is a method for identifying a plurality of densely packed analytes immobilized on a surface of a substrate, comprising: providing a substrate comprising a surface, wherein the surface comprises a plurality of analytes immobilized on the surface at discrete locations; performing a plurality of cycles of probe binding and signal detection on said surface, (each cycle comprising: contacting said analytes with a plurality of probes from a probe set, wherein said probes comprise a detectable label, wherein each of said probes binds specifically to a target analyte; and imaging a field of said surface with an optical system to detect a plurality of optical signals from individual probes bound to said analytes); determining a peak location from each of said plurality of optical signals from images of said field from at least two of said plurality of cycles; overlaying said peak locations for each optical signal and applying an optical distribution model at each cluster of optical signals to determine a relative position of each detected analyte on said surface with improved accuracy; deconvolving said optical signals in each field image from each cycle using said determined relative position and a deconvolution function; determining the identity of each detectable label in each field and each cycle from said deconvolved optical signals; and using said detectable label identity for each analyte detected at each cycle to identify a plurality of said analytes on said substrate.

Other aspects of the present disclosure provide systems and methods for detecting a plurality of analytes, comprising: obtaining a plurality of ordered probe reagent sets, each of the ordered probe reagent sets comprising one or more probes directed to a defined subset of N distinct target analytes, wherein the N distinct target analytes are immobilized on spatially separate regions of a substrate, and each of the probes is detectably labeled. The method also includes steps for performing at least M cycles of probe binding and signal detection, each cycle comprising one or more passes, wherein a pass comprises use of at least one of the ordered probe reagent sets. The method comprises detecting from the at least M cycles a presence or an absence of a plurality of signals from the spatially separate regions of the substrate.

In some embodiments, the method comprises determining from the plurality of signals at least K bits of information per cycle for one or more of the N distinct target analytes, wherein the at least K bits of information are used to determine L total bits of information, wherein $K \times M = L$ bits of information and $L > \log 2 (N)$, and wherein the L bits of information are used to determine a presence or an absence of one or more of the N distinct target analytes.

In some embodiments, $L > \log 2 (N)$, and L comprises bits of information for target identification. In other embodiments, $L > \log 2 (N)$, and L comprises bits of information that are ordered in a predetermined order.

In one embodiment, the predetermined order is a random order. In another embodiment, $L > \log 2 (N)$, and L comprises bits of information comprising a key for decoding an order of the plurality of ordered probe reagent sets.

The method also includes digitizing the plurality of signals to expand a dynamic range of detection of the plurality of signals. In some embodiments, the at least K bits of information comprise information about the number of passes in a cycle. In another embodiment, the at least K bits of information comprise information about the absence of a signal for one of the N distinct target analytes.

In one embodiment, the detectable label is a fluorescent label. In another embodiment, the probe comprises an antibody. In one embodiment, the antibody is conjugated directly to a label. The antibody can also be bound to a secondary antibody conjugated to a label. In other embodiments, the probe comprises an aptamer. In one embodiment, the aptamer comprises a homopolymeric base region. In other embodiments, the plurality of analytes comprises a protein, a peptide aptamer, or a nucleic acid molecule.

In some embodiments, the method can include detecting from the at least M cycles a presence or an absence of a plurality of optical signals. The method can also include detecting from the at least M cycles a presence or an absence of a plurality of electrical signals.

In one embodiment, the method is computer implemented. In another embodiment, K is one bit of information per cycle. In other embodiments, K is two bits of information per cycle. K can also be three or more bits of information per cycle.

In another embodiment, the method includes determining from the L bits of information an error correction for the plurality of output signals. The error correction method can be a Reed-Solomon code.

In one embodiment, the method comprises determining a number of ordered probe reagent sets based on the number of N distinct target analytes. The method can also include determining a type of probe reagent sets based on the type of N distinct target analytes.

In an embodiment, the N distinct target analytes are present in a sample, which is divided into a plurality of aliquots diluted to a plurality of distinct final dilutions, and each of the plurality of aliquots is immobilized onto a distinct section of the substrate. In another embodiment, one of the distinct final dilutions is determined based on a probable naturally-occurring concentration of at least one of the N distinct target analytes. In another embodiment, a concentration of one of the N distinct target analytes is determined by counting the occurrences of the target analyte within one of the distinct sections and adjusting the count according to the dilution of the respective aliquot.

Another aspect of the present disclosure provides a kit for detecting a plurality of analytes, comprising: a plurality of ordered probe reagent sets, each of the ordered pro be reagent sets comprising one or more probes directed to a defined subset of N distinct target analytes, wherein the N distinct target analytes are immobilized on spatially separate regions of a substrate, and each of the probes is detectably labeled. In some embodiments, the kit includes instructions for detecting said N distinct analytes based on a plurality of detectable signals. In some embodiments, the kit includes instructions for performing at least M cycles of probe binding and signal detection, each cycle comprising one or more passes, wherein a pass comprises use of at least one of the ordered probe reagent sets. In some embodiments, the kit includes instructions for detecting from the at least M cycles a presence or an absence of a plurality of signals from the spatially separate regions of said substrate. In some embodiments, the kit also includes instructions for determining from the plurality of signals at least K bits of information per cycle for one or more of said N distinct target analytes, wherein the at least K bits of information are used to determine L total bits of information, wherein $K \times M = L$ bits of information and $L > \log 2 (N)$, and wherein said L bits of information are used to determine a presence or an absence of one or more of the N distinct target analytes.

In some embodiments, the kit includes one or more probes that comprise an antibody. In other embodiments, the label is a fluorescent label. In another embodiment, the probe is an antibody. In one embodiment, the antibody is conjugated directly to a label. In yet another embodiment, the antibody is bound to a secondary antibody conjugated to a label. In other embodiments, the probe comprises an aptamer. The aptamer can comprise a homopolymeric base region. In some embodiments, the plurality of analytes comprises a protein, a peptide aptamer, or a nucleic acid molecule.

In other embodiments, $L > \log 2 (N)$. In another embodiment, $M \leq N$. The kit can also include instructions for determining an identification of each of the N distinct target analytes using the L bits of information, wherein L comprises bits of information for target identification.

In some embodiments, the kit can include instructions for determining an order of said plurality of ordered probe reagent sets using the L bits of information, wherein L comprises bits of information that are ordered in a predetermined order. The predetermined order can be a random order. The kit can also include instructions for using a key for decoding an order of the plurality of ordered probe reagent sets.

Also provided herein, according to some embodiments, is a method for processing a plurality of analytes, comprising: providing said plurality of analytes disposed adjacent to N spatially separate regions of a substrate; performing a plurality of cycles of probe binding to and signal detection from at least a subset of said plurality of analytes to generate observed signal sequences comprising L total bits of information for said at least said subset of said plurality of analytes, wherein said L total bits of information comprises one or more redundant bits of information; and using an algorithm to process said observed signal sequences, including said one or more redundant bits of information, to generate decoded signal sequences corresponding to said at least said subset of said plurality of analytes, which decoded signal sequences are generated at an error rate less than 5% over at least 20 cycles of said plurality of cycles. In some embodiments, said observed signal sequences comprise K bits of information for a cycle of said plurality of cycles, and wherein said L total bits of information for identifying an interaction between a probe and an analyte is determined by multiplying K by a number of said plurality of cycles. In some embodiments, L is greater than or equal to Loge (N). The method of claim 1, further comprising digitizing said observed signal sequences to expand a measure of dynamic range for detecting a plurality of signals from said plurality of analytes. In some embodiments, an analyte of said plurality of analytes is a nucleic acid molecule. In some embodiments, an analyte of said plurality of analytes is a protein or a polypeptide. In some embodiments, performing said plurality of cycles of probe binding to and signal detection from said at least said subset of said plurality of analytes comprises bringing an analyte of said plurality of analytes in contact with a probe that comprises an optical label, and detecting a signal from said optical label. In some embodiments, said probe comprises a nucleotide analog. In some embodiments, said probe comprises a polynucleotide. In some embodiments, said probe comprises a polypeptide. In some embodiments, said polypeptide comprises an antibody. In some embodiments, performing said plurality of cycles of probe binding to and signal detection from said at least said subset of said plurality of analytes comprises bringing an analyte of said plurality of analytes in contact with a probe, and using an enzyme to couple said probe to said analyte. In some embodiments, contacting said probe to said analyte is achieved through a reaction mediated by said enzyme. In some embodiments, said analyte is a polynucleotide, said probe is a nucleotide, and said enzyme is a polymerase. In some embodiments, said decoded signal sequences are generated based at least in part on expected signal sequences corresponding to said plurality of analytes.

Also provided herein, according to some embodiments, is a method for characterizing a plurality of analytes, comprising: providing an array comprising said plurality of analytes; performing a plurality of cycles of probe binding to and signal detection from said plurality of analytes to generate an observed signal sequence; and using a computer algorithm to process said observed signal sequence, based at least in part on an expected signal sequence corresponding to said plurality of analytes, to generate a decoded signal sequence at an error at an error rate less than 5% over at least 20 cycles. In some embodiments, said plurality of analytes comprises nucleic acid molecules. In some embodiments, said plurality of analytes comprises separate clonal populations of said nucleic acid molecules. In some embodiments, an analyte of said plurality of analytes is a protein or a polypeptide. In some embodiments, performing said plurality of cycles of probe binding to and signal detection from said plurality of analytes comprises bringing an analyte of said plurality of analytes in contact with a probe that comprises an optical label, and detecting a signal from said optical label.

Also provided herein, according to some embodiments, is a system for determining the identity of a plurality of analytes, comprising an optical imaging device configured to image a plurality of optical signals from a field of a substrate over a plurality of cycles of probe binding to analytes immobilized on a surface of the substrate; and an image processing module, said module configured to: determine a peak location from each of said plurality of optical signals from images of said field from at least two of said plurality of cycles; determine a relative position of each detected analyte on said surface with improved accuracy by applying an optical distribution model to each cluster of optical signals from said plurality of cycles; and deconvolve said optical signals in each field image from each cycle using said determined relative position and a deconvolution function.

In some embodiments, the image processing module is further configured to determine an identity of said analytes immobilized on said surface using said deconvolved optical signals. In some embodiments, the optical image device comprises a moveable stage defining a scannable area. In some embodiments, the optical image device comprises a sensor and optical magnification configured to sample a surface of a substrate at below the diffraction limit in said scannable area. In some embodiments, the optical imaging system further comprising a substrate comprising analytes immobilized to a surface of the substrate at a center-to-center spacing below the diffraction limit. In some embodiments, the deconvolution comprises removing interfering optical signals from neighboring analytes using a center-to-center distance between said neighboring analytes from said determined relative positions of said neighboring analytes.

BRIEF DESCRIPTION OF THE DRAWINGS

The disclosed embodiments have other advantages and features which will be more readily apparent from the following detailed description of the invention and the appended claims, when taken in conjunction with the accompanying drawings, in which:

FIGS. 10A-10D illustrate an example of sixteen target proteins arranged on a substrate. FIGS. 10B and 10C depict examples of images of the substrate after contact with different probe pools, according to one embodiment of the invention.

FIG. 16A shows the numbers of specific target analytes identified on different portions of a substrate, according to one embodiment of the invention.

FIG. 16B shows color sequences and IDs for target analytes, according to one embodiment of the invention.

FIG. 22 shows a list of estimated values for various abundance regions of a substrate, according to one embodiment of the invention.

FIG. 24 illustrates a graph of system error rate vs. raw error rate for identifying target analytes, according to one embodiment of the invention.

DETAILED DESCRIPTION

Figure 1:
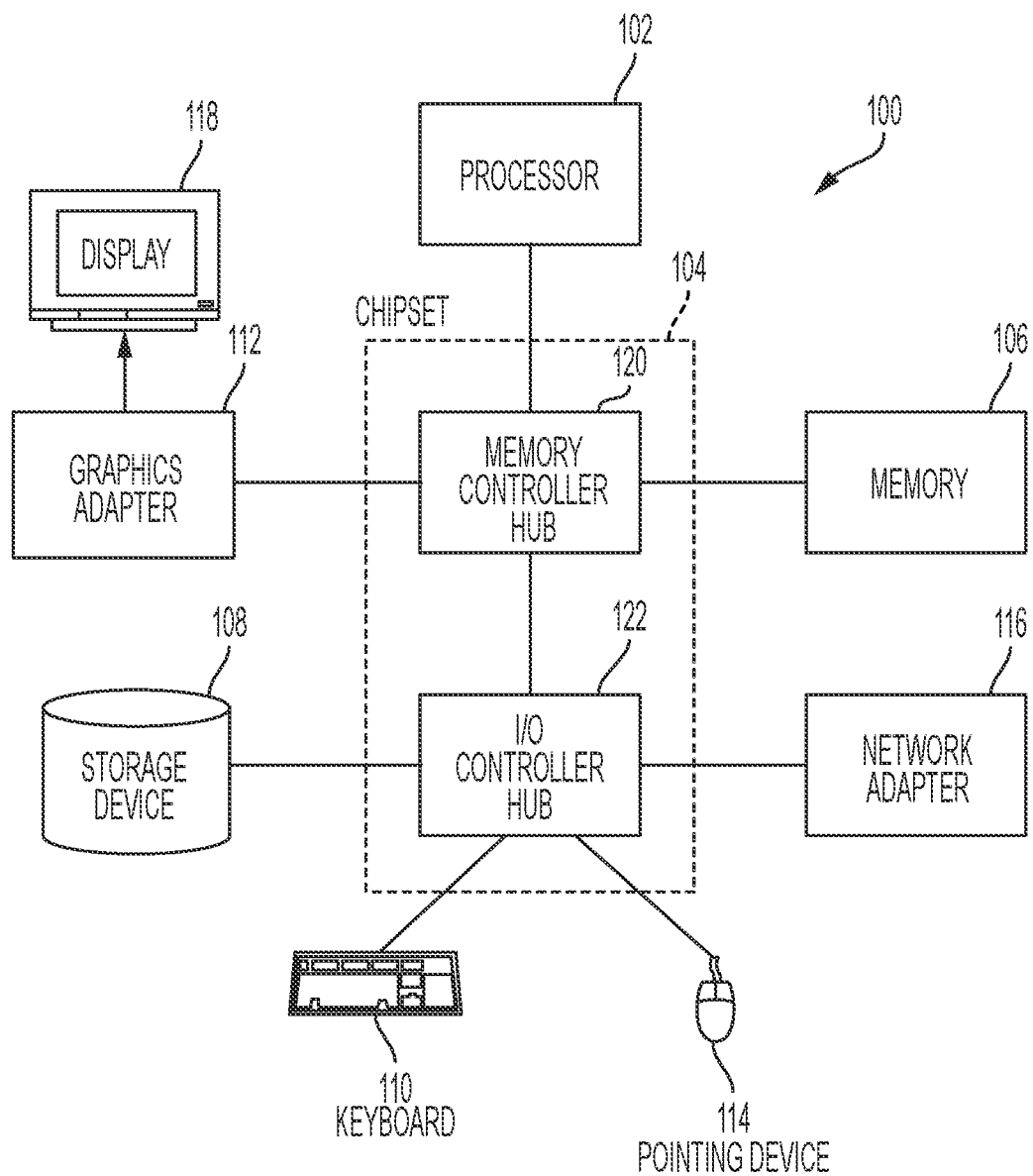
FIG. 1 is a high-level block diagram illustrating an example of a computer, according to one embodiment of the invention.

The figures and the following description relate to various embodiments of the invention by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Definitions

As used herein, the term center-to-center distance refers to a distance between two adjacent molecules as measured by the difference between the average position of each molecule on a substrate. The term average minimum center-to-center distance refers specifically to the average distance between the center of each analyte disposed on the substrate and the center of its nearest neighboring analyte, although the term center-to-center distance refers also to the minimum center-to-center distance in the context of limitations corresponding to the density of analytes on the substrate.

As used herein, the term "pitch" or "average effective pitch" is generally used to refer to average minimum center-to-center distance. In the context of regular arrays of analytes, pitch may also be used to determine a center-to-center distance between adjacent molecules along a defined axis.

As used herein, the term "overlaying" (e.g., overlaying images) refers to overlaying images from different cycles to generate a distribution of detected optical signals (e.g., position and intensity, or position of peak) from each analyte over a plurality of cycles. This distribution of detected optical signals can be generated by overlaying images, overlaying artificial processed images, or overlaying datasets comprising positional information. Thus, as used herein, the term "overlaying images" encompasses any of these mechanisms to generate a distribution of position information for optical signals from a single probe bound to a single analyte for each of a plurality of cycles.

A "cycle" is defined by completion of one or more passes and stripping of the detectable label from the substrate. Subsequent cycles of one or more passes per cycle can be performed. For the methods and systems described herein, multiple cycles are performed on a single substrate or sample. For DNA sequencing, multiple cycles requires the use of a reversible terminator and a removable detectable label from an incorporated nucleotide. For proteins, multiple cycles requires that the probe removal (stripping) conditions either maintain proteins folded in their proper configuration, or that the probes used are chosen to bind to peptide sequences so that the binding efficiency is independent of the protein fold configuration.

A "pass" in a detection assay refers to a process where a plurality of probes comprising a detectable label are introduced to the bound analytes, selective binding occurs between the probes and distinct target analytes, and a plurality of signals are detected from the detectable labels. A pass includes introduction of a set of antibodies that bind specifically to a target analyte. A pass can also include introduction of a set of labelled nucleotides for incorporation into the growing strand during sequencing by synthesis. There can be multiple passes of different sets of probes before the substrate is stripped of all detectable labels, or before the detectable label or reversible terminator is removed from an incorporated nucleotide during sequencing. In general, if four nucleotides are used during a pass, a cycle will only consist of a single pass for standard four nucleotide sequencing by synthesis.

As used herein, an image refers to an image of a field taken during a cycle or a pass within a cycle. In some embodiments, a single image is limited to detection of a single color of a detectable label.

As used herein, the term "field" refers to a single region of a substrate that is imaged. During a typical assay a single field is imaged at least once per cycle. For example, for a 20 cycle assay, with 4 colors, there can be 20*4=80 images, all of the same field.

As used herein, the term detectable label refers to a molecule bound to a probe that is capable of generating a detectable optical signal when the probe is bound to a target analyte and imaged using an optical imaging system. The detectable label can be directly or indirectly bound to, hybridized to, conjugated to, or covalently linked to the probe. In some embodiments, the detectable label is a fluorescent molecule or a chemiluminescent molecule. The probe can be detected optically via the detectable label.

As used herein, the term optical distribution model refers to a statistical distribution of probabilities for light detection from a point source. These include, for example, a Gaussian distribution. The Gaussian distribution can be modified to include anticipated aberrations in detection to generate a point spread function as an optical distribution model.

A "target analyte" or "analyte" refers to a molecule, compound, substance or component that is to be identified, quantified, and otherwise characterized. A target analyte can comprise by way of example, but not limitation to, an atom, a compound, a molecule (of any molecular size), a polypeptide, a protein (folded or unfolded), an oligonucleotide molecule (RNA, cDNA, or DNA), a fragment thereof, a modified molecule thereof, such as a modified nucleic acid, or a combination thereof. In an embodiment, a target analyte polypeptide or protein is about nine amino acids in length. Generally, a target analyte can be at any of a wide range of concentrations (e.g., from the mg/mL to ag/mL range), in any volume of solution (e.g., as low as the picoliter range). For example, samples of blood, serum, formalin-fixed paraffin embedded (FFPE) tissue, saliva, or urine could contain various target analytes. The target analytes are recognized by probes, which are used to identify and quantify the target analytes using electrical or optical detection methods.

Modifications to a target protein, for example, can include post-translational modifications, such as attaching to a protein other biochemical functional groups (such as acetate, phosphate, various lipids and carbohydrates), changing the chemical nature of an amino acid (e.g. citrullination), or making structural changes (e.g. formation of disulfide bridges). Examples of post-translational modifications also include, but are not limited to, addition of hydrophobic groups for membrane localization (e.g., myristoylation, palmitoylation), addition of cofactors for enhanced enzymatic activity (e.g., lipolyation), modifications of translation factors (e.g., diphthamide formation), addition of chemical groups (e.g., acylation, alkylation, amide bond formation, glycosylation, oxidation), sugar modifications (glycation), addition of other proteins or peptides (ubiquination), or changes to the chemical nature of amino acids (e.g., deamidation, carbamylation).

In other embodiments, target analytes are oligonucleotides that have been modified. Examples of DNA modifications include DNA methylation and histone modification.

A "probe" as used herein refers to a molecule that is capable of binding to other molecules (e.g., oligonucleotides comprising DNA or RNA, polypeptides or full-length proteins, etc.), cellular components or structures (lipids, cell walls, etc.), or cells for detecting or assessing the properties of the molecules, cellular components or structures, or cells. The probe comprises a structure or component that binds to the target analyte. In some embodiments, multiple probes may recognize different parts of the same target analyte. Examples of probes include, but are not limited to, an aptamer, an antibody, a polypeptide, an oligonucleotide (DNA, RNA), or any combination thereof. Antibodies, aptamers, oligonucleotide sequences and combinations thereof as probes are also described in detail below.

The probe can comprise a detectable label that is used to detect the binding of the probe to a target analyte. The probe can be directly or indirectly bound to, hybridized to, conjugated to, or covalently linked to the target analyte.

The probe can comprise a tag that is used to detect the presence of the target analyte. The tag can be directly or indirectly bound to, hybridized to, conjugated to, or covalently linked to the target analyte binding component. In some embodiments, the tag is a detectable label, such as a fluorescent molecule or a chemiluminescent molecule. In other embodiments, the tag comprises an oligonucleotide sequence that has a homopolymeric base region (e.g., a poly-A tail). The probe can be detected electrically, optically, or chemically via the tag.

As used herein, the term "tag" refers to a molecule capable of detecting a target analyte). The tag can be an oligonucleotide sequence that has a homopolymeric base region (e.g., a poly-A tail). In other embodiments, the tag is a label, such as a fluorescent label. The tag can comprise, but is not limited to, a fluorescent molecule, chemiluminescent molecule, chromophore, enzyme, enzyme substrate, enzyme cofactor, enzyme inhibitor, dye, metal ion, metal sol, ligand (e.g., biotin, avidin, streptavidin or haptens), radioactive isotope, and the like. The tag can be directly or indirectly bound to, hybridizes to, conjugated to, or covalently linked to the probe.

A "protein" or "polypeptide" or "peptide" refers to a molecule of two or more amino acids, amino acid analogs, or other peptidomimetics. The protein can be folded or unfolded (denatured). The polypeptide or peptide can have a secondary structure, such as an α-helix, β sheet, or other conformation. As used herein, the term "amino acid" refers to either natural and/or unnatural or synthetic amino acids, including glycine and both the D or L optical isomers, and amino acid analogs and peptidomimetics. A peptide can be two or more amino acids in length. Longer length peptides are often referred to as polypeptides. A protein can refer to full length proteins, analogs, and fragments thereof are encompassed by the definition. The terms also include post-expression modifications of the protein or polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A protein or polypeptide may be obtained directly from the source organism, or may be recombinantly or synthetically produced.

Proteins can be identified and characterized by a peptide sequence, side-chain modifications, and/or tertiary structure. Side-chain modifications include phosphorylation, acetylation, sugars, etc. Phosphorylation of hydroxyl groups from serine, threonine and tyrosine amino acids are particularly important modifications of interest.

The term "in vivo" refers to processes that occur in a living organism.

The term "mammal" as used herein includes both humans and non-humans and include but is not limited to humans, non-human primates, canines, felines, murines, bovines, equines, and porcines.

"Sample" as used herein includes a specimen, culture, or collection from a biological material. Samples may be derived from or taken from a mammal, including, but not limited to, humans, monkey, rat, or mice. Samples may be include materials such as, but not limited to, cultures, blood, tissue, formalin-fixed paraffin embedded (FFPE) tissue, saliva, hair, feces, urine, and the like. These examples are not to be construed as limiting the sample types applicable to the present invention.

A "bit" as used herein refers to a basic unit of information in computing and digital communications. A bit can have only one of two values. The most common representations of these values are 0 and 1. The term bit is a contraction of binary digit. In one example, a system that uses 4 bits of information can create 16 different values (as shown in Table 1A). All single digit hexadecimal numbers can be written with 4 bits. Binary-coded decimal is a digital encoding method for numbers using decimal notation, with each decimal digit represented by four bits. In another example, a calculation using 8 bits, there are 28 (or 256) possible values.

TABLE 1A

Example of bit values

| Binary | Octal | Decimal | Hexadecimal |
| --- | --- | --- | --- |
| 0000 | 0 | 0 | 0 |
| 0001 | 1 | 1 | 1 |
| 0010 | 2 | 2 | 2 |
| 0011 | 3 | 3 | 3 |
| 0100 | 4 | 4 | 4 |
| 0101 | 5 | 5 | 5 |
| 0110 | 6 | 6 | 6 |
| 0111 | 7 | 7 | 7 |
| 1000 | 10 | 8 | 8 |
| 1001 | 11 | 9 | 9 |
| 1010 | 12 | 10 | A |

TABLE 1A-continued

Example of bit values

| Binary | Octal | Decimal | Hexadecimal |
| --- | --- | --- | --- |
| 1011 | 13 | 11 | B |
| 1100 | 14 | 12 | C |
| 1101 | 15 | 13 | D |
| 1110 | 16 | 14 | E |
| 1111 | 17 | 15 | F |

A "pass" in a detection assay refers to a process where a plurality of probes are introduced to the bound analytes, selective binding occurs between the probes and distinct target analytes, and a plurality of signals are detected from the probes. A pass includes introduction of a set of antibodies that bind specifically to a target analyte. There can be multiple passes of different sets of probes before the substrate is stripped of all probes.

A "cycle" is defined by completion of one or more passes and stripping of the probes from the substrate. Subsequent cycles of one or more passes per cycle can be performed. Multiple cycles can be performed on a single substrate or sample. For proteins, multiple cycles will require that the probe removal (stripping) conditions either maintain proteins folded in their proper configuration, or that the probes used are chosen to bind to peptide sequences so that the binding efficiency is independent of the protein fold configuration.

It must be noted that, as used in the specification and the appended claims, the singular forms "a," "an," and "the" include plural referents unless the context clearly dictates otherwise.

OVERVIEW

Detection techniques for highly multiplexed single molecule identification and quantification of analytes using both optical and electrical systems are disclosed. Analytes can include, but are not limited to, a protein, a peptide, DNA and RNA molecules, with and without modifications. Electrical detection is accomplished using ion sensitive field effect transistors (ISFET) integrated with MEMS (microelectrical mechanical systems) structures for enhanced sensitivity. Techniques include poly-A tags with and without differential stops, complementary specific and non-specific probes for detailed characterization of analytes, highly multiplexed single molecule identification and quantification using antibody probes. Optical detection is accomplished by detection of fluorescent or luminescent tags.

1. Computer System

FIG. 1 is a high-level block diagram illustrating an example of a computer 100 for use in analyzing molecular analytes, in accordance with one embodiment. Illustrated are at least one processor 102 coupled to a chipset 104. The chipset 104 includes a memory controller hub 120 and an input/output (I/O) controller hub 122. A memory 106 and a graphics adapter 112 are coupled to the memory controller hub 122, and a display device 118 is coupled to the graphics adapter 112. A storage device 108, keyboard 110, pointing device 114, and network adapter 116 are coupled to the I/O controller hub 122. Other embodiments of the computer 100 have different architectures. For example, the memory 106 is directly coupled to the processor 102 in some embodiments.

The storage device 108 is a non-transitory computer-readable storage medium such as a hard drive, compact disk read-only memory (CD-ROM), DVD, or a solid-state memory device. The memory 106 holds instructions and data used by the processor 102. The pointing device 114 is used in combination with the keyboard 110 to input data into the computer system 100. The graphics adapter 112 displays images and other information on the display device 118. In some embodiments, the display device 118 includes a touch screen capability for receiving user input and selections. The network adapter 116 couples the computer system 100 to the network. Some embodiments of the computer 100 have different and/or other components than those shown in FIG. 1. For example, the server can be formed of multiple blade servers and lack a display device, keyboard, and other components.

The computer 100 is adapted to execute computer program modules for providing functionality described herein. As used herein, the term "module" refers to computer program instructions and other logic used to provide the specified functionality. Thus, a module can be implemented in hardware, firmware, and/or software. In one embodiment, program modules formed of executable computer program instructions are stored on the storage device 108, loaded into the memory 106, and executed by the processor 102.

2. Compositions

Compositions are provided that bind and tag analytes, such as DNA, RNA, protein, and peptides, in a specific manner, such that individual molecules can be detected and counted.

Antibodies as Probes

In some embodiments, the probe comprises antibodies that can be used as probes to detect target analytes in a sample. As described below, antibodies are immunoglobulins that specifically bind to target proteins or polypeptides. In a preferred embodiment, antibodies used in the invention are monoclonal and can bind specifically to folded or unfolded proteins.

"Antibody" refers to an immunoglobulin that specifically binds to, and is thereby defined as complementary with, another molecule. The antibody is a glycoprotein produced by B-cells that is used by the immune system to identify and neutralize foreign objects, such as bacteria and viruses. The antibody recognizes a unique part of the foreign target, called an antigen. Antibodies are typically made of basic structural units: two large heavy chains and two small light chains. The antibody can be monoclonal or polyclonal, and can be naturally occurring, modified or recombinant. Antibodies can be prepared by techniques that are well known in the art, such as immunization of a host and collection of sera (polyclonal), or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies can include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like.

A "monoclonal antibody" (mAB) is an immunoglobulin produced by a single clone of lymphocytes, i.e. the progeny of a single B cell, which recognizes only a single epitope on an antigen. In addition, aggregates, polymers, and conjugates of immunoglobulins or their fragments can be used where appropriate so long as binding affinity for a particular target is maintained. An antibody (primary antibody) can be covalently linked to a detectable label (e.g., fluorescent label). In other embodiments, a primary antibody binds to a secondary antibody that is covalently linked to a detectable label. In some embodiments, the primary antibody is conjugated to a labeled oligonucleotide molecule, as described in U.S. Pat. No. 7,122,319 to Liu eta!. filed on Nov. 5, 2003, which is incorporated by reference in its entirety.

Figure 2A:
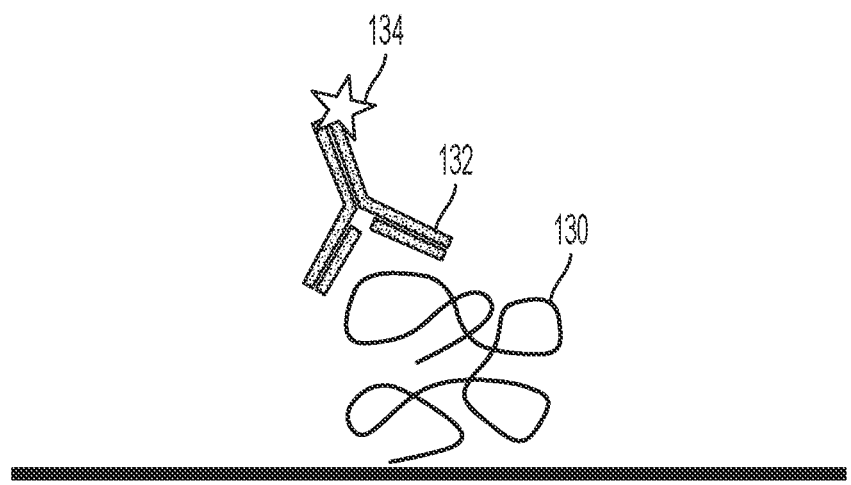
FIG. 2A illustrates an example of a probe comprising an antibody and a detectable tag, where the probe binds a target protein, according to one embodiment of the invention.
Figure 2B:
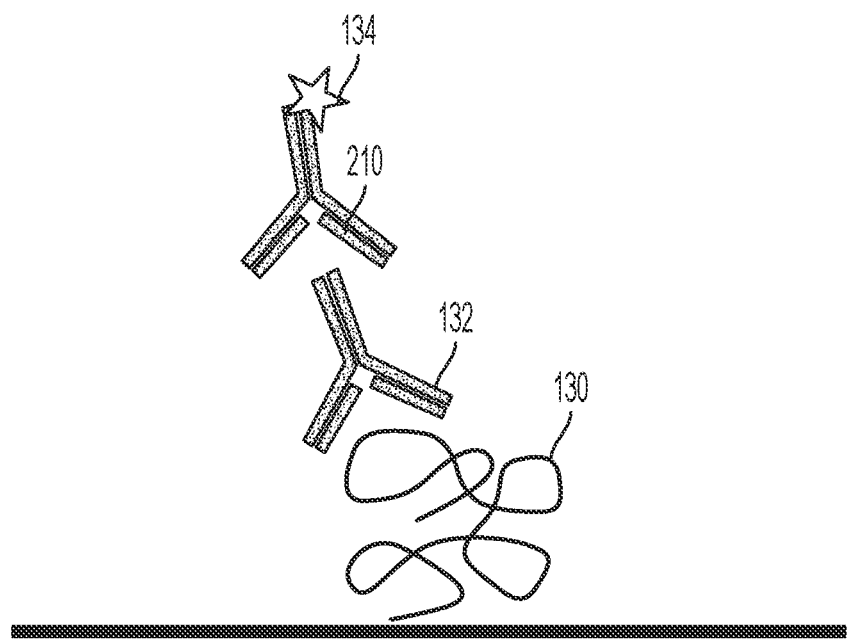
FIG. 2B illustrates an example of a probe comprising a primary antibody and a secondary antibody conjugated to detectable tag, according to one embodiment of the invention.

FIG. 2A illustrates an example of a probe comprising an antibody 132 and a detectable tag 134, and the probe binds a target analyte 130. In FIG. 2B, an example is shown of a probe comprising a primary antibody 132 and a secondary antibody 210. The secondary antibody 210 is conjugated to a detectable label 134.

Aptamers

An "aptamer" as used herein refers to a nucleic acid molecule or a peptide molecule that binds to a target analyte. Anaptamer can be a component of a probe. In some embodiments, nucleic acid aptamers are nucleic acid molecules that have been engineered through repeated rounds of in vitro selection or equivalently, SELEX (systematic evolution of ligands by exponential enrichment) to bind to various molecular targets, such as small molecules, proteins, nucleic acids, and even cells, tissues and organisms. See Tuerk C & Gold L (1990). Other methods of aptamer generation include SAAB (selected and amplified binding site) and CASTing (cyclic amplification and selection of targets). Systematic evolution of ligands by exponential enrichment: RNA ligands to bacteriophage T4 DNA polymerase. Science. 249:505-510; M. Svobodova, A. Pinto, P. Nadal and C. K. O' Sullivan. (2012) Comparison of different methods for generation of single-stranded DNA for SELEX processes. "Anal Bioanal Chem" (2012) 404:835-842. Aptamers can bind to a unique n-mer sequence found in a protein (e.g., denatured or folded protein) or polypeptide. In one embodiment, the aptamer binds to a unique 9-mer sequence. In some embodiments, aptamer can bind to a tag, such as an oligonucleotide strand comprising a homopolymeric base region (e.g., a poly-A tail).

Figure 3:
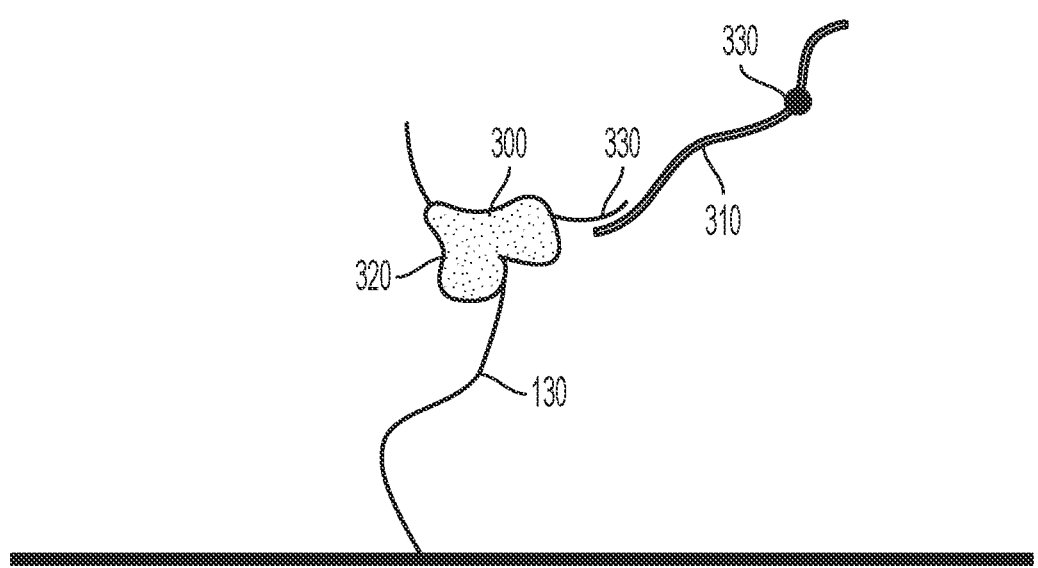
FIG. 3 shows a target analyte bound to a probe comprising an aptamer and a tail region, according to one embodiment of the invention.

In some embodiments, the probe comprises an aptamer and a tail region. An aptamer is an oligonucleotide or peptide molecule that binds to a specific target analyte. FIG. 3 shows a target analyte 130 that is bound to an aptamer 300. The aptamer 300 includes a probe region 320, which is configured to specifically bind to the target analyte 130. The probe region 320 can comprise a protein, peptide, or nucleic acid, and the probe region 320 recognizes and binds to the target analyte. Each probe region 320 can be coupled to a tag. In some embodiments, the tag is a tail region 310. The tail region 310 is an oligonucleotide molecule of at least 25 nucleotides and serves as a template for polynucleotide synthesis. The tail region 310 is generally a single-stranded DNA molecule, but could also be an RNA molecule. In one embodiment, the tail region 310 is covalently linked to the probe region 330 through a nucleic acid backbone.

In another embodiment, a portion of the tail region 310 specifically binds to a linker region 330. The linker region 330 is covalently linked to the probe region 320 through a nucleic acid backbone. The linker region 330 can be configured to specifically bind to a portion of one tail region 310, or portions of multiple tail regions 310. In an embodiment, the linker region 330 comprises at least 10 nucleotides. In another embodiment, the linker region 330 comprises 20-25 nucleotides. A probe region 320 can be covalently linked to a single linker region 330, or can be covalently linked to multiple distinct linker regions 330 that each specifically binds to a portion of a distinct tail region 310.

The tail region 310 provides a template for polynucleotide synthesis. During polynucleotide synthesis, one hydrogen ion is released for each nucleotide incorporated along the tail region template. A plurality of these hydrogen ions can be detected as an electrical output signal by a transistor. A minimum threshold number of hydrogen ions must be released for the transistor to detect an electrical output signal. For example, the minimum threshold number could be 25 depending on details of the detector configuration. In that case, the tail region 310 must be at least 25 nucleotides long. In some embodiments, the tail region 310 is at least 25, 100, 200, 1000, or 10,000 nucleotides in length. The tail region 310 can include one or more homopolymeric base regions. For example, the tail region 310 can be a poly-A, poly-C, poly-G, or a poly-T tail. In another embodiment, the tail region 310 comprises a homopolymeric base region followed by a different homopolymeric base region, for example a poly-A tail followed by a poly-G tail. In one embodiment, the tail region 310 is a DNA-based poly-A tail that is 100 nucleotides in length. Nucleotides (dTTP's) are added under conditions that promote polynucleotide synthesis, and the nucleotides are incorporated to transcribe the tail region, thereby releasing hydrogen ions. If the minimum threshold number of hydrogen ions for the transistor to detect an electrical output signal is 100 nucleotides or less, a transistor will detect an electrical output signal. This signal is used to identify the target analyte associated with the poly-A tail region and potentially determine the concentration of the target analyte in the solution.

In some embodiments, the tail region 310 comprises a homopolymeric base region that includes one or more stop bases. FIG. 3 illustrates a single stop base 330 that is flanked by two homopolymeric base regions. A stop base 330 is a portion of a tail region 310 comprising at least one nucleotide adjacent to a homopolymeric base region, such that the at least one nucleotide is composed of a base that is distinct from the bases within the homopolymeric base region. In one embodiment, the stop base 330 is one nucleotide. In other embodiments, the stop base 330 comprises a plurality of nucleotides. Generally, the stop base 330 is flanked by two homopolymeric base regions. In an embodiment, the two homopolymeric base regions flanking a stop base 330 are composed of the same base. In another embodiment, the two homopolymeric base regions are composed of two different bases. In another embodiment, the tail region 310 contains more than one stop base 330.

Further details about aptamers and tail regions as probes for differential detection of small molecules is described in U.S. Provisional Application No. 61/868,988.

Molecular Tags

Figure 4:
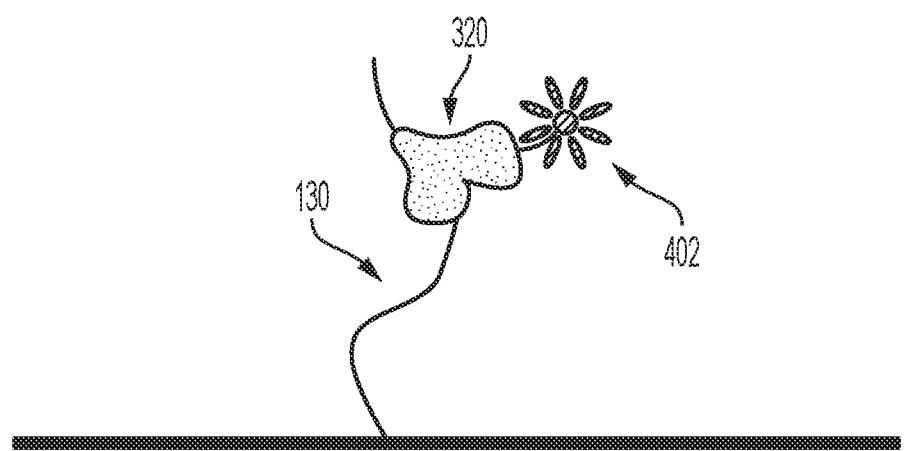
FIG. 4 shows a fluorescent tag attached to a probe comprising an aptamer and a tail region, according to one embodiment of the invention.

In some embodiments, the probe comprises a molecular tag for detection of the target analyte. Tags can be attached chemically or covalently to other regions of the probe. In some embodiments, the tags are fluorescent molecules. Fluorescent molecules can be fluorescent proteins or can be a reactive derivative of a fluorescent molecule known as a fluorophore. FIG. 4 illustrates a fluorescent tag 402 attached to a probe 320. Fluorophores are fluorescent chemical compounds that emit light upon light excitation. In some embodiments, the fluorophore selectively binds to a specific region or functional group on the target molecule and can be attached chemically or biologically. Examples of fluorescent tags include, but are not limited to, green fluorescent protein (GFP), yellow fluorescent protein (YFP), red fluorescent protein (RFP), cyan fluorescent protein (CFP), fluorescein, fluorescem isothiocyanate (FITC), tetramethylrhodamine isothiocyanate (TRITC), cyanine (Cy3), phycoerythrin (R-PE) 5,6-carboxymethyl fluorescein, (5-carboxyfluorescein-N-hydroxysuccinimide ester), Texas red, nitrobenz-2- oxa-1,3-diazol-4-yl (NBD), coumarin, dansyl chloride, and rhodamine (5,6-tetramethyl rhodamine).

Other exemplary fluorescent tags are listed below in Table 1B.

TABLE 1B

Fluorescent Tags

| | | mKeima-Red | Katushka (Turbo FP635) |
|---|---|---|---|
| Hydroxycoumarin | Cy7 | | |
| Aminocoumarin | DyLight 350 | TagCFP | mKate (TagFP635) |
| Methoxycoumarin | DyLight 405 | AmCyna1 | TurboFP635 |
| Cascade Blue | DyLight 488 | mTFP1 (Teal) | mPlum |
| Pacific Blue | DyLight 549 | 865A | mRaspberry |
| Pacific Orange | DyLight 594 | Midoriishi-Cyan | mNeptune |
| Lucifer yellow | DyLight 633 | Wild Type GFP | E2-Crimson |
| NBD | DyLight 649 | S65C | Monochlorobimane |
| R-Phycoerythrin (PE) | DyLight 680 | TurboGFP | Calcein |
| PE-Cy5 conjugates | DyLight 750 | TagGFP | HyPer |
| PE-Cy7 conjugates | DyLight 800 | TagGFP2 | |
| Red 613 | Hoechst 33342 | AcGFP1 | |
| PerCP | DAPI | S65L | |
| TruRed | Hoechst 33258 | Emerald | |
| FluorX | SYTOX Blue | S65T | |
| Fluorescein | Chromomycin A3 | EGFP | |
| BODIPY-FL | Mithramycin | Azami-Green | |
| TRITC | YOYO-1 | ZsGreen1 | |
| X-Rhodamine B | Ethidium Bromide | Dronpa-Green | |
| Lissamine | Acridine | Tag YFP | |
| Rhodamine B | Orange | | |
| Texas Red | SYTOX Green | EYFP | |
| Allophycocyanin (APC) | TOTO-1, TO-PRO-1 | Topaz | |
| APC-Cy7 conjugates | Thiazole Orange | Venus | |
| Alexa Fluor 350 | Propidium Iodide (PI) | mCitrine | |
| Alexa Fluor 405 | LDS 751 | YPet | |
| Alexa Fluor 430 | 7-AAD | TurboYFP | |
| Alexa Fluor 488 | SYTOX Orange | PhiYFP | |
| Alexa Fluor 500 | TOTO-3, To-Pro-3 | PhiYFP-m | |
| Alexa Fluor 514 | DRAQ5 | ZsYellow1 | |
| Alexa Fluor 532 | Indo-1 | mBanana | |
| Alexa Fluor 546 | Fluo-3 | Kusabira-Orange | |
| Alexa Fluor 555 | DCFH | mOrange | |
| Alexa Fluor 568 | DHR | mOrange2 | |
| Alexa Fluor 594 | SNARF | mKO | |
| Alexa Fluor 610 | Y66H | TurboRFP | |
| Alexa Fluor 633 | Y66F | tdTomato | |
| Alexa Fluor 647 | EBFP | DsRed-Express2 | |
| Alexa Fluor 660 | EBFP2 | TagRFP | |
| Alexa Fluor 680 | Azurite | DsRed monomer | |
| Alexa Fluor 700 | GFPuv | DsRed2 ("RFP") | |
| Alexa Fluor 750 | T-Sapphire | mStrawberry | |
| Alexa Fluor 790 | TagBFP | TurboFP602 | |
| Cy2 | Cerulean | AsRed2 | |
| Cy3 | mCFP | mRFP1 | |

Probes Including Antibodies and Oligonucleotides

Figure 5:
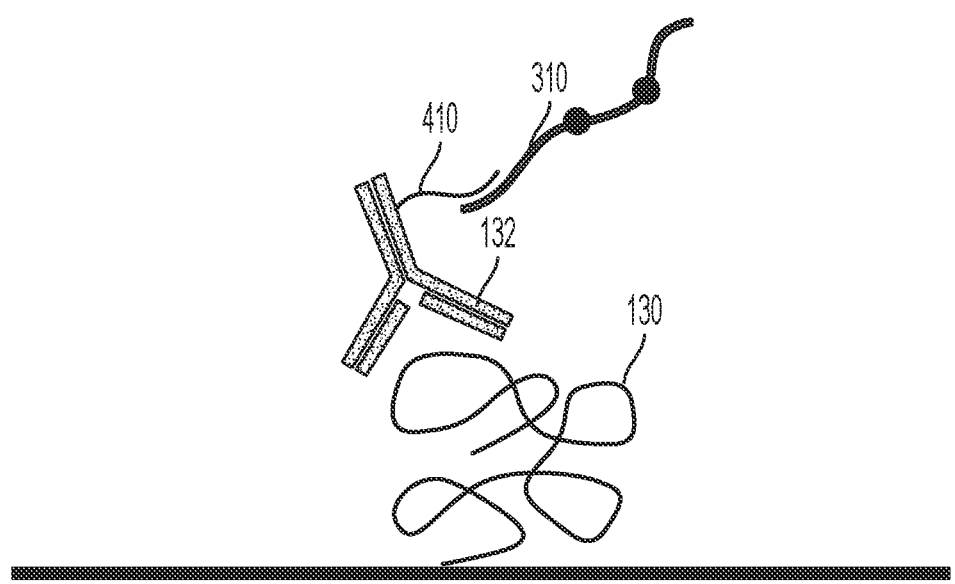
FIG. 5 shows an example of a probe comprising an antibody linked to a region that can hybridize to a tail region, according to one embodiment of the invention.

As shown in FIG. 5, the probe can comprise an antibody 132 linked to a region 410 that can hybridize to an oligonucleotide tail region 310. The oligonucleotide tail region 310 can be bound to the antibody 132 via a linking region 410, such as a polyethylene glycol (PEG) chain, ethylene oxide subunits, or other similar chains that can link the antibody 132 to the oligonucleotide tail 310. In some embodiments, the linking region can include an oligonucleotide that is linked to the antibody peptide using standard chemical methods such as, e.g., NHS ester-maleimide mediated conjugation chemistry where N-terminal Cys incorporated peptide reacts with a maleimide active ted oligo. In other embodiments, linking is accomplished through an internal Cys via oxime formation through a hydroxyl-amine modified peptide reaction with an aldehyde modified oligonucleotide. Such methods are known to the ordinarily skilled artisan. The oligonucleotide sequence in the linking region 410 can hybridize to a portion of the oligonucleotide tail region 310. The oligonucleotide tail region 310 can comprise an oligonucleotide sequence that is used as a template for polynucleotide synthesis and electrical detection, as described above. U.S. Pat. No. 7,122,319, filed on Nov. 5, 2003 to Liu et al. describes various embodiments for analyte binding agents (e.g., antibodies) linked to oligonucleotide tags, and is incorporated by reference in its entirety.

Figure 6:
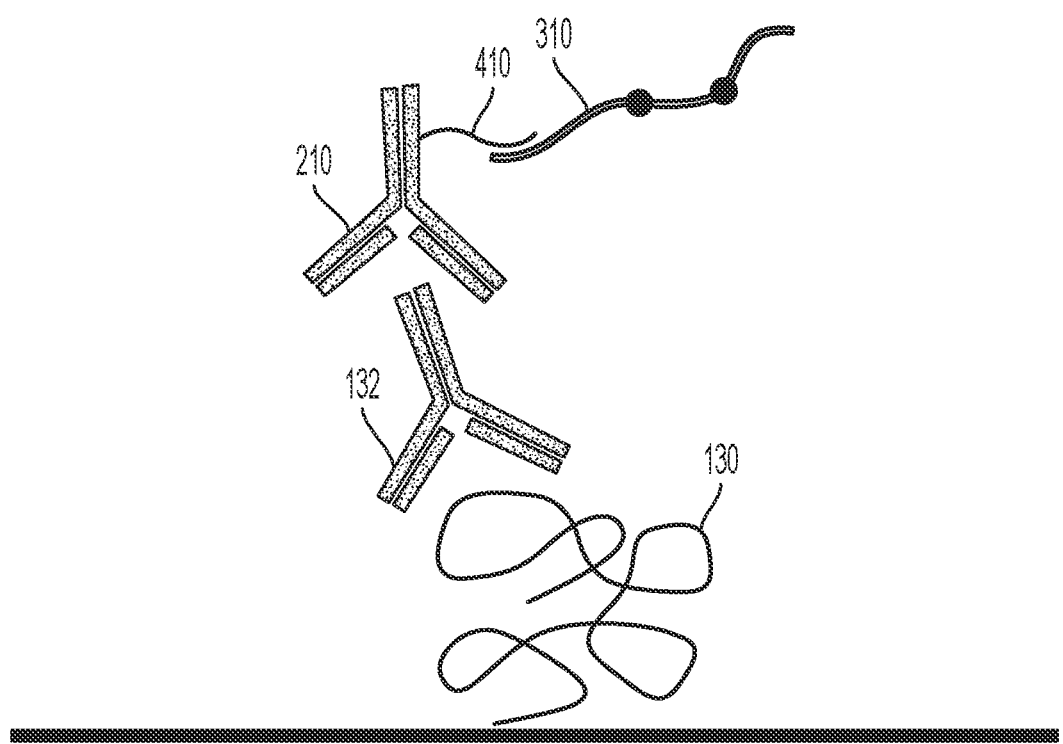
FIG. 6 illustrates an example of a probe comprising a primary antibody and a secondary antibody conjugated to a tail region, according to one embodiment of the invention.

As shown in FIG. 6, the probe comprises a primary antibody 132 and a secondary antibody 210. The primary antibody 132 binds the target analyte 130, and the secondary antibody 210 binds the primary antibody 132. The secondary antibody 210 is conjugated to a linker region 410 that hybridizes to an oligonucleotide tail region 310. The tail region 310 acts as a detectable tag in electrical detection of the target analyte 130.

3. Methods

I. Substrate and Sample Preparation

The present invention provides methods for identifying and quantifying a wide range of analytes, from a single analyte up to tens of thousands of analytes simultaneously over many orders of magnitude of dynamic range, while accounting for errors in the detection assay.

Figure 7:
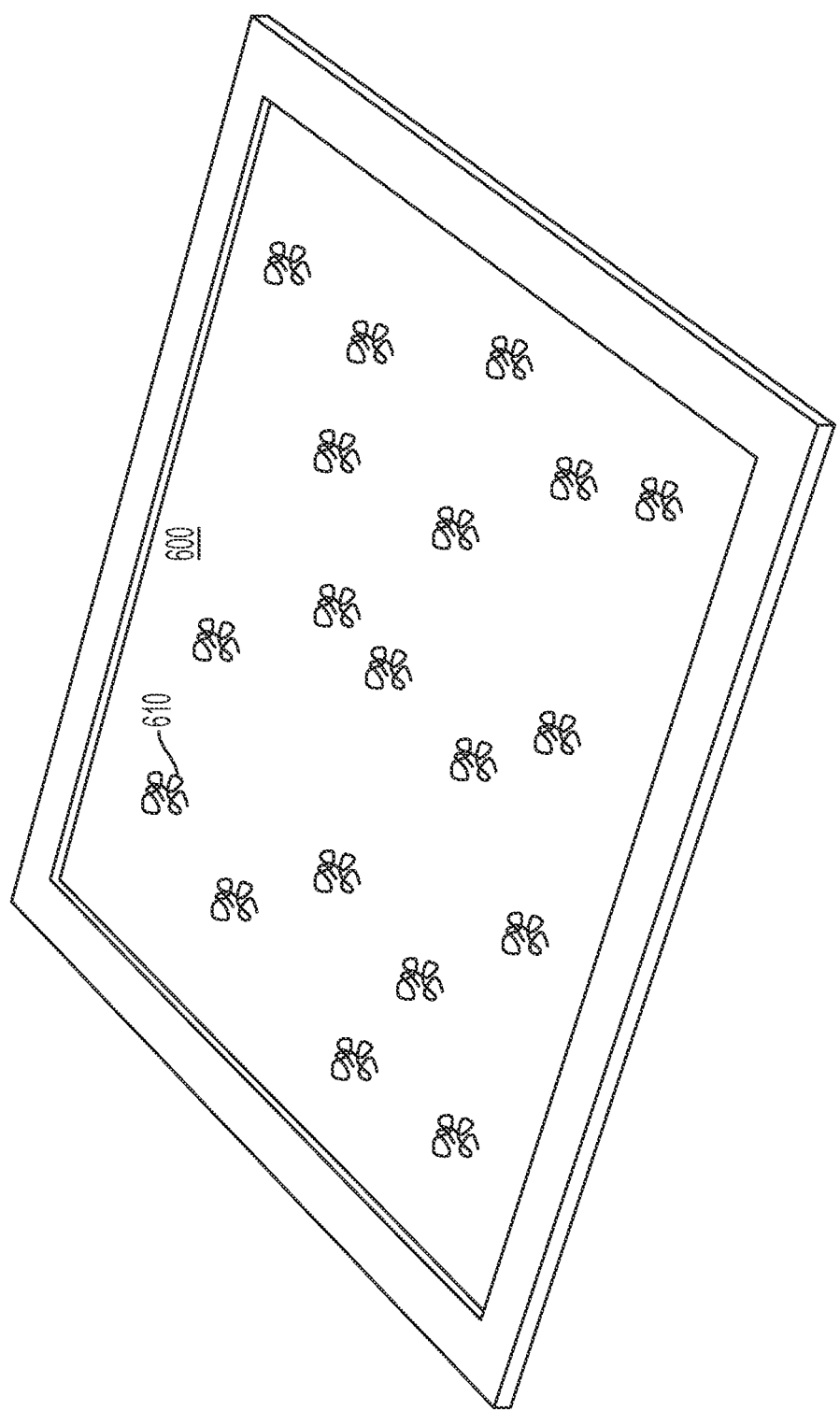
FIG. 7 shows an example of a solid substrate bound with a sample comprising analytes (e.g., proteins, DNA and/or RNA), according to one embodiment of the invention.

As shown in FIG. 7, a sample comprising analytes 610 (e.g., proteins, peptides, DNA and/or RNA) are bound to a solid substrate 600. The substrate 600 can comprise a glass slide, silicon surface, solid membrane, plate, or the like used as a surface for immobilizing the analytes 610. In one embodiment, the substrate 600 comprises a coating that binds the analytes 610 to the surface. In another embodiment, the substrate 600 comprises capture antibodies or beads for binding the analytes 610 to the surface. The analytes 610 can be bound randomly to the substrate 600 and can be spatially separated on the substrate 600. The sample can be in aqueous solution and washed over the substrate, such that the analytes 610 bind to the substrate 600. In one embodiment, the proteins in the sample are denatured and/or digested using enzymes before binding to the substrate 600. In some embodiments, the analytes 610 can be covalently attached to the substrate. In another embodiment, selected labeled probes are randomly bound to the solid substrate 600, and the analytes 610 are washed across the substrate.

Figure 8:
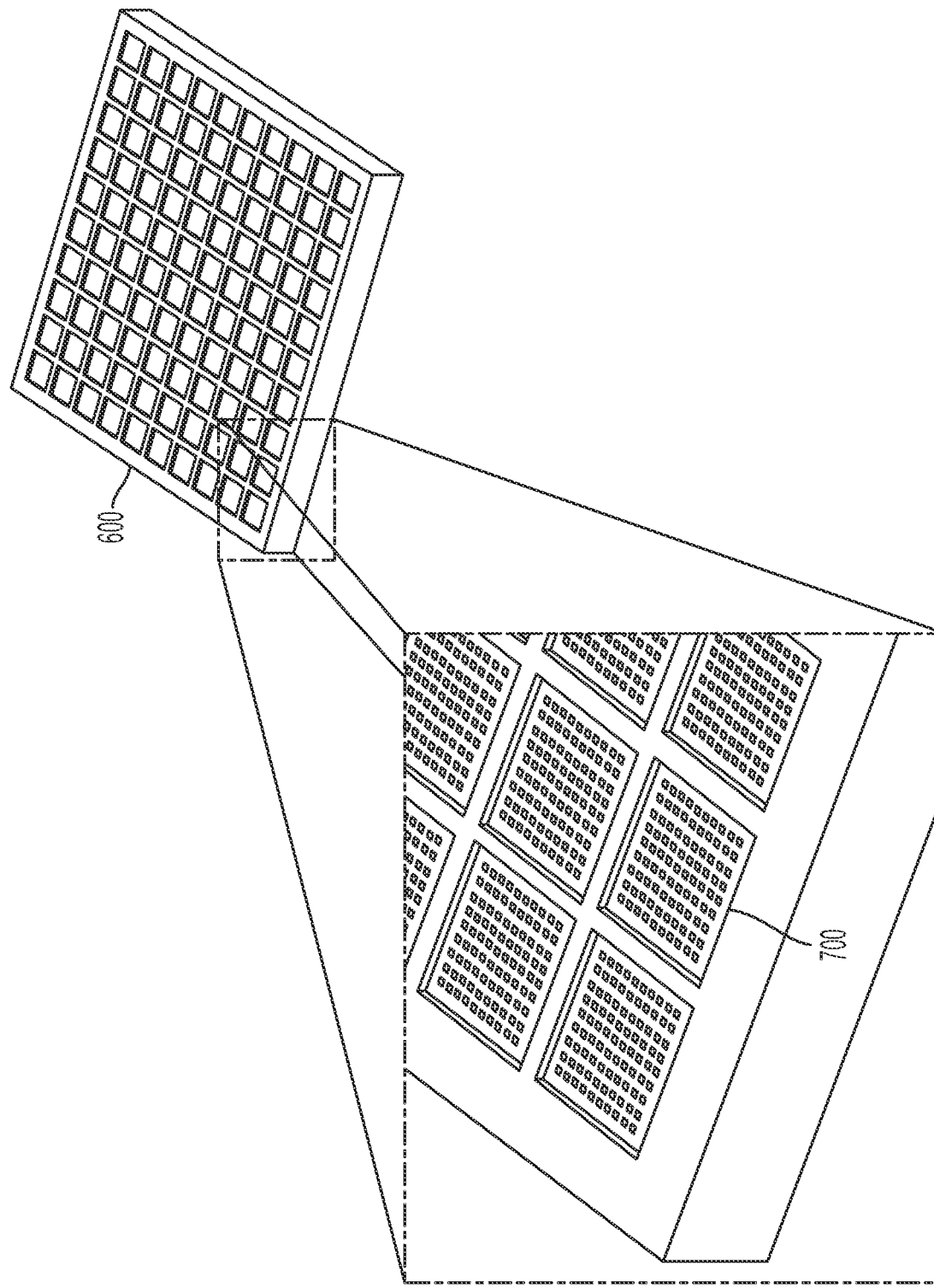
FIG. 8 shows an example substrate (10×10 array) for binding analytes, according to one embodiment of the invention.

FIG. 8 shows an example substrate 600 (10×10 array) for binding analytes 610, where each array insert 700 has 11×11 (110) target arrays.

Figure 9:
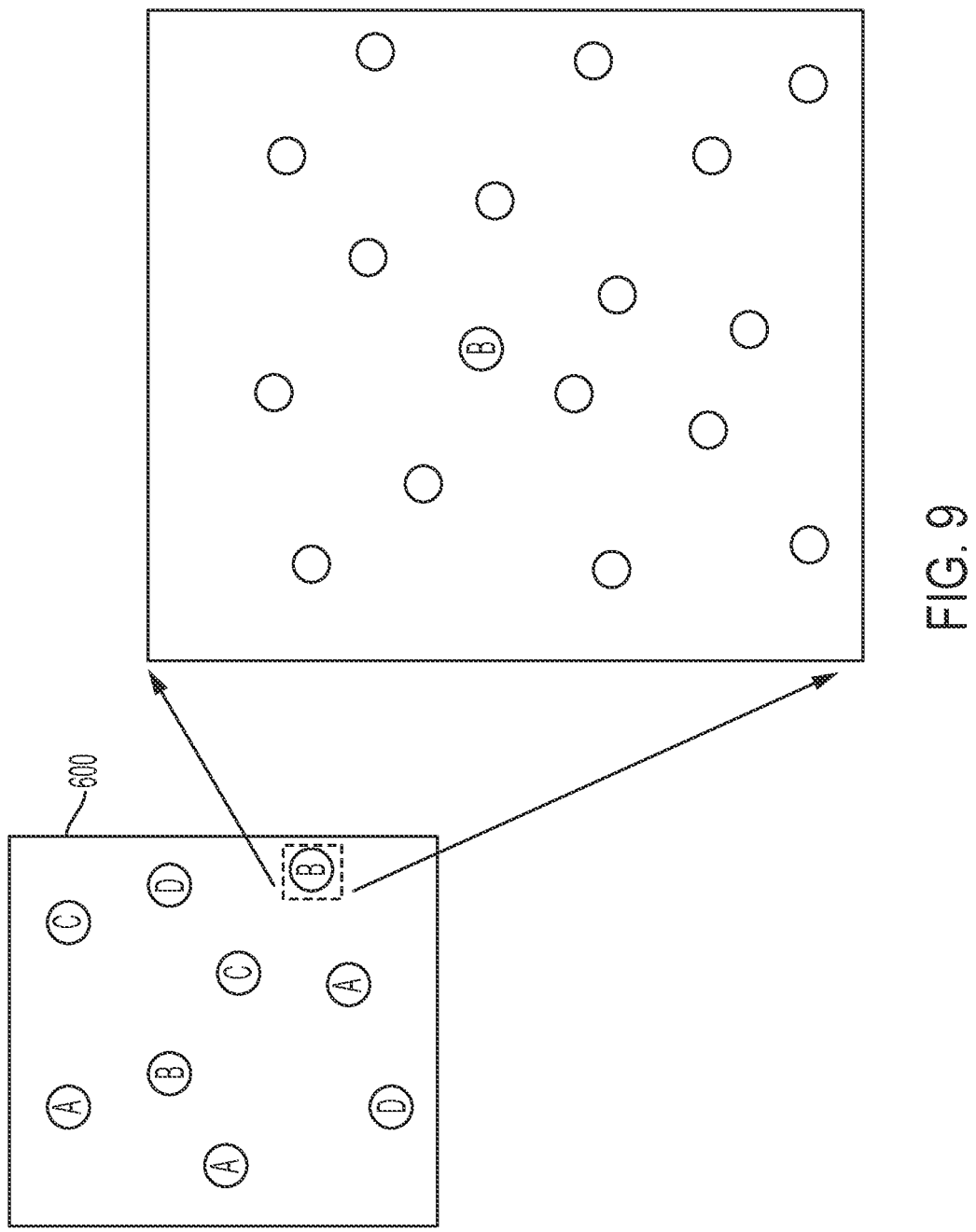
FIG. 9 is a top view of a solid substrate with analytes randomly bound to the substrate, according to one embodiment of the invention.

FIG. 9 is a top view of a solid substrate 600 with analytes randomly bound to the substrate 600. Different analytes are labeled as A, B, C, and D. For optical detection of the analytes, the imaging system requires that the analytes are spatially separated on the solid substrate 600, so that there is no overlap of fluorescent signals. For a random array, this means that multiple pixels will be needed for each fluorescent spot.

The number of pixels can be as few as 1 and as many as hundreds of pixels per spot. It is expected that the optimal of pixels per fluorescent spot is between 5 and 20 pixels. In one example, an imaging system has 224 nm pixels. For a system with 10 pixels per fluorescent spot on average, there is a surface density of 2 fluorescent pixels/$\mu m^2$ This does not mean that the protein surface density needs to be this low. If probes are only chosen for low abundance proteins, then the amount of protein on the surface may be much higher. For instance, if there are, on average, 20,000 proteins per $\mu m^2$ on the surface, and probes are chosen only for the rarest 0.01% (as an integrated sum) proteins, then the fluorescent protein surface density will be 2 fluorescent pixels/$\mu m^2$. In another embodiment, the imaging system has 163 nm pixels. In another embodiment, the imaging system has 224 nm pixels. In a preferred embodiment, the imaging system has 325 nm pixels. In other embodiments, the imaging system has as large as 500 nm pixels.

II. Optical Detection Methods

Optical detection methods can be used to quantify and identify a large number of analytes simultaneously in a sample.

In one embodiment, optical detection of fluorescently-tagged single molecules can be achieved by frequency-modulated absorption and laser-induced fluorescence. Fluorescence can be more sensitive because it is intrinsically amplified as each fluorophore emits thousands to perhaps a million photons before it is photo bleached. Fluorescence emission usually occurs in a four-step cycle: 1) electronic transition from the ground-electronic state to an excited-electronic state, the rate of which is a linear function of excitation power, b) internal relaxation in the excitedelectronic state, c) radiative or non-radiative decay from the excited state to the ground state as determined by the excited state lifetime, and d) internal relaxation in the ground state. Single molecule fluorescence measurements are considered digital in nature because the measurement relies on a signal/no signal readout independent of the intensity of the signal.

Optical detection requires an optical detection instrument or reader to detect the signal from the labeled probes. U.S. Pat. Nos. 8,428,454 and 8,175,452, which are incorporated by reference in their entireties, describe exemplary imaging systems that can be used and methods to improve the systems to achieve sub-pixel alignment tolerances. In some embodiments, methods of aptamerbased microarray technology can be used. See Optimization of Aptamer Microarray Technology for Multiple Protein Targets, *Analytica Chimica Acta* 564 (2006).

A. Optical Detection of Multiple Analytes Using Tagged Antibodies

The method includes optical detection of analytes using tagged antibodies as probes. For a known target analyte (protein) in the sample, an antibody is selected that specifically binds to the target analyte. Selected antibodies can be those developed for ELISA and comparable systems as single molecule probes. There are hundreds to thousands of existing and qualified primary and secondary antibodies that are readily available. In some embodiments, primary antibodies are selected that are conjugated to a tag, such as a fluorophore. In other embodiments, primary antibodies are selected that bind to secondary antibodies, and the secondary antibodies are conjugated to a fluorescent molecule.

In one embodiment, the method includes selecting a primary antibody that has a known, specific target protein in the sample. The primary antibody is tagged with a detectable tag, such as a fluorescent molecule. The selected primary antibodies are introduced and washed across the substrate. The primary antibodies bind to their target analytes, and signals from the tags are detected.

In another embodiment, a primary antibody and a secondary antibody conjugated to a detectable tag are selected. The selected primary antibodies are introduced and washed across the substrate. The primary antibodies bind to their target analytes. Next, secondary antibodies are washed across the substrate and bind to the primary antibodies. The tags produce a detectable signal, and the signals are detected and analyzed, preferably using a computer, to determine whether a signal is detected at a defined location, and in some embodiments additional information about the nature of the signal (e.g., the color of the label).

A pass comprises a binding step and a signal detection step. There can be a number of passes per cycle, where each pass includes binding of a set of tagged antibodies to a different target protein and detection and analysis of signals from the tagged antibodies. There can be multiple passes of different tagged antibodies before the substrate is stripped of all tagged antibodies. A cycle concludes when one or more passes are completed, and the tagged antibodies are stripped from the substrate. Subsequent cycles of one or more passes per cycle can be performed with the same substrate and sample of bound analytes.

An optical detection instrument or reader is used to optically detect each of the signals from the labeled antibodies. The number of signals, location of the signal, and presence or absence of the signal can be recorded and stored. Details about the quantification and identification of the analytes based on the detected optical signals are described below.

1. Multiple Tans for Multiple Analytes

In one embodiment, a plurality of antibodies conjugated to fluorescent tags is used to detect individual proteins bound to a substrate. Each distinct type of protein is tagged with a limited number of fluorescent tags. For example, in a single pass, antibodies are introduced that are tagged with a red fluorescent tag and selectively bind to protein A. The number of red fluors on the substrate is counted after binding. The number of tags counted is proportional to the concentration of protein A.

Each subsequent pass introduces a different fluorescent tag (different color) for detecting a different protein (e.g., blue fluorescent tag for protein B, yellow fluorescent tag for protein C, etc.). The presence of each fluorescent tag is counted at each pass and recorded. FIG. 9 illustrates a solid substrate comprising analytes A, B, C, and D. At each pass, a different analyte can be detected with a different fluorescent tag and counted accordingly.

Figure 13:
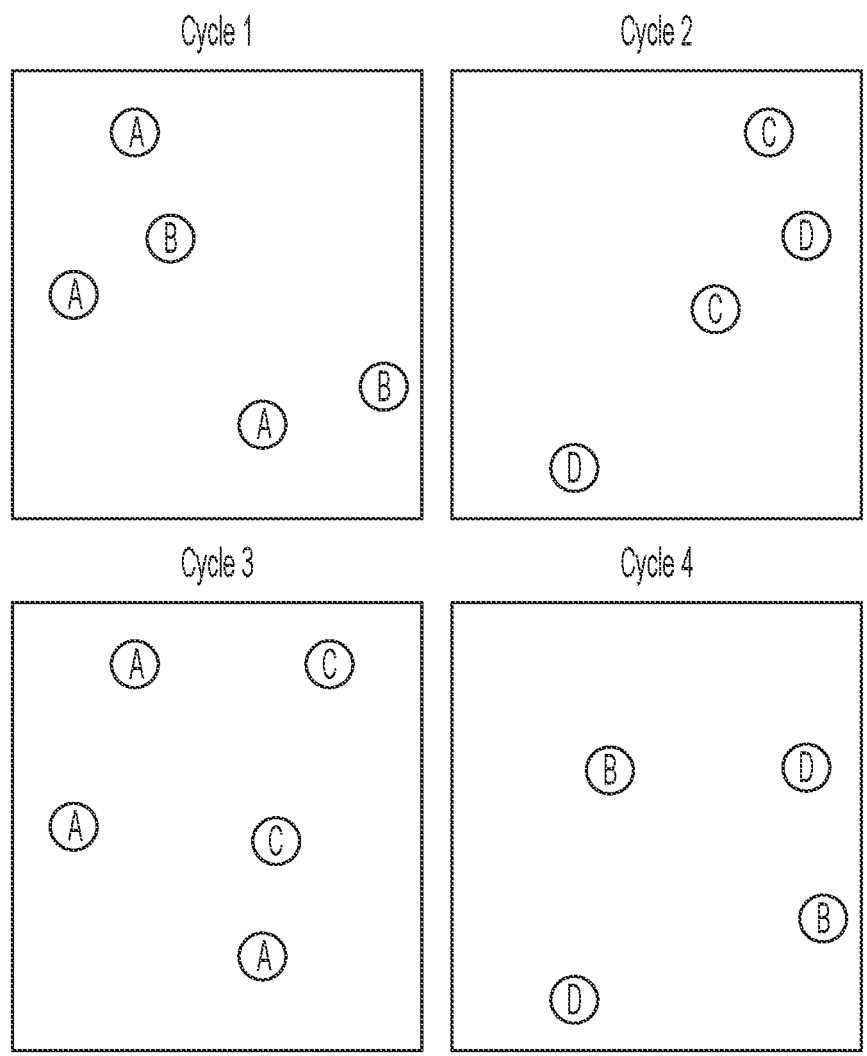
FIG. 13 illustrates an example detection assay using a substrate and four analytes using a single color fluorescent tag, single pass, dark counted, and 1 bit per cycle, according to one embodiment of the invention.

In some embodiments, a "dark level" is used in the detection and analysis of the analyte. A dark level exists where there is no tag present in the pass and no positive signal is counted, which is referred to as a "dark pass." The absence of any signal is considered to be a level (i.e., dark cycle counted). Incorporating a dark level allows the number of probes per cycle to be reduced by one. In some embodiments, it is preferred to have a positive signal and not use a dark level because the use of dark levels can be more susceptible to errors. One example embodiment is shown in FIG. 13. In other embodiments, where the raw system error rate is low and the number of probes per cycle is low, the use of a dark level can significantly increase the amount of information transferred per cycle.

A specific case in which the use of a dark level is helpful is where a primary antibody probe is hybridized to an analyte bound to a substrate, and in which a fluorescently or electrically tagged secondary antibody is bound to the first antibody. The secondary antibody can bind non-specifically to all antibodies so that only one level of information is possible per cycle for a single pass system. In this case, the use of a dark level (i.e., not including a primary antibody in the cycle) is required to achieve 1 bit of information per cycle.

To eliminate the use of a dark level when using secondary antibodies, either the use of two or more types o secondary antibodies which have high affinities to a predetermined set of probes of primary antibodies and have low affinities to other predetermined sets of probes of primary antibodies or at least two passes per cycle are required.

2. Single Tag for Multiple Analytes

Figure 14:
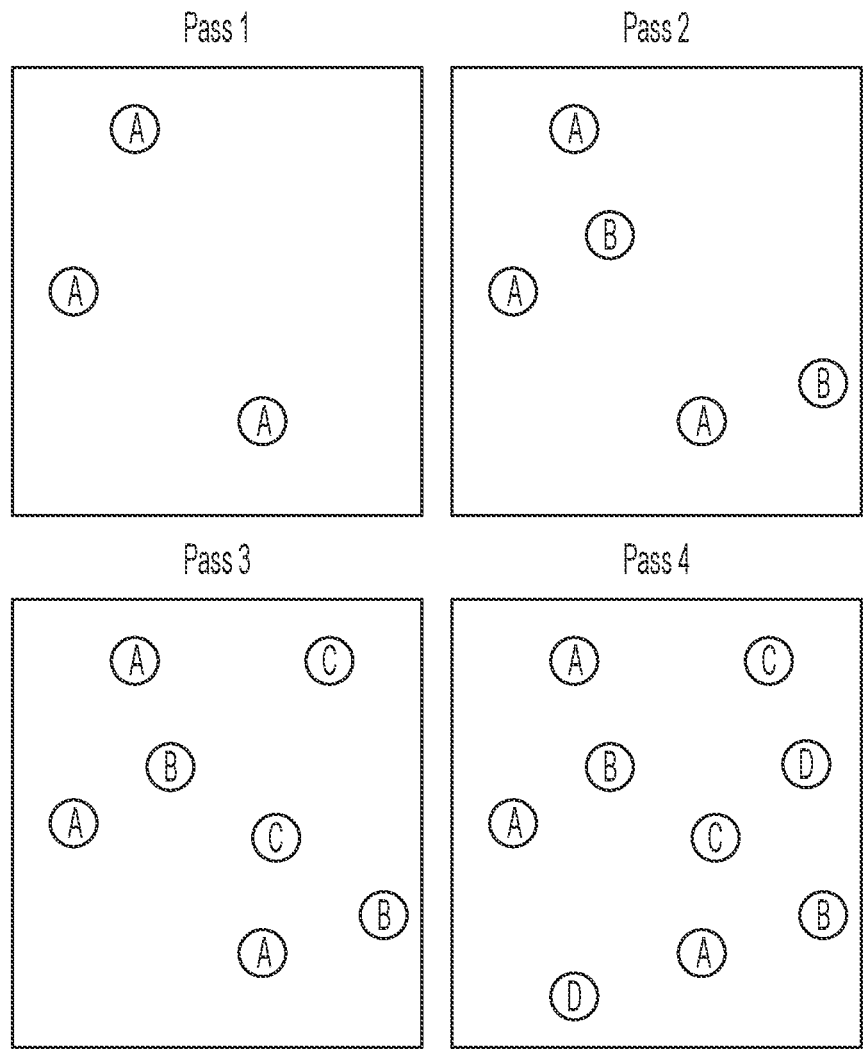
FIG. 14 shows an example detection assay using a substrate and four analytes using a single color fluorescent tag, four passes per cycle, dark cycle not counted, and 2 bits per cycle, according to one embodiment of the invention.

In another embodiment, a plurality of antibodies conjugated to fluorescent tags is used to detect individual proteins bound to a substrate. Each type of protein can be tagged with the same fluorescent tag (same color). For example, in one pass, antibody probes tagged with a red fluorescent tag selectively bind to protein A, and the number of red fluors on the substrate is counted. On a second pass, antibody probes tagged with a red fluorescent molecule that specifically bind to protein B are introduced, and the presence of the additional red fluorescent tags at additional locations on the substrate is counted and recorded. Multiple passes can be performed using antibodies labeled with the same fluorescent label that specifically bind different target proteins. The presence of additional red fluorescent tags detected on the substrate at each pass are counted and recorded. One example embodiment is shown in FIG. 14.

B. Methods for Optical Detection of Analytes

The high dynamic-range analyte quantification methods of the invention allow the measurement of over 10,000 analytes from a biological sample. The method can quantify analytes with concentrations from about 1 ag/mL to about 50 mg/mL and produce a dynamic range of more than $10^{10}$. The optical signals are digitized, and analytes are identified based on a code (ID code) of digital signals for each analyte.

As described above, analytes are bound to a solid substrate, and probes are bound to the analytes. Each of the probes comprises tags and specifically binds to a target analyte. In some embodiments, the tags are fluorescent molecules that emit the same fluorescent color, and the signals for additional fluors are detected at each subsequent pass. During a pass, a set of probes comprising tags are contacted with the substrate allowing them to bind to their targets. An image of the substrate is captured, and the detectable signals are analyzed from the image obtained after each pass. The information about the presence and/or absence of detectable signals is recorded for each detected position (e.g., target analyte) on the substrate.

In some embodiments, the invention comprises methods that include steps for detecting optical signals emitted from the probes comprising tags, counting the signals emitted during multiple passes and/or multiple cycles at various positions on the substrate, and analyzing the signals as digital information using a K-bit based calculation to identify each target analyte on the substrate. Error correction can be used to account for errors in the optically-detected signals, as described below.

In some embodiments, a substrate is bound with analytes comprising N target analytes. To detect N target analytes, M cycles of probe binding and signal detection are chosen. Each of the M cycles includes 1 or more passes, and each pass includes N sets of probes, such that each set of probes specifically binds to one of the N target analytes. In certain embodiments, there are N sets of probes for the N target analytes.

In each cycle, there is a predetermined order for introducing the sets of probes for each pass. In some embodiments, the predetermined order for the sets of probes is a randomized order. In other embodiments, the predetermined order for the sets of probes is a non-randomized order. In one embodiment, the non-random order can be chosen by a computer processor. The predetermined order is represented in a key for each target analyte. A key is generated that includes the order of the sets of probes, and the order of the probes is digitized in a code to identify each of the target analytes.

In some embodiments, each set of ordered probes is associated with a distinct tag for detecting the target analyte, and the number of distinct tags is less than the number of N target analytes. In that case, each N target analyte is matched with a sequence of M tags for the M cycles. The ordered sequence of tags is associated with the target analyte as an identifying code.

In one example, there are 16 target proteins and 16 distinct probes for each of the target proteins, but only four fluorescent tags (red, blue, green, and yellow). FIG. 10A illustrates an example of the 16 target proteins (labeled P1, P2, P3, etc.) arranged on a substrate. The assay can be set up with two cycles and one pass per cycle. Accordingly, two ordered sets of pools are created (one ordered set per cycle). Each probe pool uses the four tags to label the 16 target proteins in a unique 2-color sequence.

Figure 10D:
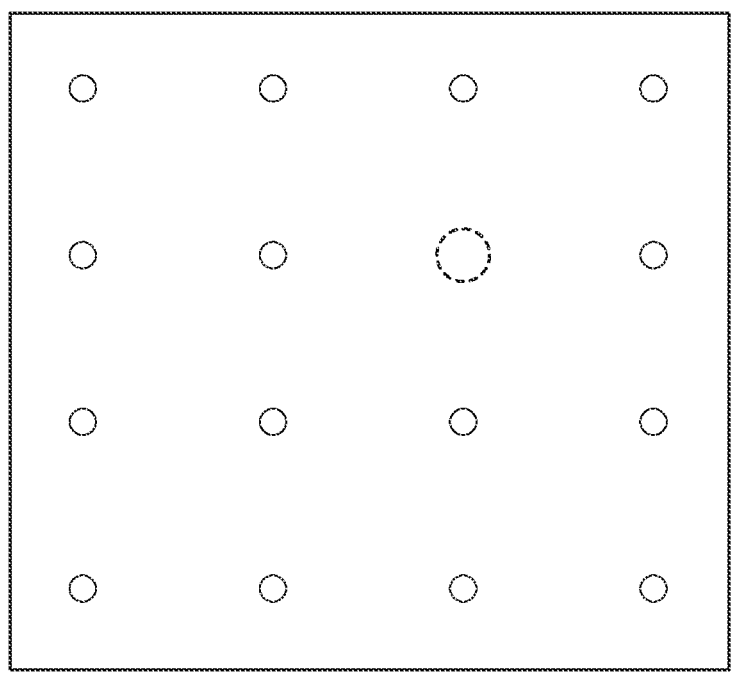

Table 2 below shows the 16 target analytes and corresponding probe numbers. Table 3 shows the four fluorescent tags (labeled 0 through 3). Tables 4 and 5 show two probe pools where each of the 16 target analytes are labeled with a first fluorescent tag in probe pool 1 and a second fluorescent tag in probe pool 2. FIG. 10B illustrates the substrate of FIG. 10A that has been contacted with probe pool 1. FIG. 10C illustrates the substrate of FIG. 10A that has been contacted with probe pool 2. For example, Probe A2 is tagged with a blue fluorescent tag in probe pool 1, and a red fluorescent tag in probe pool 2. Accordingly, in cycle 1, probe A2 (bound to analyte P2) will emit a blue color, and in cycle 2, probe A2 will emit a red color. In another example, illustrated by FIG. 10D, probe A7 has a green (GRN) tag in probe pool 1 (or cycle number 1). In probe pool 2, probe A 7 has a blue (BLU) tag. In each probe pool, several probes share the same tag color, but the sequence of colors across the two pools is unique for each analyte. In probe pool #1, for example, probes A4 and A8 are both tagged yellow. Only probe A9, however, is tagged red in probe pool #1 and green in probe pool #2.

TABLE 2

Analyte and Probe

| Analyte Number | Probe Number |
|---|---|
| P1 | A1 |
| P2 | A2 |
| P3 | A3 |
| P4 | A4 |
| P5 | A5 |
| P6 | A6 |
| P7 | A7 |
| P8 | A8 |
| P9 | A9 |
| P10 | A10 |
| P11 | A11 |
| P12 | A12 |
| P13 | A13 |
| P14 | A14 |
| P15 | A15 |
| P16 | A16 |

TABLE 3

Tag Number and Color

| Tag Number | Tag | Color |
|---|---|---|
| 0 | Red | RED |
| 1 | Blue | BLU |
| 2 | Green | GRN |
| 3 | Yellow | YLW |

TABLE 4

Probe Pool 1
Probe Pool #1

| Probe Number | Tag Color |
|---|---|
| A1 | RED |
| A2 | BLU |
| A3 | GRN |

TABLE 4-continued

Probe Pool 1
Probe Pool #1

| Probe Number | Tag Color |
|---|---|
| A4 | YLW |
| A5 | RED |
| A6 | BLU |
| A7 | GRN |
| A8 | YLW |
| A9 | RED |
| A10 | BLU |
| A11 | GRN |
| A12 | YLW |
| A13 | RED |
| A14 | BLU |
| A15 | GRN |
| A16 | YLW |

TABLE 5

Probe Pool 2
Probe Pool #2

| Probe Number | Tag Color |
|---|---|
| A1 | RED |
| A2 | RED |
| A3 | RED |
| A4 | RED |
| A5 | BLU |
| A6 | BLU |
| A7 | BLU |
| A8 | BLU |
| A9 | GRN |
| A10 | GRN |
| A11 | GRN |
| A12 | GRN |
| A13 | YLW |
| A14 | YLW |
| A15 | YLW |
| A16 | YLW |

Table 6 shows an example of a key comprising an ID (identification) code for each target analyte based on color sequence. The table shows N protein targets by name, a corresponding base-10 number (1 to 10,000), a base-M number (e.g., base 4 with 7 digits shown here), and a color sequence. The color sequence is the order and type of detected signal (red, blue, green, yellow) that was emitted for a particular analyte. The key provides a corresponding base-M number (e.g., base 4, 7 digits) and the identity of the target analyte that corresponds with each color sequence. Accordingly, the base-4 calculation allows for an ordered color sequence of 7 signals, and identification of over 10,000 different target analytes, each having its own identifying color sequence.

TABLE 6

Key of protein targets by name, base-10 number, base-M number and color sequence

| Target list by name | Target list by base-10 number | Target list by base-M number | Target list by color sequence |
|---|---|---|---|
| Alpha-1-acid Glycoprotein | 1 | 0000001 | RRRRRRB |
| Apolipoprotein B | 2 | 0000002 | RRRRRRG |
| Myoglobin | 3 | 0000003 | RRRRRRY |

TABLE 6-continued

Key of protein targets by name, base-10 number,
base-M number and color sequence

| Target list by name | Target list by base-10 number | Target list by base-M number | Target list by color sequence |
|---|---|---|---|
| L-Selectin | 6,751 | 1221133 | BGGBBYY |
| MMP9 | 9,999 | 2130033 | GBYRRYY |
| Troponin T | 10,000 | 2130100 | GBYRBRR |

In one embodiment, the method includes the following steps for labeling probe pools to count N different kinds of target analytes on a substrate using fluorescently tagged probes of X different colors:

1. Number a list of the N targets (or their probes) using base-X numbers.
2. Associate fluorescent tags with base-X digits from 0 to X-1. (For example, 0, 1, 2, 3 correspond to red, blue, green, yellow.)
3. Find C such that $X^c > N$.
4. At least C probe pools are needed to identify the N targets. Label the C probe pools by an index k=1 to C.
5. In the $k^{th}$ probe pool, label each probe with a fluorescent tag of the color that corresponds to the $k^{th}$ base-X digit of the base-X number that identifies the probe's target in the list created in Step 1.

For example, if one has N=10,000 target analytes and four fluorescent tags, a base 4 can be chosen. The 4 fluorescent tag colors designated with the numbers 0, 1, 2, and 3, respectively. For example, numbers 0, 1, 2, 3 correspond to red, blue, green, and yellow.

When base 4 is chosen, each fluorescent color is represented by 2 bits (0 and 1, where 0=no signal and 1=signal present), and there are 7 colors that are used as a code to identify a target analyte. For example, protein A may be identified with the code of "1221133" that represents the color combination and order of "blue, green, green, blue, blue, yellow, yellow." For the 7 possible colors, there are a total of 14 bits of information for the target analyte (7×2=14 bits).

Next, C is chosen such that $4^7 > 10,000$. In this case, C can be 7 such that there are 7 probe pools to identify 10,000 targets ($4^7 = 16,384$, which is greater than 10,000). A color sequence of length C means that C different probe pools must be constructed. The 7 probe pools are labeled from k=1 to 7. Then each probe is labeled with a fluorescent tag that corresponds to the kth base and X-digit. For example, the third probe in the code "1221133" will be the $3^{rd}$ base-$4^{th}$ digit and corresponds to green.

C. Quantification of Optically-Detected Probes

After the detection process, the signals from each probe pool are counted, and the presence or absence of a signal and the color of the signal can be recorded for each position on the substrate.

From the detectable signals, K bits of information are obtained in each of M cycles for the N distinct target analytes. The K bits of information are used to determine L total bits of information, such that K×M=L bits of information and L≥$\log_2$ (N). The L bits of information are used to determine the identity (and presence) of N distinct target analytes. If only one cycle (M=1) is performed, then K×1=L. However, multiple cycles (M>1) can be performed to generate more total bits of information L per analyte. Each subsequent cycle provides additional optical signal information that is used to identify the target analyte.

In practice, errors in the signals occur, and this confounds the accuracy of the identification of target analytes. For instance, probes may bind the wrong targets (e.g., false positives) or fail to bind the correct targets (e.g., false negatives). Methods are provided, as described below, to account for errors in optical and electrical signal detection.

III. Electrical Detection Methods

In other embodiments, electrical detection methods are used to detect the presence of target analytes on a substrate. Target analytes are tagged with oligonucleotide tail regions and the oligonucleotide tags are detected using ionsensitive field-effect transistors (ISFET, or a pH sensor), which measures hydrogen ion concentrations in solution. ISFETs are described in further detail in U.S. Pat. No. 7,948,015, filed on Dec. 14, 2007, to Rothberg et al., and U.S. Publication No. 2010/0301398, filed on May 29, 2009, to Rothberg et al., which are both incorporated by reference in their entireties.

ISFETs present a sensitive and specific electrical detection system for the identification and characterization of analytes. In one embodiment, the electrical detection methods disclosed herein are carried out by a computer (e.g., a processor). The ionic concentration of a solution can be converted to a logarithmic electrical potential by an electrode of an ISFET, and the electrical output signal can be detected and measured.

ISFETs have previously been used to facilitate DNA sequencing. During the enzymatic conversion of single-stranded DNA into double-stranded DNA, hydrogen ions are released as each nucleotide is added to the DNA molecule. An ISFET detects these released hydrogen ions and can determine when a nucleotide has been added to the DNA molecule. By synchronizing the incorporation of the nucleoside triphosphate (dATP, dCTP, dGTP, and dTTP), the DNA sequence may also be determined. For example, if no electrical output signal is detected when the single-stranded DNA template is exposed to dATP's, but an electrical output signal is detected in the presence of dGTP's, the DNA sequence is composed of a complementary cytosine base at the position in question.

In one embodiment, an ISFET is used to detect a tail region of a probe and then identify corresponding target analyte. For example, a target analyte can be immobilized on a substrate, such as an integrated-circuit chip that contains one or more ISFETs. When the corresponding probe (e.g., aptamer and tail region) is added and specifically binds to the target analyte, nucleotides and enzymes (polymerase) are added for transcription of the tail region. The ISFET detects the release hydrogen ions as electrical output signals and measures the change in ion concentration when the dNTP's are incorporated into the tail region. The amount of hydrogen ions released corresponds to the lengths and stops of the tail region, and this information about the tail regions can be used to differentiate among various tags.

The simplest type of tail region is one composed entirely of one homopolymeric base region. In this case, there are four possible tail regions: a poly-A tail, a poly-C tail, a poly-G tail, and a poly-T tail. However, it is often desirable to have a great diversity in tail regions.

One method of generating diversity in tail regions is by providing stop bases within a homopolymeric base region of a tail region. A stop base is a portion of a tail region comprising at least one nucleotide adjacent to a homopolymeric base region, such that the at least one nucleotide is composed of a base that is distinct from the bases within the homopolymeric base region. In one embodiment, the stop base is one nucleotide. In other embodiments, the stop base comprises a plurality of nucleotides. Generally, the stop base is flanked by two homopolymeric base regions. In an embodiment, the two homopolymeric base regions flanking a stop base are composed of the same base. In another embodiment, the two homopolymeric base regions are composed of two different bases. In another embodiment, the tail region contains more than one stop base.

In one example, an ISFET can detect a minimum threshold number of 100 hydrogen ions. Target Analyte 1 is bound to a composition with a tail region composed of a 100-nucleotide poly-A tail, followed by one cytosine base, followed by another 100-nucleotide poly-A tail, for a tail region length total of 201 nucleotides. Target Analyte 2 is bound to a composition with a tail region composed of a 200-nucleotide poly-A tail. Upon the addition of dTTP's and under conditions conducive to polynucleotide synthesis, synthesis on the tail region associated with Target Analyte 1 will release 100 hydrogen ions, which can be distinguished from polynucleotide synthesis on the tail region associated with Target Analyte 2, which will release 200 hydrogen ions. The ISFET will detect a different electrical output signal for each tail region. Furthermore, if dGTP's are added, followed by more dTTP's, the tail region associated with TargetAnalyte 1 will then release one, then 100 more hydrogen ions due to further polynucleotide synthesis. The distinct electrical output signals generated from the addition of specific nucleoside triphosphates based on tail region compositions allow the ISFET to detect hydrogen ions from each of the tail regions, and that information can be used to identify the tail regions and their corresponding target analytes.

Various lengths of the homopolymeric base regions, stop bases, and combinations thereof can be used to uniquely tag each analyte in a sample. Additional description about electrical detection of aptamers and tail regions to identify target analytes in a substrate are described in U.S. Provisional Application No. 61/868,988, which is incorporated by reference in its entirety.

In other embodiments, antibodies are used as probes in the electrical detection method described above. The antibodies may be primary or secondary antibodies that bind via a linker region to an oligonucleotide tail region that acts as tag. Examples of such probes are shown in FIGS. 2, 5 and 6.

These electrical detection methods can be used for the simultaneous detection of hundreds (or even thousands) of distinct target analytes. Each target analyte can be associated with a digital identifier, such that the number of distinct digital identifiers is proportional to the number of distinct target analytes in a sample. The identifier may be represented by a number of bits of digital information and is encoded within an ordered tail region set. Each tail region in an ordered tail region set is sequentially made to specifically bind a linker region of a probe region that is specifically bound to the target analyte. Alternatively, if the tail regions are covalently bonded to their corresponding probe regions, each tail region in an ordered tail region set is sequentially made to specifically bind a target analyte.

In one embodiment, one cycle is represented by a binding and stripping of a tail region to a linker region, such that polynucleotide synthesis occurs and releases hydrogen ions, which are detected as an electrical output signal. Thus, number of cycles for the identification of a target analyte is equal to the number of tail regions in an ordered tail region set. The number of tail regions in an ordered tail region set is dependent on the number of target analytes to be identified, as well as the total number of bits of information to be generated. In another embodiment, one cycle is represented by a tail region covalently bonded to a probe region specifically binding and being stripped from the target analyte.

The electrical output signal detected from each cycle is digitized into bits of information, so that after all cycles have been performed to bind each tail region to its corresponding linker region, the total bits of obtained digital information can be used to identify and characterize the target analyte in question. The total number of bits is dependent on a number of identification bits for identification of the target analyte, plus a number of bits for error correction. The number of bits for error correction is selected based on the desired robustness and accuracy of the electrical output signal. Generally, the number of error correction bits will be 2 or 3 times the number of identification bits.

IV. Decoding the Order and Identity of Detected Analytes

The probes used to detect the analytes are introduced to the substrate in an ordered manner in each cycle. A key is generated that encodes information about the order of the probes for each target analyte. The signals detected for each analyte can be digitized into bits of information. The order of the signals provides a code for identifying each analyte, which can be encoded in bits of information.

In one example for optical detection of analytes, using 1-bit of information, each analyte is associated with an ordered set of probes. Table 7 below illustrates that each target analyte is associated with a predetermined order of a set of probes introduced over 7 cycles, and the order of the signals emitted from the ordered set of probes is used as a code for identifying the target analyte. For example, for alpha-1-acid glycoprotein, the identifying code is an ordered set of probes of six red (R) signals followed by a final blue (B) signal. When a set of signals is received for a target analyte that reads "RRRRRRB," the key is used to find a match between the identifying code of an order for the probes and the obtained signals from the analyte. Accordingly, the code is used to determine that the target analyte is alpha-1-acid glycoprotein.

TABLE 7

Key For Target Analytes Based On An Ordered Set Of Probes Over 7 Cycles and Corresponding Identifying Code

| Target Analyte | Cycles 1 2 3 4 5 6 7 | Signal | Code |
|---|---|---|---|
| Alpha-1-acid Glycoprotein | R R R R R R B | RRRRRRB | 0000001 |
| Apolipoprotein B | R R R R R R G | RRRRRRG | 0000002 |

TABLE 7-continued

Key For Target Analytes Based On An Ordered
Set Of Probes Over 7 Cycles and
Corresponding Identifying Code

| Target Analyte | Cycles 1 2 3 4 5 6 7 | Signal | Code |
|---|---|---|---|
| Myoglobin | R R R R R R Y | RRRRRRY | 0000003 |
| L-Selectin | B G G B B Y Y | BGGBBYY | 1221133 |

In some embodiments, the user of a kit comprising the ordered set of probes and instructions for using the probe does not have access to the code, such that he or she cannot match the ordered set of signals to the corresponding target analyte. In one embodiment, the kit does not include the key for decoding the results, and the user sends the data to a third party for processing of the data using the code. In another embodiment, the key with ID codes is provided to a user of the kit, and the user can decipher the ordered set of signals to the target analyte.

In a second example, each color (fluorescent signal) can be represented by a 2-bit sequence, and a 2-color sequence can be represented by a 4-bit data symbol. Table 8 provides an example of four colors (red, blue, green and yellow) and their corresponding bit values. For example, a color sequence "BGGBBYY" for a particular analyte may be encoded in 14 bits as 01101001011111 according to the bit scheme shown in Table 8.

TABLE 8

2-Bit Assignments for Fluorescent Labels

| Color | Bits |
|---|---|
| R | 00 |
| B | 01 |
| G | 10 |
| Y | 11 |

The order of the probes can be different for each analyte for each new cycle (when a cycle includes multiple passes) or for each set of cycles. The key used to identify an analyte in one set of cycles does not have to be used again in a second assay. The codes for the target analytes can be altered for each assay.

In some embodiments, the predetermined order of the ordered set of probes is chosen randomly. In other embodiments, the predetermined order is not random. In one embodiment, the computer software is used to specify the order.

V. Error-Correction Methods

In optical and electrical detection methods described above, errors can occur in binding and/or detection of signals. In some cases, the error rate can be as high as one in five (e.g., one out of five fluorescent signals is incorrect). This equates to one error in every five-cycle sequence. Actual error rates may not be as high as 20%, but error rates of a few percent are possible. In general, the error rate depends on many factors including the type of analytes in the sample and the type of probes used. In an electrical detection method, for example, a tail region may not properly bind to the corresponding probe region on an aptamer during a cycle. In an optical detection method, an antibody probe may not bind to its target or bind to the wrong target.

Additional cycles are generated to account for errors in the detected signals and to obtain additional bits of information, such as parity bits. The additional bits of information are used to correct errors using an error correcting code. In one embodiment, the error correcting code is a Reed-Solomon code, which is a non-binary cyclic code used to detect and correct errors in a system. In other embodiments, various other error correcting codes can be used. Other error correcting codes include, for example, block codes, convolution codes, Golay codes, Hamming codes, BCH codes, AN codes, Reed-Muller codes, Gappa codes, Hadamard codes, Walsh codes, Hagelbarger codes, polar codes, repetition codes, repeat-accumulate codes, erasure codes, online codes, group codes, expander codes, constant-weight codes, tornado codes, low-density parity check codes, maximum distance codes, burst error codes, luby transform codes, fountain codes, and raptor codes. See Error Control Coding, $2^{nd}$ Ed., S. Lin and D J Costello, Prentice Hall, New York, 2004. Examples are also provided below that demonstrate the method for error-correction by adding cycles and obtaining additional bits of information.

One example of a Reed-Solomon code includes a RS (15,9) code with 4-bit symbols, where n=15, k=9, s=4, and t=3, and $n=2^s-1$ and k=n-2t, "n" being the number of symbols, "k" being the number of data symbols, "s" being the size of each symbol in bits, and "t" being the number of errors that can be corrected, and "2t" being the number of parity symbols. There are nine data symbols (k=9) and six parity symbols (2t=6). If base-X numbers are used, and X=4, then each fluorescent color is represented by two bits (0 and 1). A pair of colors may be represented by a four-bit symbol that includes two high bits and two low bits.

Figure 11:
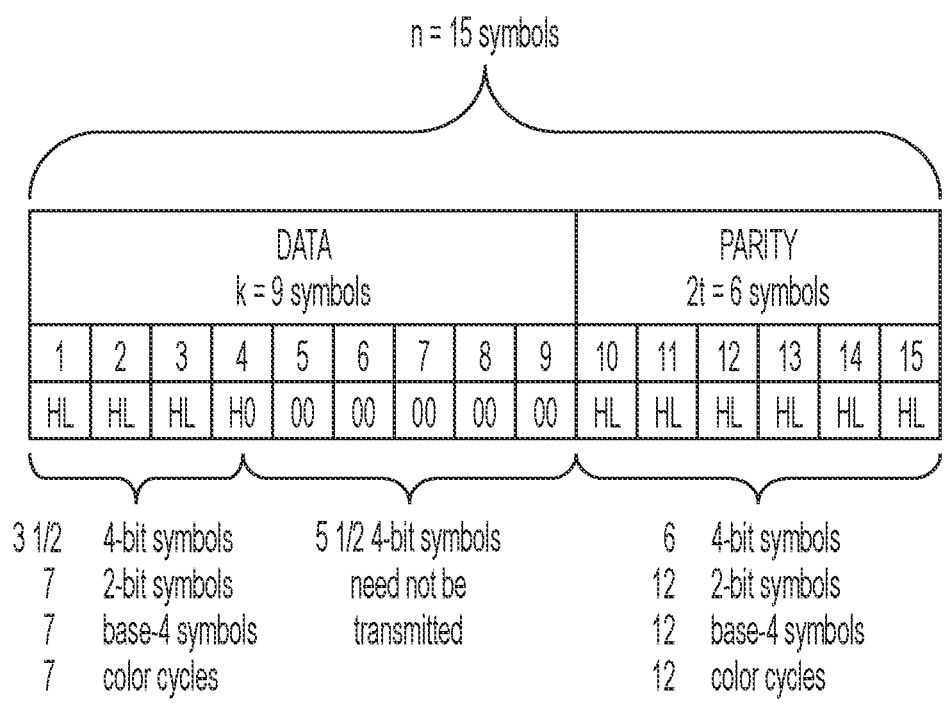
FIG. 11 illustrates an example Reed-Solomon error correction structure, according to one embodiment of the invention.

FIG. 11 illustrates the RS (15,9) example structure. Since base-4 was chosen, seven probe pools, or a sequence of seven colors, are used to identify each target analyte. This sequence is represented by $3^{1/2}$, 4-bit symbols. The remaining $5^{1/2}$ data symbols are set to zero. A Reed-Solomon RS (15,9) encoder then generates the six parity symbols, represented by 12 additional probe pools. Thus, a total of 19 probe pools (7+12) are required to obtain error correction for t=3 symbols.

Monte Carlo simulations of error-correcting code performance have been performed assuming seven probe pools, to identify up to 16,384 distinct targets. Using these simulations, the maximum permissible raw error rate (associated with identifying a fluorescent label) to achieve a corrected error rate of $10^{-5}$ was determined for different numbers of parity bits. Table 10A below illustrates these findings.

TABLE 10A

Error rates

| Reed-Solomon parity symbol number | Maximum permissible raw error rate to ensure a correct error rate <$10^{-5}$ |
|---|---|
| 6 | 2% |
| 8 | 5% |
| 10 | 10% |

In some embodiments, a key is generated that includes the expected bits of information associated with an analyte (e.g., the expected order of probes and types of signals for the analyte). These expected bits of information for a particular analyte are compared with the actual L bits of information that are obtained from the target analyte. Using the Reed-Solomon approach, an allowance of up tot errors in the signals can be tolerated in the comparison of the expected bits of information and the actual L bits of information.

In some embodiments, a Reed-Solomon decoder is used to compare the expected signal sequence with an observed signal sequence from a particular probe. For example, seven probe pools may be used to identify a target analyte, the expected color sequence being BGGBBYY, represented by 14 bits. Additional parity pools may then be used for error correction. For example, six 4-bit parity symbols may be used. Then, as shown below in Table 10B, the expected signal sequence is compared against the observed signal sequence, and a decoded signal sequence is generated from the comparison.

TABLE 10B

| EXPECTED SIGNAL SEQUENCE | BGGBBYYYYRYBBYGBYGR |
|---|---|
| OBSERVED SIGNAL SEQUENCE | BGGRBYYYYGYBBYGBYGR |
| DECODED SIGNAL SEQUENCE | BGGBBYYYYRYBBYGBYGR |

The observed signal sequence has 2 errors in an ordered sequence of 19 signals. When the received probe sequence is decoded by a Reed-Solomon decoder, the original, transmitted probe sequence is recovered. The expected signal sequence is the sequence that is designed to identify one type of analyte. The observed signal sequence is the sequence of fluorescent signals received at a particular location on a solid substrate. The decoded sequence is the recovered sequence after decoding by an error correcting code decoder.

In another embodiment, using electrical detection of analytes, the probes and selected bits of information used in the electrical detection method follow error correction calculations as shown in Table 11 below. In Example 1, 3 bits of ID are chosen, which corresponds to a total of 8 target analytes and 8 ID numbers ($2^3=8$). In addition, the error factor is calculated to be the number of bits of error divided by the number of bits of ID. Here, the number of bits used for error correction in this example is 9 (3×3=9), and the error factor would be 3 (9/3=3). The total of bits per run is 12 (sum of 3 bits of ID and 9 bits of error correction). The number of bits per cycle can be chosen as 3 and the number of probes per cycle is determined to be 8 ($2^3=8$). Next, the number of cycles is calculated to be 4 based on the number of bits, error factor, and bits per cycle. The equation used is ((bits×(1+ error factor)/bits per cycle). Here, the calculation is (3×(1+ 3))/3)=4 cycles. In this example, one stop is used per electrical tag. The number of detectable probes can be increased based on selection of higher bits, as shown in examples 2-5 in Table 11.

TABLE 11

Summary of Example Assays Using Various Number of Bits, Number of Targets, Number of Probes, Cycles and Stop Types

| | Example # | | | | | Equation |
|---|---|---|---|---|---|---|
| | 1 | 2 | 3 | 4 | 5 | |
| # Bits ID | 3 | 4 | 8 | 12 | 16 | bits |
| # ID's (# of Simultaneous Targets) | 8 | 16 | 256 | 4,096 | 65,536 | $2^{bits}$ |
| Error Factor (# Bits Error/# Bits ID) | 3 | 3 | 3 | 3 | 3 | err |
| # Bits Error Correction | 9 | 12 | 24 | 36 | 48 | err * bits |
| Total # of Bits per Run | 12 | 16 | 32 | 48 | 64 | bits * (1 + err) |
| # Bits per Cycle | 3 | 4 | 4 | 6 | 8 | bpc |
| # Probes per Cycle | 8 | 16 | 16 | 64 | 256 | $2^{bpc}$ |
| # Cycles | 4 | 4 | 8 | 8 | 8 | (bits * (1 + err))/bpc |
| # Stops | 1 | 1 | 2 | 2 | 2 | stp |
| # Stop Types | 1 | 3 | 3 | 3 | 3 | typ |
| # Flow Sequences per Cycle | 3 | 7 | 13 | 9 | 13 | 1 + 2 * stp * typ |
| # Levels | 9 | 7 | 4 | 8 | 10 | |
| Max # of Probes | 8 | 18 | 27 | 84 | 324 | |

Additional description about electrical detection methods are found in U.S. Provisional Application No. 61/868,988, which is incorporated by reference in its entirety.

VI. Dynamic Range

The concentrations of analytes such as proteins in samples such as human serum can vary by factors of greater than $10^{10}$. The dynamic ranges of likely concentrations for particular proteins are generally smaller. For example, Ferritin is normally found between $10^4$-$10^5$ μg/mL in human serum. Most protein concentrations do not vary by more than a factor of $10^3$ from one human serum sample to another.

Figure 12A:
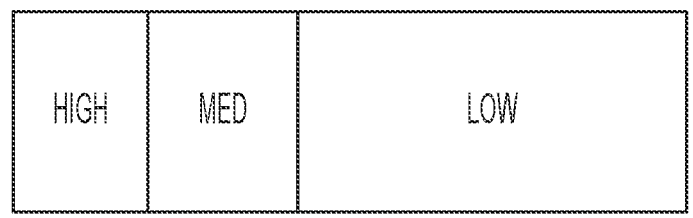
FIG. 12A illustrates an example substrate divided into three regions depicting target analyte concentration levels, according to one embodiment of the invention.

Because it is difficult to detect fluorescent labels corresponding to target analytes at a large dynamic range of concentrations, a substrate containing target analytes can be divided into concentration regions. For example, FIG. 12A shows an example substrate that has been divided into regions "HIGH," "MED," and "LOW." The same target analytes may be distributed throughout each of the three regions. However, the target analytes are diluted to different concentration samples before distribution: one sample each of high concentration (HIGH), medium concentration (MED), and low concentration (LOW). In one embodiment, the target analytes in the "HIGH" region of the substrate are distributed at a concentration of around 1 protein per square micron, the target analytes in the "MED" region are distributed at around $10^2$ proteins per square micron, and the target analytes in the "LOW" region are distributed at around $10^4$ proteins per square micron. In a further embodiment, the dilutions are adjusted such that the density of fluorescent labels in each concentration region is around one tag per 10-25 pixels in an image of the substrate.

Figure 12B:
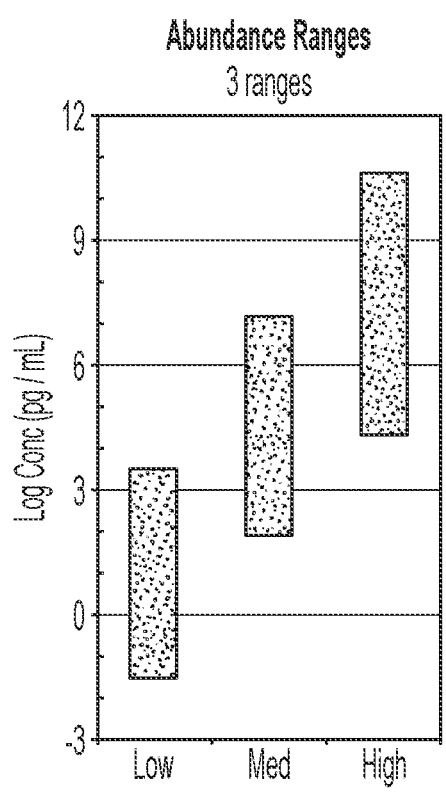
FIGS. 12B-12C show graphs of target analyte abundance ranges, according to one embodiment of the invention.
Figure 12C:
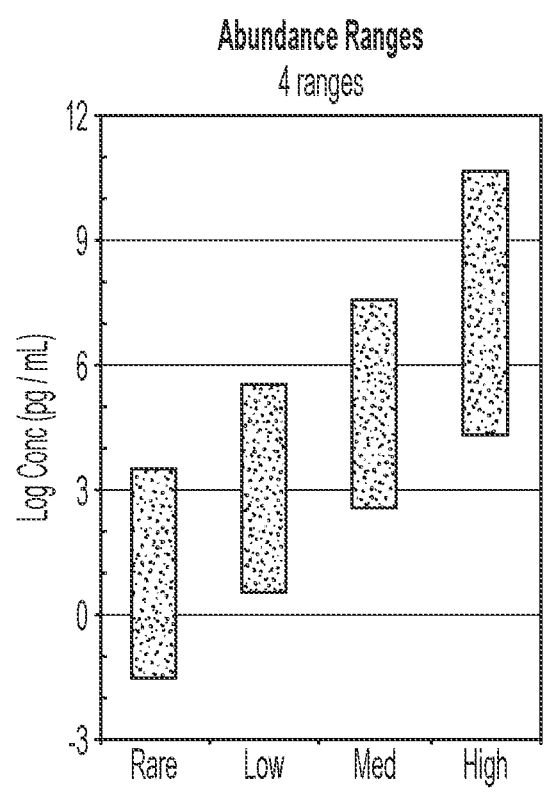

FIG. 12B is a graph showing an example of abundance ranges of target analytes from a sample, located in different concentration regions (Low, Med, and High) of a substrate. FIG. 12C is also a graph showing abundance ranges of target analytes, with a fourth concentration region: "Rare." Overlapping abundance ranges demonstrate that certain target analytes may be detected in more than one concentration region. These graphs (FIGS. 12B and 12C) were generated from simulations performed in Example 5 (below).

In one embodiment, particular target analytes within a sample may be separated from the sample to increase the dynamic range even further. For example, in a sample of human serum, it may be desirable to remove albumin, a highly abundant protein. Any separation technique may be used, including high-performance liquid chromatography.

Once the different dilutions of target analyte samples have been attached to the substrate, probes may be applied to selectively bind to the target analytes. In an embodiment, the probes may be prepared at varying concentrations so that they selectively bind to the target analytes of medium abundance in the "MED" region of the substrate.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B (1992).

Example 1

Optical Detection Assay for Multiple Analytes Using a Single Fluorescent Tag, Single Pass, Dark Counted, and 1 Bit Per Cycle In one example, the method is performed using the following parameters: Single Fluorescent Tag (Single Color), Single Pass, Dark Counted, and 1 Bit per Cycle. FIG. 9 illustrates this example where the fluorescent surface density is lower than the deposited protein surface density. The Figure shows four different types of target proteins mixed with other non-target proteins shown randomly deposited on the surface.

Table 12 below shows how a total of four bits of information can be obtained using four cycles of hybridization and stripping, such that there is one pass per cycle. The signals obtained from the four cycles are digitized into bits of information.

As illustrated in FIG. 13, probes are introduced for Analyte A in Cycle 1, and the presence of the analyte is indicated by a "1." In Cycle 2, the probes for Analyte A are not added, and the analyte is not detected, indicated by a "0." After four cycles, Analyte A can be associated with a binary code of "1010." In a base-2 system, the code is represented as "1010". In a base-10 system, the same code is represented as "10" (e.g., $(2^3 \times 1) + (2^2 \times 0) + (2^1 \times 1) + (2^0 \times 0) = 10$).

In the first cycle, only antibody probes for targets A and B are included in the probe pool. The imaging system measure a single color image for the first cycle, where A and B molecules fluoresce, but C and D are dark (no probes and no signal). The probes for targets A and B are stripped. For the second cycle, antibody probes for targets C and Dare introduced and are imaged and then the antibody probes for C and Dare stripped. For the third cycle, antibody probes targets A and C are introduced and imaged. The antibody probes for targets A and Care then stripped. For the fourth cycle, antibody probes for targets B and D are introduced, and the fluorescent molecules are imaged. After imaging multiple cycles, the ID (code of fluorescent signals) for the target molecule at each position is determined. Only 2 cycles are necessary for identification of 4 molecules. In some embodiments, additional cycles can be used for error correction information, which is described below, or to identify more than 4 molecules.

TABLE 12

Single Fluorescent Tag, Single Pass, Dark Counted, and 1 Bit Per Cycle

|  | Cycle 1 | Cycle 2 | Cycle 3 | Cycle 4 | ID - Binary | ID - Decimal |
| --- | --- | --- | --- | --- | --- | --- |
| Analyte A | 1 | 0 | 1 | 0 | 1010 | 10 |
| Analyte B | 1 | 0 | 0 | 1 | 1001 | 9 |
| Analyte C | 0 | 1 | 1 | 0 | 0110 | 6 |
| Analyte D | 0 | 1 | 0 | 1 | 0101 | 5 |

Example 2

Optical Detection Assay for Multiple Analytes Using Single Color, Four Passes Per Cycle, Dark Pass not Counted, and 2 Bits Per Cycle In another example, the following parameters are used: Single Color, Four Passes per Cycle, Dark Pass Not Counted, and 2 bits per Cycle.

In FIG. 14, four passes are shown for a single cycle. The first pass includes probes for target analyteA The probes for target A hybridize, and the detectable signals are imaged. For example, the probes comprise a green fluorescent molecule and emit a green color. The probes for target A are not stripped from the substrate in this example. In pass 2, the probes for target B are hybridized, and the probes for target B have the same fluorescent color as the probes for target A. The additional signals for target B (green fluors) are detected, and both of the signals for targets A and B are imaged. The probes for A and B are not stripped from the substrate.

In pass 3, probes for target C are introduced and hybridize to target C. Probes for target C emit the same fluorescent color as targets A and B. The signals emitted from the probes for targets A, B and C are imaged. In pass 4, probes for target D are hybridized, and the signals emitted from targets A, B, C and D are imaged. Finally, all probes are stripped, and the first cycle is completed.

Multiple cycles can be performed to increase the number of targets to be quantified. It is not necessary to have probes for every target in every pass, and there may be many more than four molecules observed.

Table 13 below shows how signals obtained from one cycle with four passes are digitized and represented as two bits of information per cycle. Over the period of four cycles, a total of 8 bits of information per analyte can be obtained. Table 14 provides the key for the digital output for four passes in a cycle.

TABLE 13

Single Color, Four Pass, Dark Not Counted, 2 Bits per Cycle

| Pass | Cycle 1 | | | | Cycle 2 | | | | Cycle 3 | | | | Cycle 4 | | | | ID-Binary | ID-Decimal |
|---|---|---|---|---|---|---|---|---|---|---|---|---|---|---|---|---|---|---|
|  | 1 | 2 | 3 | 4 | 1 | 2 | 3 | 4 | 1 | 2 | 3 | 4 | 1 | 2 | 3 | 4 |  |  |
| Analyte A | 1 | 1 | 1 | 1 | 0 | 0 | 1 | 1 | 0 | 1 | 1 | 1 | 1 | 1 | 1 | 1 | 0210 | 36 |
| Analyte B | 0 | 1 | 1 | 1 | 1 | 1 | 1 | 1 | 0 | 1 | 1 | 1 | 0 | 1 | 1 | 1 | 1011 | 69 |
| Analyte C | 0 | 0 | 1 | 1 | 0 | 0 | 0 | 1 | 0 | 0 | 1 | 1 | 1 | 1 | 1 | 1 | 2320 | 184 |
| Analyte D | 0 | 0 | 0 | 1 | 0 | 1 | 1 | 1 | 0 | 0 | 0 | 1 | 0 | 0 | 1 | 1 | 3132 | 222 |
| Analyte A | 0 | | | | 2 | | | | 1 | | | | 0 | | | | 0210 | 36 |
| Analyte B | 1 | | | | 0 | | | | 1 | | | | 1 | | | | 1011 | 69 |
| Analyte C | 2 | | | | 3 | | | | 2 | | | | 0 | | | | 2320 | 184 |
| Analyte D | 3 | | | | 1 | | | | 3 | | | | 2 | | | | 3132 | 222 |

TABLE 14

Key for Example 2 Assay

| Pass | | | | ID-Hex | ID-Decimal |
|---|---|---|---|---|---|
| 1 | 2 | 3 | 4 | | |
| 1 | 1 | 1 | 1 | 0 | 0 |
| 0 | 1 | 1 | 1 | 1 | 1 |
| 0 | 0 | 1 | 1 | 2 | 2 |
| 0 | 0 | 0 | 1 | 3 | 3 |

It is possible to use multiple fluors on the secondary analytes instead of performing successive hybridizations to achieve more bits of information per cycle. For instance, four colors of fluorescent tags on secondary antibodies would allow for one hybridization step and one stripping step per cycle to achieve two bits of information per cycle.

A combination of using multiple colors and also performing multiple hybridization steps per cycle could increase the number of bits measurable per cycle. For instance, using a four-color imaging system and performing 4 steps of hybridization per cycle would allow up to four bits of information per cycle to be achieved.

Example 3

Optical Detection Assay for Mulitple Analytes Using Five Colors, Three Passes Per Cycle, Dark Pass Counted, Four Bits Per Cycle In another example, the following parameters are used: Five Colors, Three Passes per Cycle, Dark Pass Counted, Four bits per Cycle.

The following tables illustrate an assay with a five color system with 3 passes of hybridization per cycle. A total of 16 levels or equivalently four bits of information is possible per cycle if the absence of any signal is considered to be a level (i.e., dark cycle counted). Table 16 provides a key for the ID code for each analyte.

TABLE 15

| Pass | Cycle 1 | | | Cycle 2 | | | Cycle 3 | | | Cycle 4 | | | ID-Hex | ID-Decimal |
|---|---|---|---|---|---|---|---|---|---|---|---|---|---|---|
|  | 1 | 2 | 3 | 1 | 2 | 3 | 1 | 2 | 3 | 1 | 2 | 3 |  |  |
| Analyte A | 1 | 1 | 1 | 0 | 0 | 1 | 5 | 5 | 5 | 2 | 2 | 2 | 13D4 | 5,076 |
| Analyte B | 0 | 2 | 2 | 0 | 4 | 4 | 0 | 5 | 5 | 0 | 0 | 3 | 5BE9 | 23,529 |
| Analyte C | 0 | 0 | 3 | 0 | 0 | 0 | 0 | 0 | 2 | 4 | 4 | 4 | 906A | 36,970 |
| Analyte D | 0 | 0 | 0 | 0 | 5 | 5 | 0 | 3 | 3 | 0 | 0 | 4 | 0E8C | 3,724 |
| Analyte A | 1 | | | 3 | | | D | | | 4 | | | 13D4 | 5,076 |
| Analyte B | 5 | | | B | | | E | | | 9 | | | 5BE9 | 23,529 |
| Analyte C | 9 | | | 0 | | | 6 | | | A | | | 906A | 36,970 |
| Analyte D | 0 | | | E | | | 8 | | | C | | | 0E8C | 3,724 |

TABLE 16

| Pass | | | ID-Hex | ID-Decimal |
|---|---|---|---|---|
| 1 | 2 | 3 | | |
| 0 | 0 | 0 | 0 | 0 |
| 1 | 1 | 1 | 1 | 1 |
| 0 | 1 | 1 | 2 | 2 |
| 0 | 0 | 1 | 3 | 3 |
| 2 | 2 | 2 | 4 | 4 |
| 0 | 2 | 2 | 5 | 5 |
| 0 | 0 | 2 | 6 | 6 |
| 3 | 3 | 3 | 7 | 7 |
| 0 | 3 | 3 | 8 | 8 |
| 0 | 0 | 3 | 9 | 9 |
| 4 | 4 | 4 | A | 10 |
| 0 | 4 | 4 | B | 11 |
| 0 | 0 | 4 | C | 12 |
| 5 | 5 | 5 | D | 13 |

TABLE 16-continued

| Pass | | | | |
|---|---|---|---|---|
| 1 | 2 | 3 | ID-Hex | ID-Decimal |
| 0 | 5 | 5 | E | 14 |
| 0 | 0 | 5 | F | 15 |

Table 17 below shows the number of bits per cycle for a multi-color, multi-pass hybridization for optical detection, with and without the absence of signal considered to be a level (dark cycle counted/dark cycle not counted).

TABLE 17

Number of Bits per Cycle for Multi-Color, Multi-pass Hybridization for Optical Detection

| # Colors Per Cycle | # Passes (Hybridizations) Per Cycle | # Levels Per Cycle | # Bits Per Cycle Dark Not Counted | # of Levels Per Cycle | # Bits Per Cycle Dark Counted |
|---|---|---|---|---|---|
| 1 | 1 | 1 | 0.00 | 2 | 1.00 |
| 1 | 2 | 2 | 1.00 | 3 | 1.58 |
| 1 | 3 | 3 | 1.58 | 4 | 2.00 |
| 1 | 4 | 4 | 2.00 | 5 | 2.32 |
| 1 | 5 | 5 | 2.32 | 6 | 2.58 |
| 2 | 1 | 2 | 1.00 | 3 | 1.58 |
| 2 | 2 | 4 | 2.00 | 5 | 2.32 |
| 2 | 3 | 6 | 2.58 | 7 | 2.81 |
| 2 | 4 | 8 | 3.00 | 9 | 3.17 |
| 2 | 5 | 10 | 3.32 | 11 | 3.46 |
| 3 | 1 | 3 | 1.58 | 4 | 2.00 |
| 3 | 2 | 6 | 2.58 | 7 | 2.81 |
| 3 | 3 | 9 | 3.17 | 10 | 3.32 |
| 3 | 4 | 12 | 3.58 | 13 | 3.70 |
| 3 | 5 | 15 | 3.91 | 16 | 4.00 |
| 4 | 1 | 4 | 2.00 | 5 | 2.32 |
| 4 | 2 | 8 | 3.00 | 9 | 3.17 |
| 4 | 3 | 12 | 3.58 | 13 | 3.70 |
| 4 | 4 | 16 | 4.00 | 17 | 4.09 |
| 4 | 5 | 20 | 4.32 | 21 | 4.39 |
| 5 | 1 | 5 | 2.32 | 6 | 2.58 |
| 5 | 2 | 10 | 3.32 | 11 | 3.46 |
| 5 | 3 | 15 | 3.91 | 16 | 4.00 |
| 5 | 4 | 20 | 4.32 | 21 | 4.39 |
| 5 | 5 | 25 | 4.64 | 26 | 4.70 |

Example 4

Demonstrating DNA Probe and Target Hybridization and Strpping at a Bulk Level

Nucleic acids were used to demonstrate APTIQ probe/target hybridization and stripping cycles at a bulk level. Oligonucleotides (Table 18) were purchased from IDT Integrated DNA Technologies (Coralville, Iowa). Oligos were dissolved in molecular grade water at a final concentration of 100 µM and were stored at −20° C.

TABLE 18

Oligo and Probe Sequences

| Sequence Name | Sequence |
|---|---|
| Oligo B1 | /5AmMC6/d(A)$_{40}$GCA CCC TTG GTC TCC TCC A |
| Oligo B2 | /5AmMC6/d(A)$_{40}$CT CAG CAG CAT CTC AGG GCC A |
| Oligo B3 | /5AmMC6/d(A)$_{40}$GCT GCA TGC ACG CAC ACA CA |

| Probe Name | Sequence |
|---|---|
| Cy3-anti-B1 | /5Cy3/TGG AGG AGA CCA AGG GTG CAG T |
| Cy3-anti-B2 | /5CY3/TGG CCC TGA GAT GCT GCT GAG T |
| Cy3-anti-B3 | /5Cy3/TGT GTG TGC GTG CAT GCA GC |
| Cy5-anti-B1 | /5Cy5/TGG AGG AGA CCA AGG GTG CAG T |
| Cy5-anti-B2 | /5Cy5/TGG CCC TGA GAT GCT GCT GAG T |
| Cy5-anti-B3 | /5Cy5/TGT GTG TGC GTG CAT GCA GC |

Oligos with C6-amino linkers were printed on microarrays at Arrayit (Sunnyvale, Calif). Unless otherwise specified, all reagents and equipment used in these Examples were purchased from Array It. Oligos were printed at 50 µM final concentration in 1×MSP buffer (Cat ID: MSP) on SuperEpoxy 2 Microarray Substrates (Cat ID: SME2), on a NanoPrint Microarrayer using SMP3 Microarray Printing Pin. Printed microarrays were dried overnight.

Prior to use, a substrate slide was blocked for 1.5 hours in Blockit Blocking Buffer (Cat ID: BKT) at room temperature with gentle agitation at 350 rpm, followed by washing 3 times, 1 minute at a time, with Wash Buffers 1, 2, 3 at 1×(Cat ID: WB1, WB2, WB3) in a square petri dish, 30 ml volume at 350 RMP 2 mm orbit. The slide was then spin dried for 10 seconds with a Microarray Centrifuge (Cat ID: MHC110).

A Gasket (Cat ID: GAHC4×24) was blocked in Blockit blocking buffer for at least 1 hour, rinsed using distilled water, dried using Microarray Cleanroom Wipe (Cat ID: MCW), and loaded into the lid of the cassette (Cat ID: AHC4×24). Hybit hybridization buffer (Cat ID: HHS2) was used for hybridization at 1×Cy3 or Cy5 labeled probes (Table 18) (corresponding to color R-red, or G-green, respectively) were mixed in the probe pools in 1 xhybridization buffer. 75 µl of hybridization probe pools were loaded on the microarray and incubated for 15 minutes at 37 C.°, RMP 350 on Arrayit Array Plate Hyb Station (Cat ID: MMHS110V).

100 µl of wash buffer (at 37° C.) 1 was added to each well and then incubated for 1 minute at RMP 350. The wash buffer was then taken out by expelling the wash buffer into the waste. Wash buffer 1 was used two more times, wash buffer 2 was used three times and then wash buffer 3 was used three times.

The slide was removed from the gasket submerged in wash buffer 3 in a container, and spin dried in the Microarray Centrifuge. The slide was scanned in an Axon scanner 4200A with setting of PMT250 for both 532 and 635 Lasers. The slide was incubated with spots side up in a square petri dish containing 30 ml of Stripping Buffer A at 350 RMP for 10 minutes. Stripping Buffer A was removed and immediately followed by addition of 30 ml of Stripping Buffer B. The procedure was repeated with Stripping Buffer B and Stripping Buffer C. The slide was dried in the microarray centrifuge and prepared for the next cycle of hybridization. The slide was scanned after stripping to confirm the efficiency of the stripping.

Figure 15:
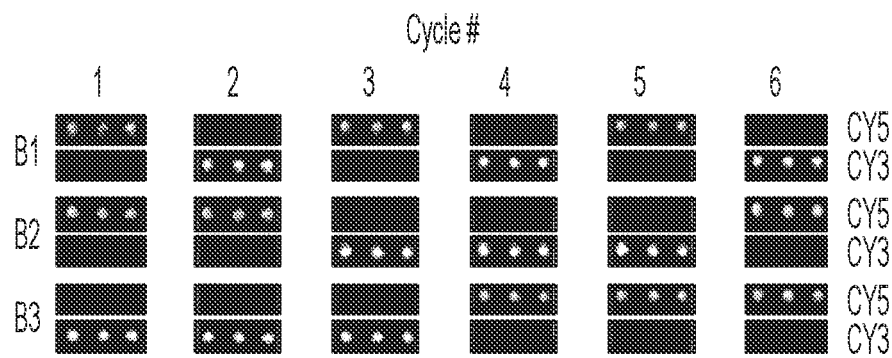
FIG. 15 shows color sequences and IDs for target analytes, and shows scanning results of the target analytes for the probing, binding, and stripping cycles, according to one embodiment of the invention.

FIG. 15 illustrates the scanning results: three oligo targets, (B1, B2, and B3) were identified by probing binding and stripping for 6 cycles. The color sequence of each oligo target was correctly identified.

Example 5

Using DNA to Demonstrate Single Molecule Counting

We describe a method for the identification and quantification of single molecules. Oligonucleotides (Table 19) were purchased from IDT Integrated DNA Technologies. Oligos were dissolved in molecular grade water at final concentration 100 uM and were stored at −20° C.

chips used were 500 μm, 675 μm, and 1000 μm. A thermal oxide was grown on the silicon chips of 100 nm and then diced into slides.

A slide was incubated in a solution of 4 DNA oligos (Table 19), each oligo ending in a C6 molecule. The sequences of the 4 oligos were A, B, C & D corresponding to the genes encoding for KRAS, EGFR, BRAF and P53. The 4 oligos with C6-amino linker were mixed at 100 nM per oligo in lx micro spotting solution (Cat ID: MSS,ArrayIt) and then incubated on the epoxy coated silicon slide in a container at room temperature overnight. During incubation, a reaction between the epoxy coating and the C6 oligos covalently bonded the single stranded DNA to the surface. The slide was then washed with molecule grade water for 5 minutes, 3 times, followed by incubation in Array It BlockIt blocking solution for 1 hour at room temperature with gentle agitation at 350 rpm, followed by washing 3 times for 1 minute each time with Wash Buffers 1, 2, 3 at 1× in a square petri dish, 30 ml volume at 350 RMP 2 mm orbit. The slide was spin dried for 10 seconds with the Microarray Centrifuge.

The chip was fabricated with glue into a biochip consisting of 3 parts, silicon chip, peek frame, and a 170 μm-thick coverslip glass. The coverslip (Nexterion, Tempe, Ariz.) was glued on the silicon slide with Bostik glue mixed with 50 uM beads (Gelest, Morrisville, Pa.) on an in-house developed device. The glue and beads was packed in 3 cc syringe (Hamilton Company, Reno, Nev.) and centrifuged in EFD ProcessMate centrifuge (Nordson, Westlake, Ohio) and then delivered by Nordson EFD Ultimus I glue dispenser.

Cy3 or Cy5 labeled probes (Table 19) were mixed in the probe pools in 1×Hybit hybridization buffer. Hybridization

TABLE 19

| Oligo and Probe Sequences | |
|---|---|
| Sequence Name | Sequence |
| C6-P53 | /5AmMC6/AAA AAA ACT GCA CCC TTG GTC TCC TCC A |
| C6-BRAF | /5AmMC6/AAA AAA ACT CAG CAG CAT CTC AGG GCC A |
| C6-EGFR | /5AmMC6/AAA AAA GCT GCA TGC ACG CAC ACA CA |
| C6-KRAS | /5AmMC6/AAA AAA ATC CCA GCA CCA CCA CTA CCG A |
| Probe Name | Sequence |
| Cy3-anti-P53 | /5Cy3/TGG AGG AGA CCA AGG GTG CAG T |
| Cy3-anti-BRAF | /5Cy3/TGG CCC TGA GAT GCT GCT GAG T |
| Cy3-anti-EGFR | /5Cy3/TGT GTG TGC GTG CAT GCA GC |
| Cy3-anti-KRAS | /5Cy3/TCG GTA GTG GTG GTG CTG GGA T |
| Cy5-ant-P53 | /5Cy5/TGG AGG AGA CCA AGG GTG CAG T |
| Cy5-anti-BRAF | /5Cy5/TGG CCC TGA GAT GCT GCT GAG T |
| Cy5-anto-EGFR | /5Cy5/TGT GTG TGC GTG CAT GCA GC |
| Cy5-anti-KRAS | /5Cy5/TCG GTA GTG GTG GTG CTG GGA T |

Silicon slides were purchased from University Wafer (Boston, Mass.), diced (American Precision Dicing Inc., San Jose, Calif.), and coated with Super Epoxy substrate (Array It). The single crystal silicon chips were prepared as 25 mm×75 mm substrate slides. The thickness of the silicon solution from pool #1 was delivered in the biochip and incubated for 15 minutes at room temperature. The chip was then washed with washing buffer 1, 2 and 3 (Array It), 8 times with each buffer. 15% glycerol in 1×SSPE (150 mM NaCl, 10 mMNaH2P04, 1mMEDTA) was added to the chip before imaging. Successive probe pools of probes 1, 2, 3, 4 were hybridized and stripped. After each hybridization step, an imaging system imaged 12 regions of the slide, each region being 1 00 μm×100 μm. The camera used was a Hamamatsu Orca 4.0 with a 40× magnification system using Olympus part # UAPON40W.

After imaging, the chip was rinsed with molecular grade water and then stripped in the stripping buffer A, B, C (Array It), 8 times each buffer. 15% glycerol in 1×SSPE was added to the chip before imaging. After cycle 1 which includes hybridization probe pool #1, imaging, stripping, imaging, the cycle 2 starts with hybridization with probe pool #2.

Data was taken on two slides (slides #177 and #179, FIG. 16A), each slide containing twelve fields. Each field was 100 μm×100 μm. A two-color imaging system was used with CY3 and CY5 filters. For each slide, at least 12-14 cycles of data were collected, with the analysis using 9 to 10 cycles of data. The mapping of target identification ID to color sequence is illustrated in Table 19. In FIG. 16A, each color maps to a sequence such that a probe is labeled with CY5 or CY3, corresponding respectively to color R (red) or G (green), which maps to 1 or 0 with 1 bit of information being acquired per cycle (FIG. 16B). For this case, the error correction scheme was conservative and required zero errors per target, an error being defined as a positive identification in a sequence where it was not expected. Up to five missing sequences were allowed per molecule. Missing sequences are cases where a molecule is not identified in a cycle. These are not classified as errors.

Slides #177 & #179 were measured under similar conditions. A small portion of each slide was measured (measuring the entire slide is an implementation of scale and automation). FIG. 16A shows the number of molecules in each field with the number of each gene that was identified. The percentages of identified molecules were 12%-13%.

Figure 17:
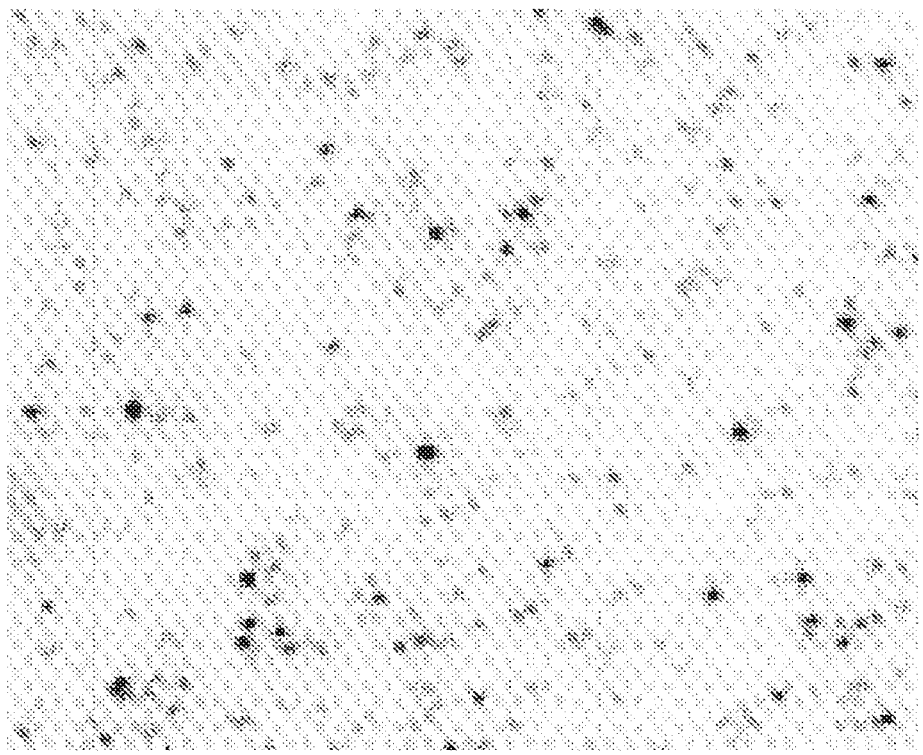
FIG. 17 is an image of single fluor probes hybridized to target analytes bonded to a substrate, according to one embodiment of the invention.

FIG. 17 illustrates an image taken with the prototype imager of single fluor DNA probes that have been hybridized to the DNA target oligos covalently bonded to the surface. Between 10%-15% of the identified molecules had multiple fluors per spot due to aggregation that occurred during sample attachment.

Figure 18:
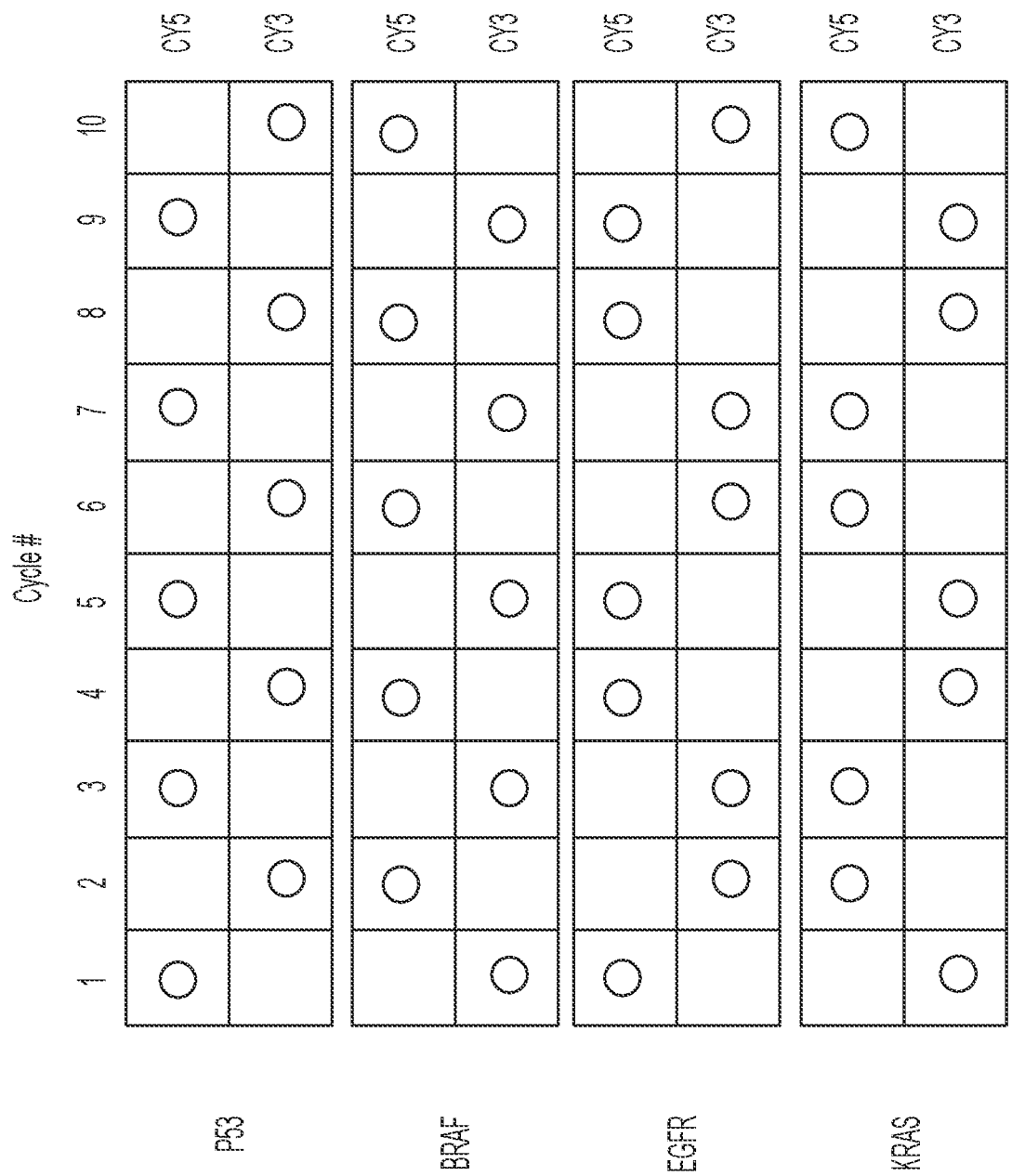
FIG. 18 illustrates examples of identification of various target analytes using single fluor detection, according to one embodiment of the invention.

FIG. 18 illustrates representative examples of identification of each of the four targets from slide #177 (FIG. 16A). Each spot in the circle is aligned to center on the target. The targets are identified with single fluor detection. Approximately 10%-15% of the targets on the image were clustered molecular species where more than a single fluor was bound. Inspecting the data shows that for both experiments, greater levels of P53 and KRAS were observed than BRAF and EGFR. The total number of molecules identified was under 2000 in both cases, demonstrating the potential high sensitivity of the method in detecting and identifying low numbers of molecules.

Example 6

Demonstrating Peptide Probe and Target Hybridization and Stripping at a Bulk Level Peptides were used to demonstrate APTIQ probe/target binding and stripping cycles at bulk level. Peptide MUC1 (Sequence: APDTRPAPG) was purchased from American Peptide (Sunnyvale, Calif.). MUC1 was dissolved at 1 mg/ml in 1× peptide printing buffer 1 (Cat ID: PEP, ArrayIt). Peptide MUC 16 at 0.2 mg/ml, monoclonal antibodies against mouse anti-MUC1 C595 [Cat ID: NCRC48], and rabbit anti-MUC16 [Cat ID: EPSISR23] were purchased from Abeam (Cambridge, Mass.). The following secondary antibodies were also purchased from Abeam: goat anti-mouse IgGCy3 (CatiD: ab97035), goatanti-rabbitigGCy3 (CatiD: ab6939), goat anti-mouse IgG Cy5 (Cat ID: ab97037), goat anti-rabbit IgG Cy5 (Cat ID: ab6564).

Peptides were printed on microarrays at ArrayIt (Sunnyvale, Calif.). MUC1 peptide was printed at 0.5 mg/ml final concentration and MUC16 at 0.1 mg/ml in 1× peptide printing buffer 2 (Cat ID: PEP, ArrayIt) on SuperEpoxy 2 Microarray Substrates on a NanoPrint Microarrayer using SM3 Microarray Printing Pin. Printed microarrays were dried overnight.

Prior to use, the slide was blocked for 1.5 hours in Blockit Plus Blocking Buffer (Cat ID: BKTP, ArrayIt) at room temperature with gentle agitation at 350 rpm, followed by washing 3 times 1 minute each with 1×PBS in a square petri dish, 30 ml volume at 350 RMP 2 mM orbit. The slide was spin dried for 10 seconds with the ArrayIt Microarray Centrifuge.

Anti-MUC1 and anti-MUC 16 primary antibodies were diluted 250 fold in 1×PBS buffer (137 mM NaCl; 2.7 mMKCl; 10 mMNa2HPO4; 2 mMKH2PO4, pH7.4). Secondary antibodies were diluted 10000 fold in 1×PBS. Cy3 or Cy5 labeled antibodies were mixed in the 2 pools in 1×PBS: Pool #1: anti-mouse Cy3 and anti-rabbit Cy5; Pool #2: antirabbit Cy5 and anti-rabbit Cy3.

5 ml of the mixture of primary probe pools were added to the slide and incubated for 1 hour at room temperature in a container. The slide was then washed with 1×PBS, 3 times, 5 minutes each time with gentle shaking at 450 rpm.

Secondary antibody pool #1 was added to the slide and incubated for 1 hour at room temperature. The slide was then washed with 1×PBS, 3 times, 5 minutes each time with gentle shaking at 450 rpm. The slide was removed from the container and dried in the Microarray Centrifuge. The slide was scanned in Axon 4200A with settings at PMT250 for both 532 and 635 Lasers.

The slide was incubated with spots side up in a square petri dish containing 5 ml of Stripping Buffer (Cat ID: 21028, Fisher Scientific, Rockford, Ill.) at 300 RMP for 1 hour. The slide was then washed with distilled water 3 times, for 5 minutes each time. The slide was dried in the microarray centrifuge and then was prepared for the next cycle of antibody binding and stripping. The slide was scanned after stripping to make sure the stripping was efficient.

Figure 19:
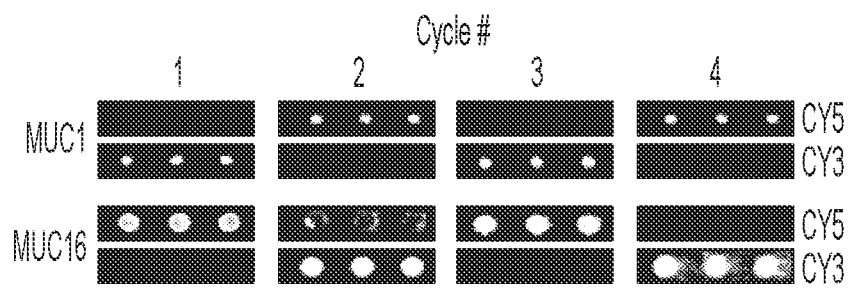
FIG. 19 shows color sequences and IDs for two target analytes, and shows scanning results of the target analytes for the probing, binding, and stripping cycles, according to one embodiment of the invention.

FIG. 19 illustrates the scanning results: two oligo targets, (MUC1 and MUC16) were identified by probing binding and stripping for 4 cycles. The color sequence of each oligo target was correctly identified.

Example 7

Using Peptides to Demonstrate Single Molecule Counting

Preparation of peptides was performed using the same technique as in Example 4. Peptide MUC1 (20 ng/ml) and MUC 16 (4 ng/ml) were diluted in ArrayIt 1×peptide printing buffer 2 (Array It, Sunnyvale, Calif) and then incubated on a silicon slide in a container at room temperature overnight. The slide was then washed with molecule grade water for 5 minutes, 3 times, followed by incubation in ArrayIt BlockIt plus blocking solution for 1 hour at room temperature with gentle agitation at 300 rpm. The chip was subsequently washed with molecular grade water for 5 minutes, 3 times. The slide was spin dried in microarray highspeed centrifuge. The slide was then built in biochip following the same procedures as above.

Primary antibodies are diluted 250 fold in 1×PBS. Secondary antibodies are diluted 10,000 fold in 1×PBS. A mixture of primary antibodies against MUC1 and MUC16 was delivered in the biochip and incubated for 60 minutes at room temperature. The chip was then washed with 8× with 1×PBS. A mixture of secondary antibodies (either pool #1 containing anti-mouse Cy3 and anti-rabbit Cy5 or pool #2 containing anti-rabbit Cy5 and anti-rabbit Cy3) was delivered in the biochip and incubated for 60 minutes at room temperature. The chip was then washed with washing 8× with 1×PBS. 15% glycerol in 1×SSPE was added to the chip before imaging.

Figure 20:
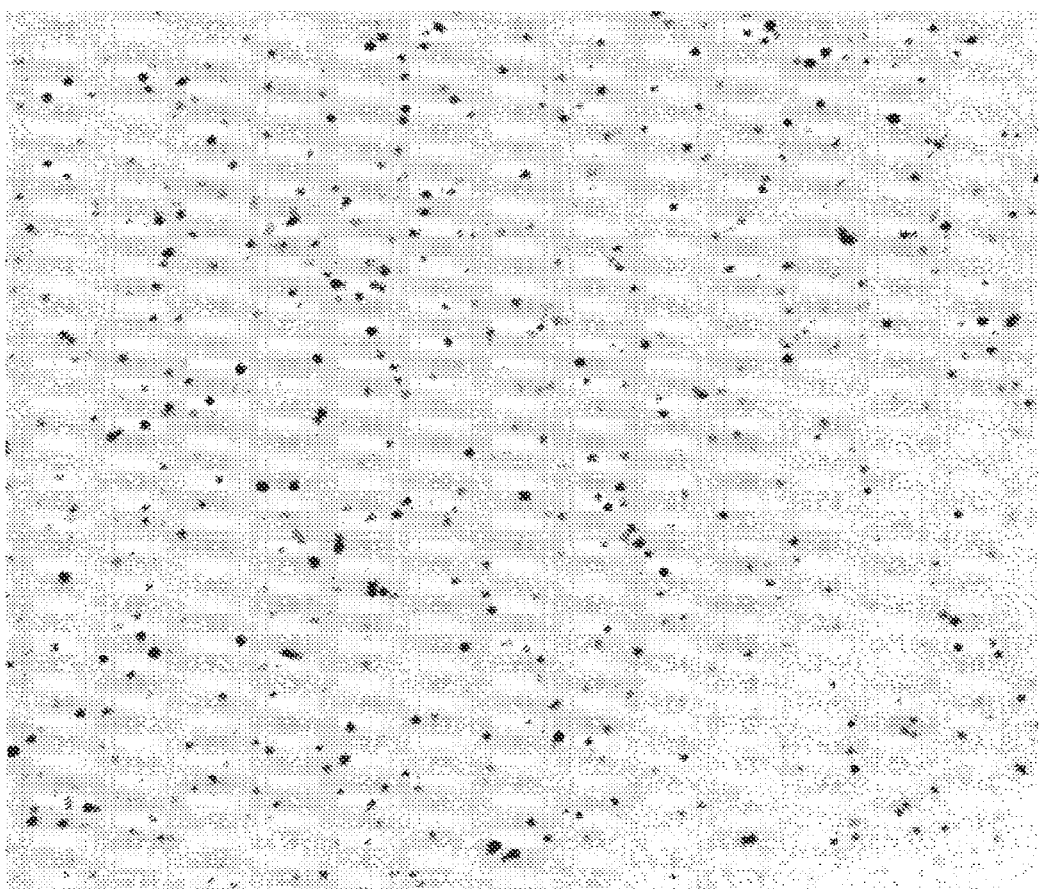
FIG. 20 is an image of single molecule peptides bound to a substrate, hybridized with conjugated antibodies, according to one embodiment of the invention.

FIG. 20 shows an image of single molecule peptides, such that conjugated antibodies (CY5 and CY3) were bound to isolated peptides which in turn were covalently bonded to the chip surface. Multiple fluors may be bound to a given antibody which creates a spread in the intensity of each observed molecule. These molecules were measured to be somewhat brighter than the DNA single molecule measurements where a single fluor was conjugated to each DNA probe. A total of six cycles were run of two proteins in single molecule mode. The molecules were bound and removed with high yield. Similar techniques can be used for scaling the system up to many more proteins and DNA/RNA targets.

After imaging, the biochip was rinsed with molecular grade water and then stripped in the stripping buffer (Cat ID: 21028, Fisher Scientific, Rockford, Ill.) for 1 hour followed by washing 8× with 1×PBS. 15% glycerol in 1×SSPE was added to the biochip before imaging. After cycle 1 which includes hybridization probe pool #1, imaging, stripping, imaging, the cycle 2 started with hybridization with probe pool #2.

Example 8

Quantifying the Human Plasma Proteome

A system model was created to demonstrate the feasibility of measuring the concentration of the ~10,000 proteins in the human plasma proteome across 12 logs of dynamic range using single-molecule identification with Reed-Solomon error correction encoding. For this model, the proteins in the plasma proteome were divided into three concentration regions as shown in FIG. 12B, referred to as low, medium and high-concentration regions. Theoretically, the total range of protein concentrations in the human plasma proteome is over 10 logs of dynamic range, but the concentration of each protein does not vary by more than a few logs. FIG. 12B depicts overlapping concentration regions. For each of the regions, probes are selected for proteins that are expected to fall within that particular region but not exceed the maximum concentration allowable for that region. Greater overlap can be achieved by adding another concentration range, as shown in FIG. 12C, with the trade-off being that a greater area of the substrate chip is used.

Figure 21:
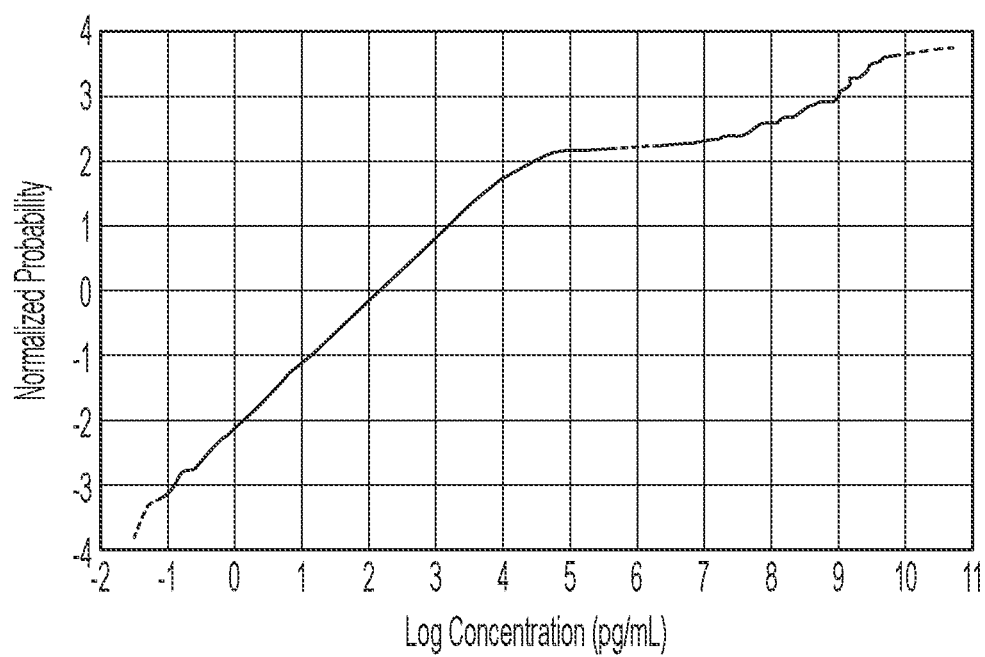
FIG. 21 shows a probability plot of estimated concentrations of proteins from the UniProt database, according to one embodiment of the invention.

The data used in the model came from the UniProt database (uniprot.org, PASTA file for organism 9606), "Toward a Human Blood Serum Proteome," Joshua Adkins et al., "The Human Plasma Proteome," N. Leigh Anderson et al. and "A High-Confidence Human Plasma Proteome Reference Set with Estimated Concentrations in Peptide Atlas," T. Farrah et al. Because not all proteins in the UniProt database are associated with a published concentration, random concentrations were assigned without changing the well-known highly abundant protein concentrations or the overall concentration. FIG. 21 shows a probability plot of the estimated concentrations. Concentrations between $10^5$ and $10^{11}$ pg/mL use published values. All published values found in the lower range were used. The remaining protein concentrations were estimated using a log normal approximation, with an estimated Gaussian distribution over a log normal space of 6 orders of magnitude from $10^{-1}$ pg/mL to $10^4$ pg/mL.

FIG. 22 lists specific estimated values for each of the abundance regions used. For each abundance region, the same target protein density (dTP) was assumed of 1.5 target proteins per $\mu m^2$. However, in the low abundance region, the number of high abundance region proteins per number of target proteins (rHT) was 25,000 to 1, and 250 to 1 in the medium abundance region. The number of high abundance proteins per pixel (rHP) ranged from 1,000 to 0.04. The number of pixels per target protein was constant for each of the three regions.

Figure 23:
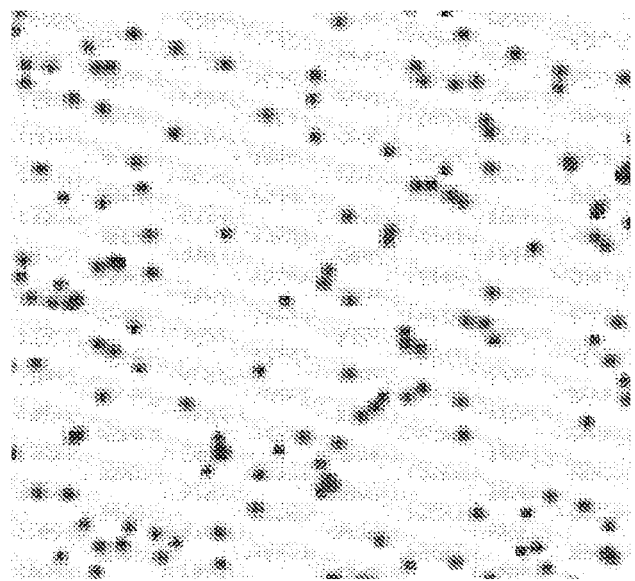
FIG. 23 is a simulated image of protein identification across any abundance range, according to one embodiment of the invention.

For the model, a four color imaging system is assumed giving 2 bits of information per cycle. FIG. 23 shows what a simulated image would be expected to look like for any of the colors across any of the abundance ranges, except for the case of albumin in the high abundance range when at any given time half of the target molecules are expected to be the same color. A field is the imaging region of the camera for a given exposure, in this case a 2,000 by 2,000 pixel camera is assumed with 40× magnification giving 163 nm pixels. A total of 2,500 fields (nF) are required for the low abundance region, but only 250 fields each are required for the high and medium abundance regions.

With the system model optimized, it was determine that the lowest abundance region would interrogate 9,575 proteins out of 9,719 or 98.5% of the proteome. At the other extreme, the high abundance region interrogates only the top 2.9% of the proteome. This is because there is only a small percentage of the proteins in the plasma proteome that make up the high abundance region. The measurable concentration ranges vary depending on the concentration region. The low abundance concentration region measures concentrations between 30 fg/mL and 300 ng/mL. The medium abundance concentration region measures concentrations between 82 pg/mL and 85 ug/mL. The high abundance concentration region measures concentrations between 20 ng/mL and 100 mg/mL. The total chip area required for this measurement is 320 mm 2, or a chip with dimensions of 18 mm×18 mm.

An analysis was conducted to determine the efficacy of Reed Solomon error correction in the plasma proteome measurement across 12 logs of dynamic range. There is an intrinsic error rate for each measurement cycle for each counted molecule. Since each molecule is spread out over a slide (particularly significant for the low abundance molecules), there will be other molecules nearby that should not cross-react with probes but still do. A robust system will allow for this to occur and will be able to correct these errors and give the correct identification of a molecule. The rate at which incorrect binding occurs per molecule per cycle is the raw error rate. The system error rate is the per molecule identification error rate after correction has been performed.

FIG. 24 illustrates a chart of the expected system error rate vs. the raw error rate for cases varying raw error rates and varying numbers of imaging cycles. The data for the chart was generated using a Monte Carlo simulation in which a large number of system configurations was simulated. To identify 16,384 proteins, a total of 7 data cycles are required for a four color system ($4^7$=16,384). The maximum allowable error rate is calculated by dividing the allowable number of system errors by the number of molecules identified. In this case, for an average of one error per protein the allowable number of errors is 16,384. The number of molecules identified is $4.0 \times 10^8$ (2,500 fields×1.6×105 molecules per field) with an allowable error rate calculate to be $4.1 \times 10^{-5}$.

Reed Solomon encoding requires parity cycles to improve the raw error rate. Assuming a Reed Solomon system over a Galois Field of 4 (mm=4), each symbol (or word) is a 4-bit symbol that can be represented by two 2-bit symbols (i.e. 2 cycles of a 4 color system that obtains 2 bits per cycle). For a Reed Solomon system, the length of the symbol (or code word) is $nn=2^{mm-1}$, or 15 4-bit symbols or equivalently 30 2-bit symbols. This means that up to 30 cycles may be processed by a four-color fluidics/imaging system. The number of errors that can be corrected is 3, 4 or 5 per target which corresponds to tt={3, 4, or 5} parity symbols. Four imaging cycles are required per parity cycle. This gives a total of 7 data cycles for the ID and 12, 16, or 20 imaging cycles for the error correction. This means that the total number of cycles required to identify 16,384 simultaneous proteins is 19, 23 and 27 cycles for 3, 4 and 5 allowable errors per molecule. As previously calculated, the maximum system error rate of $4.1 \times 10^{-5}$ allows one error per protein. If more errors per protein are allowed, then the maximum system error rate can drop proportionately.

FIG. 24 shows the contours of raw error rate vs. system error rate. For 19 imaging cycles a maximum raw error rate allowable is 3%, for 23 cycles the maximum raw error rate allowable is 6%, and for 27 cycles the maximum raw error rate allowable is 13%. It is expected that the raw error rate will be less than 5%, although for all but the rarest proteins raw error rates of up to 20% appear to be well within the acceptable range of this technology.

Since the maximum number of cycles allowable is 30 cycles, more data cycles could be included. In particular, if three more data cycles were included, the number of identifiable targets would increase by 4^3, or 64× resulting in a maximum possible identifiable targets of 1,048,576, a number higher than realistic probe concentrations will allow. However, this illustrates that the technique is scalable to an arbitrarily large number of molecules limited only by biology.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

All references, issued patents and patent applications cited within the body of the instant specification are hereby incorporated by reference in their entirety, for all purposes.

The invention claimed is:

1. A method of identifying an analyte, comprising:
(a) providing at least one analyte of a plurality of analytes, wherein said at least one analyte of said plurality of analytes is immobilized on a substrate;
(b) performing a plurality of cycles of binding one or more probes to said at least one analyte of said plurality of analytes, wherein said plurality of cycles of probe binding generates a sequence of optical signals;
(c) detecting said sequence of optical signals with an imaging system, wherein said imaging system has about 2 pixels per μm² of said substrate; and
(d) processing said sequence of optical signals with an expected sequence of optical signals corresponding to said at least one analyte of said plurality of analytes to generate a decoded sequence of optical signals, wherein said decoded sequence of optical signals identifies said at least one analyte of said plurality of analytes with an error rate less than 5% over at least 20 cycles of said plurality of cycles.

2. A system for identifying an analyte, comprising:
one or more processors and a memory storing one or more programs for execution by said one or more processors, said one or more programs comprising instructions to:
(i) perform a plurality of cycles of binding one or more probes to at least one analyte of a plurality of analytes, wherein said at least one analyte of said plurality of analytes is immobilized on a substrate, and wherein said plurality of cycles of probe binding generates a sequence of optical signals;
(ii) detect said sequence of optical signals with an imaging system, wherein said imaging system has about 2 pixels per um² of said substrate; and
(iii) process said sequence of optical signals with an expected sequence of optical signals corresponding to said at least one analyte of said plurality of analytes to generate a decoded sequence of optical signals, wherein said decoded sequence of optical signals identifies said at least one analyte of said plurality of analytes with an error rate less than 5% over at least 20 cycles of said plurality of cycles.

3. The method of claim 1, wherein said plurality of analytes comprises a protein, a peptide aptamer, or a nucleic acid molecule.

4. The method of claim 1, wherein said one or more probes comprises a tag, wherein said tag detects a presence of said at least one analyte of said plurality of analytes.

5. The method of claim 4, wherein said tag comprises a fluorescent molecule, chemiluminescent molecule, chromophore, enzyme, enzyme substrate, enzyme cofactor, enzyme inhibitor, dye, metal ion, metal sol, ligand, radioactive isotope, or any combination thereof.

6. The method of claim 1, further comprising determining at least K bits of information from said sequence of optical signals of said at least one analyte of said plurality of analytes per cycle of said plurality of cycles.

7. The method of claim 6, wherein L total bits of information equals K*M bits of information, wherein M comprises a number of cycles of said plurality of cycles, and wherein said L total bits of information determines a presence or an absence of said at least one analyte.

8. The method of claim 7, wherein $L > \log_2(N)$, wherein N is a number of analytes of said plurality of analytes.

9. The method of claim 1, wherein each cycle of said plurality of cycles comprises one or more passes of binding a set of said one or more probes to said at least one analyte of said plurality of analytes.

10. The method of claim 9, wherein a first pass of said one or more passes comprises binding a first probe with a first tag to said at least one analyte of said plurality of analytes, wherein a second pass subsequent to said first pass comprises binding a second probe with a second tag to said at least one analyte of said plurality of analytes, and wherein said first tag and said second tag are different.

11. The method of claim 1, wherein, after each cycle of said plurality of cycles, said one or more probes bound to said at least one analyte of said plurality of analytes are stripped from said at least one analyte of said plurality of analytes.

12. The system of claim 2, wherein said plurality of analytes comprises a protein, a peptide aptamer, or a nucleic acid molecule.

13. The system of claim 2, wherein said one or more probes comprises a tag, wherein said tag, when in use, detects a presence of said at least one analyte of said plurality of analytes.

14. The system of claim 13, wherein said tag comprises a fluorescent molecule, chemiluminescent molecule, chromophore, enzyme, enzyme substrate, enzyme cofactor, enzyme inhibitor, dye, metal ion, metal sol, ligand, radioactive isotope, or any combination thereof.

15. The system of claim 2, wherein said instructions comprise determining at least K bits of information from said sequence of optical signals of said at least one analyte per cycle of said plurality of cycles.

16. The system of claim 15, wherein L total bits of information equals K*M bits of information, wherein M comprises a number of cycles of said plurality of cycles, and wherein said L total bits of information are used to determine a presence or an absence of said at least one analyte.

17. The system of claim 16, wherein $L > \log_2(N)$, wherein N is a number of said plurality of analytes.

18. The system of claim 2, wherein each cycle of said plurality of cycles comprises one or more passes of binding a set of said one or more probes to said at least one analyte of said plurality of analytes.

19. The system of claim 18, wherein a first pass of said one or more passes comprises binding a first probe with a first tag to said at least one analyte of said plurality of analytes, wherein a second pass subsequent to said first pass comprises binding a second probe with a second tag to said at least one analyte of said plurality of analytes, and wherein said first tag and said second tag are different.

20. The system of claim 2, wherein after each cycle of said plurality of cycles said one or more probes bound to said at least one analyte are stripped from said at least one analyte.

* * * * *

SEQUENCE LISTING

<160> NUMBER OF SEQ ID NOS: 19

<210> SEQ ID NO 1
<211> LENGTH: 100
<212> TYPE: DNA
<213> ORGANISM: Artificial Sequence
<220> FEATURE:

```
<223> OTHER INFORMATION: Description of Artificial Sequence: Synthetic
      polynucleotide

<400> SEQUENCE: 1
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa                         100

<210> SEQ ID NO 2
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa caaaaaaaaa aaaaaaaaaa   120
aaaaaaaaaa aaaaaaaaaa aaaaaaaaaa aaaaaaaaaa aaaaaaaaaa aaaaaaaaaa   180
aaaaaaaaaa aaaaaaaaaa a                                             201

<210> SEQ ID NO 3
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa aaaaaaaaaa aaaaaaaaaa aaaaaaaaaa   180
aaaaaaaaaa aaaaaaaaaa                                               200

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5AmMC6

<400> SEQUENCE: 4
aaaaaaaaaa aaaaaaaaaa aaaaaaaaaa aaaaaaaaaa gcacccttgg tctcctcca     59

<210> SEQ ID NO 5
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5AmMC6

<400> SEQUENCE: 5
aaaaaaaaaa aaaaaaaaaa aaaaaaaaaa aaaaaaaaaa ctcagcagca tctcagggcc    60
a                                                                    61
```

```
<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5AmMC6

<400> SEQUENCE: 6
aaaaaaaaaa aaaaaaaaaa aaaaaaaaaa aaaaaaaaaa gctgcatgca cgcacacaca        60

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-5Cy3

<400> SEQUENCE: 7
tggaggagac caagggtgca gt                                                  22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-5Cy3

<400> SEQUENCE: 8
tggccctgag atgctgctga gt                                                  22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-5Cy3

<400> SEQUENCE: 9
tgtgtgtgcg tgcatgcagc                                                     20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-5Cy5

<400> SEQUENCE: 10
tggaggagac caagggtgca gt                                                  22

<210> SEQ ID NO 11
<211> LENGTH: 22
<212> TYPE: DNA
```

<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-5Cy5

<400> SEQUENCE: 11
tggccctgag atgctgctga gt                                              22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-5Cy5

<400> SEQUENCE: 12
tgtgtgtgcg tgcatgcagc                                                 20

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5AmMC6

<400> SEQUENCE: 13
aaaaaaactg caccttggt ctcctcca                                         28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5AmMC6

<400> SEQUENCE: 14
aaaaaaactc agcagcatct cagggcca                                        28

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5AmMC6

<400> SEQUENCE: 15
aaaaaagctg catgcacgca cacaca                                          26

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: 5'-5AmMC6

<400> SEQUENCE: 16
aaaaaaatcc cagcaccacc actaccga                                              28

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-5Cy3

<400> SEQUENCE: 17
tcggtagtgg tggtgctggg at                                                    22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-5Cy5

<400> SEQUENCE: 18
tcggtagtgg tggtgctggg at                                                    22

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Pro Asp Thr Arg Pro Ala Pro Gly
1               5
```